United States Patent
Behabtu et al.

(10) Patent No.: US 12,037,420 B2
(45) Date of Patent: *Jul. 16, 2024

(54) DEXTRAN-POLY ALPHA-1,3-GLUCAN GRAFT COPOLYMERS AND SYNTHESIS METHODS THEREOF

(71) Applicant: NUTRITION & BIOSCIENCES USA 4, INC., Rochester, NY (US)

(72) Inventors: Natnael Behabtu, Wilmington, DE (US); Samuel David Arthur, Wilmington, DE (US)

(73) Assignee: NUTRITION &BIOSCIENCES USA 4, INC., Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/412,880

(22) Filed: Aug. 26, 2021

(65) Prior Publication Data
US 2022/0144973 A1     May 12, 2022

Related U.S. Application Data

(63) Continuation of application No. 15/765,522, filed as application No. PCT/US2016/060579 on Nov. 4, 2016, now Pat. No. 11,104,747.

(60) Provisional application No. 62/251,183, filed on Nov. 5, 2015.

(51) Int. Cl.
*C08B 37/02*     (2006.01)
*C12P 19/08*     (2006.01)

(52) U.S. Cl.
CPC .......... *C08B 37/0021* (2013.01); *C12P 19/08* (2013.01)

(58) Field of Classification Search
CPC ....... C08B 37/0021; C12P 19/08; C12P 19/18
See application file for complete search history.

(56) References Cited

U.S. PATENT DOCUMENTS

2014/0087431 A1* 3/2014 Payne ..................... C12P 19/04
435/97
2016/0175811 A1* 6/2016 Behabtu .............. C08B 37/0009
435/97

OTHER PUBLICATIONS

Takehara, T. et al."The extension of alpha-D-1m3-branch linkages by 1,3-alpha-D-glucan synthase . . . " FEMS Microbiol. Lett., vol. 83 , pp. 69-72. (Year: 1991).*
Cote, G. et al."The formation of alpha-D-(1,3) branch linkages . . . " Carbohyd. Res., vol. 127, pp. 95-107. (Year: 1984).*
Germaine, G. et al."*Streptococcus* mutans dextransucrase . . . " Infect. Immun., vol. 13, No. 2, pp. 365-372. (Year: 1976).*

* cited by examiner

*Primary Examiner* — Leigh C Maier

(57) ABSTRACT

Compositions are disclosed herein comprising a graft copolymer having (i) a backbone comprising dextran with a molecular weight of at least about 100000 Daltons, and poly alpha-1,3-glucan side chains comprising at least about 95% alpha-1,3-glucosidic linkages. Further disclosed are reactions for producing such graft copolymers, as well as their use in absorbent materials.

20 Claims, 3 Drawing Sheets

Specification includes a Sequence Listing.

DEXTRAN-POLY ALPHA-1,3-GLUCAN GRAFT COPOLYMERS AND SYNTHESIS METHODS THEREOF

This application is a continuation of application Ser. No. 15/765,522 (filed Apr. 3, 2018) (now U.S. Pat. No. 11,104,747), which is the National Stage application of International Application No. PCT/US2016/060579 (filed Nov. 4, 2016), which claims the benefit of U.S. Provisional Application No. 62/251,183 (filed Nov. 5, 2015), the disclosures of which prior applications are incorporated herein by reference in their entirety.

FIELD

This disclosure is in the field of polysaccharides. For example, this disclosure pertains to the production of dextran-poly alpha-1,3-glucan graft copolymers, and use thereof in compositions having advantageous aqueous liquid absorption and filterability functions.

REFERENCE TO SEQUENCE LISTING SUBMITTED ELECTRONICALLY

The official copy of the sequence listing is submitted electronically via EFS-Web or Patent Center as a file named CL6500WOPCT SequenceListing ST25.txt created on Oct. 31, 2016 and having a size of about 80 kilobytes. The sequence listing contained in this file is part of the specification and herein incorporated by reference in its entirety.

BACKGROUND

Driven by a desire to find new structural polysaccharides using enzymatic syntheses or genetic engineering of microorganisms or plant hosts, researchers have discovered polysaccharides that are biodegradable and can be made economically from renewably sourced feedstocks. One such polysaccharide is poly alpha-1,3-glucan, a glucan polymer characterized by having alpha-1,3-glycosidic linkages. This polymer has been isolated by contacting an aqueous solution of sucrose with a glucosyltransferase (GTF) enzyme isolated from *Streptococcus salivarius* (Simpson et al., *Microbiology* 141:1451-1460, 1995).

U.S. Pat. No. 7,000,000 disclosed the preparation of a polysaccharide fiber using an *S. salivarius* gtfJ enzyme. At least 50% of the hexose units within the polymer of this fiber were linked via alpha-1,3-glycosidic linkages. *S. salivarius* gtfJ enzyme utilizes sucrose as a substrate in a polymerization reaction producing poly alpha-1,3-glucan and fructose as end-products (Simpson et al., 1995). The disclosed polymer formed a liquid crystalline solution when it was dissolved above a critical concentration in a solvent or in a mixture comprising a solvent. Continuous, strong, cotton-like fibers were obtained from this solution that could be spun and used in textile applications.

While advances have been made in producing poly alpha-1,3-glucan, issues remain with regard to isolating this glucan product in an economical manner. To that end, disclosed herein is poly alpha-1,3-glucan in the form of a graft copolymer having enhanced filterability and aqueous liquid absorption capacity.

SUMMARY

In one embodiment, the disclosure concerns a composition comprising a graft copolymer that comprises:

(i) a backbone comprising dextran with a weight-average molecular weight (Mw) of at least about 100000 Daltons, and (ii) poly alpha-1,3-glucan side chains comprising at least about 95% alpha-1,3-glucosidic linkages.

Another embodiment is drawn to an enzymatic reaction comprising (i) water, (ii) sucrose, (iii) dextran with a weight-average molecular weight (Mw) of at least about 100000 Daltons, and (iv) a glucosyltransferase enzyme that synthesizes poly alpha-1,3-glucan comprising at least about 95% alpha-1,3-glucosidic linkages, wherein the enzymatic reaction produces a graft copolymer as presently disclosed.

Another embodiment is drawn to a method of preparing a graft copolymer. This method comprises: (a) contacting at least (i) water, (ii) sucrose, (iii) dextran with a weight-average molecular weight (Mw) of at least about 100000 Daltons, and (iv) a glucosyltransferase enzyme that synthesizes poly alpha-1,3-glucan comprising at least about 95% alpha-1,3-glucosidic linkages, whereby a graft copolymer as presently disclosed is produced; and (b) optionally, isolating the graft copolymer produced in step (a).

BRIEF DESCRIPTION OF THE DRAWINGS AND SEQUENCES

FIG. 1: Example of a portion of a dextran-poly alpha-1,3-glucan graft copolymer as presently disclosed. In this particular illustration, a poly alpha-1,3-glucan chain ("glucan graft") is synthesized by a glucosyltransferase enzyme (GTF) off of a pendant glucose that is alpha-1,4-linked to a dextran backbone.

FIG. 2: Graphical representation of a dextran-poly alpha-1,3-glucan graft copolymer in some aspects. The dextran backbone and poly alpha-1,3-glucan side chains are presented roughly to scale with each other. For example, the backbone can be about 1000 DPw, while each side chain can be about 1000 DPw.

FIG. 3. A graph illustrates the effect of starting dextran concentration (g/L) on the DPw of dextran-poly alpha-1,3-glucan graft copolymer produced in 2-hr and 24 hr-glucosyltransferase reactions. Refer to Example 2.

TABLE 1

Summary of Protein SEQ ID Numbers

Figure 1:
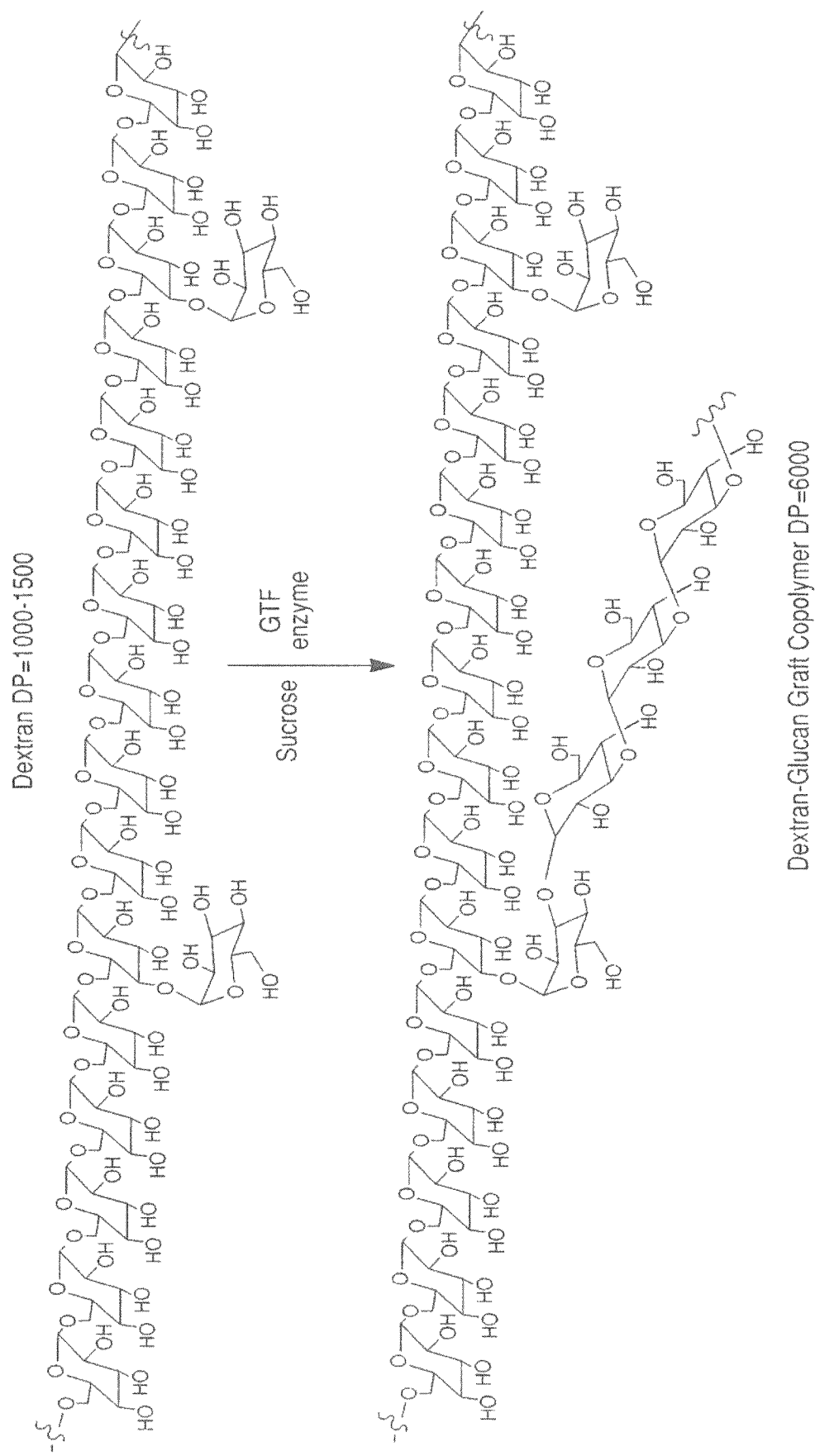

| Description | Protein SEQ ID NO. |
|---|---|
| "GTF 7527" (short version of GtfJ), *Streptococcus salivarius*. The first 178 amino acids of the protein are deleted compared to GENBANK Identification No. 47527; a start methionine is included. | 1 (1341 aa) |
| "GTF 2678", *Streptococcus salivarius* K12. The first 188 amino acids of the protein are deleted compared to GENBANK Identification No. 400182678; a start methionine is included. | 2 (1341 aa) |
| "GTF 6855", *Streptococcus salivarius* SK126. The first 178 amino acids of the protein are deleted compared to GENBANK Identification No. 228476855; a start methionine is included. | 3 (1341 aa) |

TABLE 1-continued

Summary of Protein SEQ ID Numbers

| Description | Protein SEQ ID NO. |
|---|---|
| "GTF 2919", *Streptococcus salivarius* PS4. The first 92 amino acids of the protein are deleted compared to GENBANK Identification No. 383282919; a start methionine is included. | 4 (1340 aa) |
| "GTF 2765", unknown *Streptococcus* sp. C150. The first 193 amino acids of the protein are deleted compared to GENBANK Identification No. 322372765; a start methionine is included. | 5 (1340 aa) |
| "GTF 0768", *Leuconostoc pseudomesenteroides*. Mature form of GENBANK Identification No. 497964659. | 6 (1447 aa) |
| "GTF 0768", *L. pseudomesenteroides*. Mature form of GENBANK Identification No. 497964659, but including a start methionine and additional N- and C-terminal amino acids. | 7 (1457 aa) |

DETAILED DESCRIPTION

The disclosures of all cited patent and non-patent literature are incorporated herein by reference in their entirety.

Unless otherwise disclosed, the terms "a" and "an" as used herein are intended to encompass one or more (i.e., at least one) of a referenced feature.

Where present, all ranges are inclusive and combinable, except as otherwise noted. For example, when a range of "1 to 5" is recited, the recited range should be construed as including ranges "1 to 4", "1 to 3", "1-2", "1-2 & 4-5", "1-3 & 5", and the like.

The term "copolymer" herein refers to a polymer comprising at least two different types of alpha-glucan, such as dextran and poly alpha-1,3-glucan.

The terms "graft copolymer", "branched copolymer" and the like herein generally refer to a copolymer comprising a "backbone" (or "main chain") and side chains branching from the backbone. The side chains are structurally distinct from the backbone. Examples of graft copolymers herein comprise a backbone comprising dextran with a Mw of at least about 100000 Daltons, and side chains of poly alpha-1,3-glucan comprising at least about 95% alpha-1,3-glucosidic linkages. In some aspects, a dextran backbone can have a poly alpha-1,3-glucan extension, since the non-reducing end of dextran can prime poly alpha-1,3-glucan synthesis by a glucosyltransferase enzyme. A backbone can thus be a dextran-poly alpha-1,3-glucan linear copolymer in some instances. A backbone in some aspects can itself be a branched structure as disclosed below; the addition of poly alpha-1,3-glucan to such a backbone increases the branching of the original branched structure.

The terms "poly alpha-1,3-glucan side chain" and "poly alpha-1,3-glucan branch" can be used interchangeably herein. A poly alpha-1,3-glucan side chain is typically an extension of a dextran branch (e.g., pendant glucose or short chain), since a dextran branch has a non-reducing end that can prime poly alpha-1,3-glucan synthesis by a glucosyltransferase enzyme.

"Poly alpha-1,3-glucan homopolymer" and like terms as used herein refer to poly alpha-1,3-glucan that is not part of (i) a graft copolymer or (ii) part of a dextran-poly alpha-1,3-glucan linear copolymer.

The terms "alpha-glucan", "alpha-glucan polymer" and the like are used interchangeably herein. An alpha-glucan is a polymer comprising glucose monomeric units linked together by alpha-glucosidic linkages. Dextran and poly alpha-1,3-glucan are examples of alpha-glucans.

The terms "glycosidic linkage", "glycosidic bond" and the like are used interchangeably herein and refer to the covalent bond that joins a carbohydrate molecule to another carbohydrate molecule. The terms "glucosidic linkage", "glucosidic bond" and the like are used interchangeably herein and refer to a glycosidic linkage between two glucose molecules. The term "alpha-1,6-glucosidic linkage" as used herein refers to the covalent bond that joins alpha-D-glucose molecules to each other through carbons 1 and 6 on adjacent alpha-D-glucose rings. The term "alpha-1,3-glucosidic linkage" as used herein refers to the covalent bond that joins alpha-D-glucose molecules to each other through carbons 1 and 3 on adjacent alpha-D-glucose rings. The term "alpha-1,2-glucosidic linkage" as used herein refers to the covalent bond that joins alpha-D-glucose molecules to each other through carbons 1 and 2 on adjacent alpha-D-glucose rings. The term "alpha-1,4-glucosidic linkage" as used herein refers to the covalent bond that joins alpha-D-glucose molecules to each other through carbons 1 and 4 on adjacent alpha-D-glucose rings. Herein, "alpha-D-glucose" will be referred to as "glucose." All glucosidic linkages disclosed herein are alpha-glucosidic linkages, except as otherwise noted.

The terms "poly alpha-1,3-glucan", "alpha-1,3-glucan polymer" and the like are used interchangeably herein. Poly alpha-1,3-glucan herein comprises at least 95% alpha-1,3-glycosidic linkages. Poly alpha-1,3-glucan that comprises 95%, 96%, 97%, 98%, or 99% alpha-1,3-glycosidic linkages is expected to be mostly unbranched, and that comprising 100% alpha-1,3-glycosidic linkages is linear/unbranched.

The terms "dextran", "dextran polymer", "dextran molecule" and the like are used interchangeably herein and refer to an alpha-glucan generally comprising a main chain with substantially (mostly) alpha-1,6-linked glucose monomers, with periodic branches linked to the main chain by alpha-1,3, alpha-1,2, and/or alpha-1,4 linkages.

A dextran main chain herein comprises more than about 90-95% of all the glucose monomers of a dextran polymer in some aspects. A dextran main chain in some instances can comprise substantially [or mostly] alpha-1,6 linkages, meaning that it can have at least about 98.0% alpha-1,6 linkages. A dextran main chain can comprise a small amount of alpha-1,3 linkages in some aspects, meaning that it can have less than about 2.0% alpha-1,3 linkages.

Dextran branches typically are short, being one (pendant) to three glucose monomers in length, and comprise less than about 10% of all the glucose monomers of a dextran polymer. Such short branches can comprise alpha-1,2-, alpha-1,3-, and/or alpha-1,4-glucosidic linkages. Dextran in some embodiments can also have branches comprising mostly alpha-1,6 linkages. The length of such a branch can be similar to the length of the chain from which the branch originates.

The glycosidic linkage profile of an alpha-glucan herein can be determined using any method known in the art. For example, a linkage profile can be determined using methods that use nuclear magnetic resonance (NMR) spectroscopy (e.g., $^{13}$C NMR or $^{1}$H NMR). These and other methods that can be used are disclosed in *Food Carbohydrates: Chemistry, Physical Properties, and Applications* (S. W. Cui, Ed., Chapter 3, S. W. Cui, Structural Analysis of Polysaccharides, Taylor & Francis Group LLC, Boca Raton, F L, 2005), which is incorporated herein by reference.

The "molecular weight" of dextran herein can be represented as number-average molecular weight (Mn) or as weight-average molecular weight (Mw), the units of which are in Daltons or grams/mole. Alternatively, molecular weight can be represented as DPw (weight average degree of polymerization) or DPn (number average degree of polymerization). Various means are known in the art for calculating these molecular weight measurements such as with high-pressure liquid chromatography (HPLC), size exclusion chromatography (SEC), or gel permeation chromatography (GPC).

The term "sucrose" herein refers to a non-reducing disaccharide composed of an alpha-D-glucose molecule and a beta-D-fructose molecule linked by an alpha-1,2-glycosidic bond. Sucrose is known commonly as table sugar.

The terms "glucosyltransferase enzyme", "GTF enzyme", "GTF", "glucansucrase" and the like are used interchangeably herein. The activity of a glucosyltransferase herein catalyzes the reaction of the substrate sucrose to make the products alpha-glucan and fructose. Other products (byproducts) of a glucosyltransferase reaction can include glucose and various soluble oligosaccharides (DP2-DP7) including leucrose. Wild type forms of glucosyltransferase enzymes generally contain (in the N-terminal to C-terminal direction) a signal peptide, a variable domain, a catalytic domain, and a glucan-binding domain. A glucosyltransferase herein is classified under the glycoside hydrolase family 70 (GH70) according to the CAZy (Carbohydrate-Active EnZymes) database (Cantarel et al., *Nucleic Acids Res.* 37:D233-238, 2009). The term "dextransucrase" can optionally be used to characterize a glucosyltransferase enzyme that produces dextran.

The term "glucosyltransferase catalytic domain" herein refers to the domain of a glucosyltransferase enzyme that provides alpha-glucan-synthesizing activity to a glucosyltransferase enzyme. A glucosyltransferase catalytic domain preferably does not require the presence of any other domains to have this activity.

The terms "enzymatic reaction" "glucosyltransferase reaction", "glucan synthesis reaction", "reaction solution" and the like are used interchangeably herein and generally refer to a reaction that initially comprises water, sucrose, at least one active glucosyltransferase enzyme, and optionally other components such as dextran. Components that can be further present in a glucosyltransferase reaction typically after it has commenced include fructose, glucose, soluble oligosaccharides (e.g., DP2-DP7) such as leucrose, and soluble and/or insoluble alpha-glucan product(s) of DP8 or higher (e.g., DP100 and higher). An enzymatic reaction herein is not believed to occur in nature.

The term "absorb" as used herein refers to the action of taking up (soaking up) an aqueous liquid. Absorption by a composition as presently disclosed can be measured in terms of water retention value (WRV), or as g aqueous liquid/g graft copolymer (the maximum amount of aqueous liquid that can be soaked into and retained by a certain amount of graft copolymer), for example. WRV can be calculated with respect to any aqueous liquid herein using the following formula, for example: ((mass of wet polymer−mass of dry polymer)/mass of dry polymer)*100.

The terms "aqueous liquid", "aqueous fluid" and the like as used herein can refer to water or an aqueous solution. An "aqueous solution" herein can comprise one or more dissolved salts, where the maximal total salt concentration can be about 3.5 wt % in some embodiments. Although aqueous liquids herein typically comprise water as the only solvent in the liquid, an aqueous liquid can optionally comprise one or more other solvents (e.g., polar organic solvent) that are miscible in water. Thus, an aqueous solution can comprise a solvent having at least about 10 wt % water.

A "higher filtration rate" herein characterizes the filterability of a graft copolymer that is at least about 10% faster than the filterability of a poly alpha-1,3-glucan homopolymer or other control material.

The terms "percent by volume", "volume percent", "vol %", "v/v %" and the like are used interchangeably herein. The percent by volume of a solute in a solution can be determined using the formula: [(volume of solute)/(volume of solution)]×100%.

The terms "percent by weight", "weight percentage (wt %)", "weight-weight percentage (% w/w)" and the like are used interchangeably herein. Percent by weight refers to the percentage of a material on a mass basis as it is comprised in a composition, mixture, or solution.

The terms "polynucleotide", "polynucleotide sequence", "nucleic acid sequence", "nucleotide sequence" and the like are used interchangeably herein. A polynucleotide may be a polymer of DNA or RNA that is single- or double-stranded, that optionally contains synthetic, non-natural or altered nucleotide bases. A polynucleotide may be comprised of one or more segments of cDNA, genomic DNA, synthetic DNA, or mixtures thereof. Nucleotides (ribonucleotides or deoxyribonucleotides) can be referred to by a single letter designation as follows: "A" for adenylate or deoxyadenylate (for RNA or DNA, respectively), "C" for cytidylate or deoxycytidylate (for RNA or DNA, respectively), "G" for guanylate or deoxyguanylate (for RNA or DNA, respectively), "U" for uridylate (for RNA), "T" for deoxythymidylate (for DNA), "R" for purines (A or G), "Y" for pyrimidines (C or T), "K" for G or T, "H" for A or C or T, "I" for inosine, "W" for A or T, and "N" for any nucleotide (e.g., N can be A, C, T, or G, if referring to a DNA sequence; N can be A, C, U, or G, if referring to an RNA sequence).

The term "gene" as used herein refers to a DNA polynucleotide sequence that expresses an RNA (RNA is transcribed from the DNA polynucleotide sequence) from a coding region, which RNA can be a messenger RNA (encoding a protein) or a non-protein-coding RNA. A gene may refer to the coding region alone, or may include regulatory sequences upstream and/or downstream to the coding region (e.g., promoters, 5'-untranslated regions, 3'-transcription terminator regions). A coding region encoding a protein can alternatively be referred to herein as an "open reading frame" (ORF). A gene that is "native" or "endogenous" refers to a gene as found in nature with its own regulatory sequences; such a gene is located in its natural location in the genome of a host cell. A "chimeric" gene refers to any gene that is not a native gene, comprising regulatory and coding sequences that are not found together in nature (i.e., the regulatory and coding regions are heterologous with each other). Accordingly, a chimeric gene may comprise regulatory sequences and coding sequences that are derived from different sources, or regulatory sequences and coding sequences derived from the same source, but arranged in a manner different than that found in nature. A "foreign" or "heterologous" gene refers to a gene that is introduced into the host organism by gene transfer. Foreign/heterologous genes can comprise native genes inserted into a non-native organism, native genes introduced into a new location within the native host, or chimeric genes. Polynucleotide sequences in certain embodiments herein are heterologous. A "transgene" is a gene that has been introduced into the genome by a gene delivery procedure (e.g., transformation). A "codonoptimized" open reading frame has its frequency of codon usage designed to mimic the frequency of preferred codon usage of the host cell.

A "non-native" amino acid sequence or polynucleotide sequence herein comprised in a cell or organism herein does not occur in a native (natural) counterpart of such cell or organism.

"Regulatory sequences" as used herein refer to nucleotide sequences located upstream of a gene's transcription start site (e.g., promoter), 5' untranslated regions, introns, and 3' non-coding regions, and which may influence the transcription, processing or stability, and/or translation of an RNA transcribed from the gene. Regulatory sequences herein may include promoters, enhancers, silencers, 5' untranslated leader sequences, introns, polyadenylation recognition sequences, RNA processing sites, effector binding sites, stem-loop structures, and other elements involved in regulation of gene expression. One or more regulatory elements herein may be heterologous to a coding region herein.

A "promoter" as used herein refers to a DNA sequence capable of controlling the transcription of RNA from a gene. In general, a promoter sequence is upstream of the transcription start site of a gene. Promoters may be derived in their entirety from a native gene, or be composed of different elements derived from different promoters found in nature, or even comprise synthetic DNA segments. Promoters that cause a gene to be expressed in a cell at most times under all circumstances are commonly referred to as "constitutive promoters". One or more promoters herein may be heterologous to a coding region herein.

A "strong promoter" as used herein refers to a promoter that can direct a relatively large number of productive initiations per unit time, and/or is a promoter driving a higher level of gene transcription than the average transcription level of the genes in a cell.

The terms "3' non-coding sequence", "transcription terminator", "terminator" and the like as used herein refer to DNA sequences located downstream of a coding sequence. This includes polyadenylation recognition sequences and other sequences encoding regulatory signals capable of affecting mRNA processing or gene expression.

As used herein, a first nucleic acid sequence is "hybridizable" to a second nucleic acid sequence when a single-stranded form of the first nucleic acid sequence can anneal to the second nucleic acid sequence under suitable annealing conditions (e.g., temperature, solution ionic strength). Hybridization and washing conditions are well known and exemplified in Sambrook J, Fritsch E F and Maniatis T, *Molecular Cloning: A Laboratory Manual*, 2nd ed., Cold Spring Harbor Laboratory: Cold Spring Harbor, NY (1989), which is incorporated herein by reference, particularly Chapter 11 and Table 11.1.

The terms "cassette", "expression cassette", "gene cassette" and the like are used interchangeably herein. A cassette can refer to a promoter operably linked to a DNA sequence encoding a protein-coding RNA. A cassette may optionally be operably linked to a 3' non-coding sequence. The structure of a cassette herein can optionally be represented by the simple notation system of "X::Y::Z". Specifically, X describes a promoter, Y describes a coding sequence, and Z describes a terminator (optional); X is operably linked to Y, and Y is operably linked to Z.

The terms "upstream" and "downstream" as used herein with respect to polynucleotides refer to "5' of" and "3' of", respectively.

The term "expression" as used herein refers to (i) transcription of RNA (e.g., mRNA or a non-protein-coding RNA) from a coding region, and/or (ii) translation of a polypeptide from mRNA. Expression of a coding region of a polynucleotide sequence can be up-regulated or down-regulated in certain embodiments.

The term "operably linked" as used herein refers to the association of two or more nucleic acid sequences such that the function of one is affected by the other. For example, a promoter is operably linked with a coding sequence when it is capable of affecting the expression of that coding sequence. That is, the coding sequence is under the transcriptional control of the promoter. A coding sequence can be operably linked to one (e.g., promoter) or more (e.g., promoter and terminator) regulatory sequences, for example.

The term "recombinant" when used herein to characterize a DNA sequence such as a plasmid, vector, or construct refers to an artificial combination of two otherwise separated segments of sequence, e.g., by chemical synthesis and/or by manipulation of isolated segments of nucleic acids by genetic engineering techniques. Methods for preparing recombinant constructs/vectors herein can follow standard recombinant DNA and molecular cloning techniques as described by J. Sambrook and D. Russell (*Molecular Cloning: A Laboratory Manual*, 3rd Edition, Cold Spring Harbor Laboratory Press, Cold Spring Harbor, N Y, 2001); T. J. Silhavy et al. (*Experiments with Gene Fusions*, Cold Spring Harbor Laboratory Press, Cold Spring Harbor, N Y, 1984); and F. M. Ausubel et al. (*Short Protocols in Molecular Biology*, 5th Ed. Current Protocols, John Wiley and Sons, Inc., NY, 2002), for example.

The term "transformation" as used herein refers to the transfer of a nucleic acid molecule into a host organism or host cell by any method. A nucleic acid molecule that has been transformed into an organism/cell may be one that replicates autonomously in the organism/cell, or that integrates into the genome of the organism/cell, or that exists transiently in the cell without replicating or integrating. Non-limiting examples of nucleic acid molecules suitable for transformation are disclosed herein, such as plasmids and linear DNA molecules. Host organisms/cells herein containing a transforming nucleic acid sequence can be referred to as "transgenic", "recombinant", "transformed", "engineered", as a "transformant", and/or as being "modified for exogenous gene expression", for example.

The terms "sequence identity" or "identity" as used herein with respect to polynucleotide or polypeptide sequences refer to the nucleic acid bases or amino acid residues in two sequences that are the same when aligned for maximum correspondence over a specified comparison window. Thus, "percentage of sequence identity" or "percent identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. It would be understood that, when calculating sequence identity between a DNA sequence and an RNA sequence, T residues of the DNA sequence align with, and can be considered "identical" with, U residues of the RNA sequence. For purposes of determining "percent complementarity" of first and second polynucleotides, one can obtain this by determining (i) the percent identity between the first polynucleotide and the complement sequence of the second polynucleotide (or vice versa), for example, and/or (ii) the percentage of bases between the first and second polynucleotides that would create canonical Watson and Crick base pairs.

The Basic Local Alignment Search Tool (BLAST) algorithm, which is available online at the National Center for Biotechnology Information (NCBI) website, may be used, for example, to measure percent identity between or among two or more of the polynucleotide sequences (BLASTN algorithm) or polypeptide sequences (BLASTP algorithm) disclosed herein. Alternatively, percent identity between sequences may be performed using a Clustal algorithm (e.g., ClustalW, ClustalV, or Clustal-Omega). For multiple alignments using a Clustal method of alignment, the default values may correspond to GAP PENALTY=10 and GAP LENGTH PENALTY=10. Default parameters for pairwise alignments and calculation of percent identity of protein sequences using a Clustal method may be KTUPLE=1, GAP PENALTY=3, WINDOW=5 and DIAGONALS SAVED=5. For nucleic acids, these parameters may be KTUPLE=2, GAP PENALTY=5, WINDOW=4 and DIAGONALS SAVED=4. Alternatively still, percent identity between sequences may be performed using an EMBOSS algorithm (e.g., needle) with parameters such as GAP OPEN=10, GAP EXTEND=0.5, END GAP PENALTY=false, END GAP OPEN=10, END GAP EXTEND=0.5 using a BLOSUM matrix (e.g., BLOSUM62).

Various polypeptide amino acid sequences are disclosed herein as features of certain embodiments. Variants of these sequences that are at least about 70-85%, 85-90%, or 90%-95% identical to the sequences disclosed herein can be used or referenced. Alternatively, a variant amino acid sequence can have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity with a sequence disclosed herein. The variant amino acid sequence has the same function/activity of the disclosed sequence, or at least about 80%, 81%, 82%, 83%, 84%, 85%, 86%, 87%, 88%, 89%, 90%, 91%, 92%, 93%, 94%, 95%, 96%, 97%, 98%, or 99% of the function/activity of the disclosed sequence. Any polypeptide amino acid sequence disclosed herein not beginning with a methionine can typically further comprise at least a start-methionine at the N-terminus of the amino acid sequence. Any polypeptide amino acid sequence disclosed herein beginning with a methionine can optionally be considered without this methionine residue (i.e., a polypeptide sequence can be referred to in reference to the position-2 residue to the C-terminal residue of the sequence).

The term "isolated" as used herein refers to a polypeptide molecule (e.g., glucosyltransferase) that has been completely or partially purified from its native source. In some instances, an isolated polypeptide molecule is part of a greater composition, buffer system or reagent mix. For example, an isolated polypeptide molecule can be comprised within a cell or organism in a heterologous manner. A graft copolymer herein (and a reaction for it synthesis) can also be considered to be isolated since it is synthetic/man-made, and/or has properties that are not naturally occurring.

The term "increased" as used herein can refer to a quantity or activity that is at least about 1%, 2%, 3%, 4%, 5%, 6%, 7%, 8%, 9%, 10%, 11%, 12%, 13%, 14%, 15%, 16%, 17%, 18%, 19%, 20%, 50%, 100%, or 200% more than the quantity or activity for which the increased quantity or activity is being compared. The terms "increased", "elevated", "enhanced", "greater than", "improved" and the like are used interchangeably herein.

While advances have been made in producing poly alpha-1,3-glucan, issues remain with regard to isolating this glucan product in an economical manner. Thus, to address this need, disclosed herein is poly alpha-1,3-glucan in the form of a graft copolymer. Various embodiments of such copolymer have enhanced filterability and/or aqueous liquid absorption characteristics.

Certain embodiments of the present disclosure concern a composition comprising a graft copolymer that comprises:
  (i) a backbone comprising dextran with a weight-average molecular weight (Mw) of at least about 100000 Daltons, and
  (ii) poly alpha-1,3-glucan side chains comprising at least about 95% alpha-1,3-glucosidic linkages.

A dextran that forms the backbone of a graft copolymer herein can comprise, for example, about or at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% alpha-1,6-glucosidic linkages. Such a percent alpha-1,6 linkage profile is that taking account the total of all linkages in the dextran (main chain and branch portions combined). "Dextran branches" and like terms herein are meant to encompass any branches that exist in a dextran polymer prior to its use to prepare a graft copolymer as presently disclosed. In some embodiments, a dextran comprises a main chain comprising about, or at least about, 90%, 91%, 92%, 93%, 94%, 95%, 96%, 97%, 98%, 99%, or 100% alpha-1,6-glucosidic linkages.

A dextran herein can comprise, for example, about or at least about 1%, 2%, 3%, 4%, 5%, 6%, 7%, 8%, 9%, 10%, 11%, 12%, 13%, 14%, 15%, 16%, 17%, 18%, 19%, or 20% alpha-1,4, alpha-1,3 and/or alpha-1,2 glucosidic linkages. Typically, such linkages exist entirely, or almost entirely, in branch portions of the dextran, including branch points. In some embodiments, dextran branches may comprise one, two (e.g., alpha-1,4 and alpha-1,3; alpha-1,4 and alpha-1,2; alpha-1,3 and alpha-1,2), or all three of these types of linkages. The total percentage of alpha-1,4, alpha-1,3 and/or alpha-1,2 glucosidic linkages in a dextran herein is typically not greater than 50%. In some aspects, such as with dextran comprising a main chain having about, or at least about, 90%, 91%, 92%, 93%, 94%, 95%, 96%, 97%, 98%, 99%, or 100% alpha-1,6-glucosidic linkages, such dextran comprises about, or at least about, 1%, 2%, 3%, 4%, 5%, 6%, 7%, 8%, 9%, or 10% alpha-1,4, alpha-1,3 and/or alpha-1,2 glucosidic linkages.

A branch point of a dextran herein can comprise an alpha-1,4, alpha-1,3, or alpha-1,2 glucosidic linkage (e.g., a branch may be alpha-1,3-linked to a dextran main chain). In some embodiments, all three of these branch points may exist, whereas in some embodiments only one or two (e.g., alpha-1,4 and alpha-1,3; alpha-1,4 and alpha-1,2; alpha-1,3 and alpha-1,2) types of these branch points exist. It is contemplated that a branch point occurs on average every (or at least every) 5, 10, 15, 20, 25, 30, 35, 40, 45, 50, 10-30, 15-25, 20-30, or 20-40 glucose units of a dextran main chain, for example. Branches of a dextran molecule comprising alpha-1,4, alpha-1,3, and/or alpha-1,2 glucosidic linkages herein typically are one to three glucose monomers in length and comprise less than about 5-10% of all the glucose monomers of a dextran polymer. A branch comprising one glucose unit can be optionally be referred to as a pendant glucose group. In some embodiments, the branches of a dextran molecule can comprise less than about 10%, 9%, 8%, 7%, 6%, 5%, 4%, 3%, 2%, or 1% of all the glucose monomers of a dextran molecule. A dextran in certain embodiments can have about 1%, 2%, 3%, 4%, 5%, 6%, 7%, 8%, 9%, or 10% branch points as a percent of the glucosidic linkages in the polymer. The glucosidic linkage profile of a branch herein can optionally be characterized to include the glucosidic linkage by which the branch is linked to another chain.

A backbone of a graft copolymer in certain embodiments can be comprised entirely of a dextran as presently disclosed. However, in some aspects, a backbone can comprise other elements. For example, a graft copolymer backbone may comprise poly alpha-1,3-glucan originating from the non-reducing side of a dextran main chain, by virtue of the main chain (at its non-reducing end) serving to prime poly alpha-1,3-glucan synthesis during synthesis of the graft copolymer.

The molecular weight (Mw [weight-average molecular weight]) of a dextran that forms the backbone of a graft copolymer herein can be at least about 100000 Daltons. Dextran in certain embodiments can have an Mw of about, or at least about, 100000, 125000, 150000, 175000, 200000, 240000, 250000, 500000, 750000, or 1000000 Daltons, or be in a range of about 100000-200000, 125000-175000, 130000-170000, 135000-165000, 140000-160000, or 145000-155000 Daltons. In some aspects, dextran can have a Mw of about, or at least about, 2, 3, 4, 5, 6, 7, 8, 9, 10, 20, 30, 40, 50, 60, 70, 80, 90, 100, 110, 120, 130, 140, 150, 160, 170, 180, 190, or 200 million Daltons, or can be in a range of about 10-80, 20-70, 30-60, 40-50, 50-200, 60-200, 70-200, 80-200, 90-200, 100-200, 110-200, 120-200, 50-180, 60-180, 70-180, 80-180, 90-180, 100-180, 110-180, 120-180, 50-160, 60-160, 70-160, 80-160, 90-160, 100-160, 110-160, 120-160, 50-140, 60-140, 70-140, 80-140, 90-140, 100-140, 110-140, 120-140, 50-120, 60-120, 70-120, 80-120, 90-120, 90-110, 100-120, 110-120, 50-110, 60-110, 70-110, 80-110, 90-110, 100-110, 50-100, 60-100, 70-100, 80-100, 90-100, or 95-105 million Daltons in some respects. Dextran with a Mw of at least about 50 million herein can optionally be referred to as a "very large dextran". The Mw of dextran herein is not below 100000 Daltons, and thus is not T10 (Mw=10000), T25 (Mw=25000), or T40 (Mw=40000) dextran, for example. Any dextran Mw herein can optionally be expressed as weight-average degree of polymerization (DPw), which is Mw divided by 162.14. Any of the foregoing dextran Mw's can be considered an average Mw of all the dextran molecules in a dextran sample, for example.

A very large dextran in some aspects can comprise (i) about 87-93 wt % glucose linked only at positions 1 and 6; (ii) about 0.1-1.2 wt % glucose linked only at positions 1 and 3; (iii) about 0.1-0.7 wt % glucose linked only at positions 1 and 4; (iv) about 7.7-8.6 wt % glucose linked only at positions 1, 3 and 6; and (v) about 0.4-1.7 wt % glucose linked only at: (a) positions 1, 2 and 6, or (b) positions 1, 4 and 6. In certain embodiments, a dextran can comprise (i) about 89.5-90.5 wt % glucose linked only at positions 1 and 6; (ii) about 0.4-0.9 wt % glucose linked only at positions 1 and 3; (iii) about 0.3-0.5 wt % glucose linked only at positions 1 and 4; (iv) about 8.0-8.3 wt % glucose linked only at positions 1, 3 and 6; and (v) about 0.7-1.4 wt % glucose linked only at: (a) positions 1, 2 and 6, or (b) positions 1, 4 and 6.

A very large dextran in some aspects can comprise about 87, 87.5, 88, 88.5, 89, 89.5, 90, 90.5, 91, 91.5, 92, 92.5, or 93 wt % glucose linked only at positions 1 and 6. There can be about 87-92.5, 87-92, 87-91.5, 87-91, 87-90.5, 87-90, 87.5-92.5, 87.5-92, 87.5-91.5, 87.5-91, 87.5-90.5, 87.5-90, 88-92.5, 88-92, 88-91.5, 88-91, 88-90.5, 88-90, 88.5-92.5, 88.5-92, 88.5-91.5, 88.5-91, 88.5-90.5, 88.5-90, 89-92.5, 89-92, 89-91.5, 89-91, 89-90.5, 89-90, 89.5-92.5, 89.5-92, 89.5-91.5, 89.5-91, or 89.5-90.5 wt % glucose linked only at positions 1 and 6, in some instances.

A very large dextran in some aspects can comprise about 0.1, 0.2, 0.3, 0.4, 0.5, 0.6, 0.7, 0.8, 0.9, 1.0, 1.1, or 1.2 wt % glucose linked only at positions 1 and 3. There can be about 0.1-1.2, 0.1-1.0, 0.1-0.8, 0.3-1.2, 0.3-1.0, 0.3-0.8, 0.4-1.2, 0.4-1.0, 0.4-0.8, 0.5-1.2, 0.5-1.0, 0.5-0.8, 0.6-1.2, 0.6-1.0, or 0.6-0.8 wt % glucose linked only at positions 1 and 3, in some instances.

A very large dextran in some aspects can comprise about 0.1, 0.2, 0.3, 0.4, 0.5, 0.6, or 0.7 wt % glucose linked only at positions 1 and 4. There can be about 0.1-0.7, 0.1-0.6, 0.1-0.5, 0.1-0.4, 0.2-0.7, 0.2-0.6, 0.2-0.5, 0.2-0.4, 0.3-0.7, 0.3-0.6, 0.3-0.5, or 0.3-0.4 wt % glucose linked only at positions 1 and 4, in some instances.

A very large dextran in some aspects can comprise about 7.7, 7.8, 7.9, 8.0, 8.1, 8.2, 8.3, 8.4, 8.5, or 8.6 wt % glucose linked only at positions 1, 3 and 6. There can be about 7.7-8.6, 7.7-8.5, 7.7-8.4, 7.7-8.3, 7.7-8.2, 7.8-8.6, 7.8-8.5, 7.8-8.4, 7.8-8.3, 7.8-8.2, 7.9-8.6, 7.9-8.5, 7.9-8.4, 7.9-8.3, 7.9-8.2, 8.0-8.6, 8.0-8.5, 8.0-8.4, 8.0-8.3, 8.0-8.2, 8.1-8.6, 8.1-8.5, 8.1-8.1, 8.1-8.3, or 8.1-8.2 wt % glucose linked only at positions 1, 3 and 6, in some instances.

A very large dextran in some aspects can comprise about 0.4, 0.5, 0.6, 0.7, 0.8, 0.9, 1.0, 1.1, 1.2, 1.3, 1.4, 1.5, 1.6, or 1.7 wt % glucose linked only at (a) positions 1, 2 and 6, or (b) positions 1, 4 and 6. There can be about 0.4-1.7, 0.4-1.6, 0.4-1.5, 0.4-1.4, 0.4-1.3, 0.5-1.7, 0.5-1.6, 0.5-1.5, 0.5-1.4, 0.5-1.3, 0.6-1.7, 0.6-1.6, 0.6-1.5, 0.6-1.4, 0.6-1.3, 0.7-1.7, 0.7-1.6, 0.7-1.5, 0.7-1.4, 0.7-1.3, 0.8-1.7, 0.8-1.6, 0.8-1.5, 0.8-1.4, 0.8-1.3 wt % glucose linked only at (a) positions 1, 2 and 6, or (b) positions 1, 4 and 6, in some instances.

"Glucose (glucose monomers) linked at positions 1 and 6" herein refers to a glucose monomer of dextran in which only carbons 1 and 6 of the glucose monomer are involved in respective glucosidic linkages with two adjacent glucose monomers. This definition likewise applies to glucose (i) "linked at positions 1 and 3", and (ii) "linked at positions 1 and 4", taking into account, accordingly, the different carbon positions involved in each respective linkage.

"Glucose (glucose monomers) linked at positions 1, 3 and 6" herein refers to a glucose monomer of dextran in which carbons 1, 3 and 6 of the glucose monomer are involved in respective glucosidic linkages with three adjacent glucose monomers. A glucose linked only at positions 1, 3 and 6 is a branch point. This definition likewise applies to glucose linked at (i) positions 1, 2 and 6, and (ii) positions 1, 4 and 6, but taking into account, accordingly, the different carbon positions involved in each respective linkage.

Glucose positions (glucose carbon positions) 1, 2, 3, 4 and 6 herein are as known in the art (depicted in the following structure):

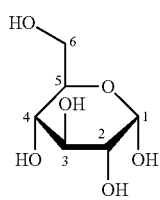

The glucosidic linkage profile of a very large dextran can be determined using dextran produced following any protocol disclosed herein. An example of a suitable linkage determination protocol can be similar to, or the same as, the protocol disclosed in Example 8. For example, an 0768 gtf enzyme reaction that has been deactivated by heating the reaction at about 70-90° C. (e.g., 80° C.) for about 5-30 minutes (e.g., 10 minutes) is placed into dialysis tubing (e.g., made with regenerated cellulose) with an MWCO of 12-14 kDa (e.g., Spectra/Por® 4 Dialysis Tubing, Part No. 132706, Spectrum Laboratories, Inc.). The deactivated reaction is then dialyzed against a large volume of water (e.g., 3-5 L) at about 20-25° C. (room temp) over about 4-10 days (e.g., 7 days); this water can be exchanged every day during the dialysis. The dextran product is then (i) precipitated by mixing the dialyzed deactivated reaction with about 1-2× (1.5×) reaction volume of 100% methanol, (ii) washed at least two times with the same volume of 100% methanol, and (iii) dried at about 40-50° C. (e.g., 45° C.) (optionally under a vacuum). A dissolvable amount of dry dextran is dissolved in dimethyl sulfoxide (DMSO) or DMSO/5% LiCL, after which all free hydroxyl groups are methylated (e.g., by sequential addition of a NaOH/DMSO slurry followed with iodomethane). The methylated dextran is then extracted (e.g., into methylene chloride) and hydrolyzed to monomeric units using aqueous trifluoroacetic acid (TFA) at about 110-125° C. (e.g., 120° C.). The TFA is then evaporated and reductive ring opening is done using sodium borodeuteride. The hydroxyl groups created by hydrolyzing the glycosidic linkages are then acetylated by treating with acetyl chloride and TFA at a temperature of about 40-60° C. (e.g., 50° C.). Next, the derivatizing reagents are evaporated and the resulting methylated/acetylated monomers are reconstituted in acetonitrile; this preparation is then analyzed by GC/MS using an appropriate column (e.g., biscyanopropyl cyanopropylphenyl polysiloxane). The relative positioning of the methyl and acetyl functionalities render species with distinctive retention time indices and mass spectra that can be compared to published databases. In this way, the derivatives of the monomeric units indicate how each monomer was originally linked in the dextran polymer.

It is believed that very large dextran herein may be a branched structure in which there are long chains (containing mostly or all alpha-1,6-linkages) that iteratively branch from each other (e.g., a long chain can be a branch from another long chain, which in turn can itself be a branch from another long chain, and so on). The branched structure may also comprise short branches from the long chains; these short chains are believed to mostly comprise alpha-1,3 and -1,4 linkages, for example. Branch points in the very large dextran, whether from a long chain branching from another long chain, or a short chain branching from a long chain, appear to comprise alpha-1,3, -1,4, or -1,2 linkages off of a glucose involved in alpha-1,6 linkage. On average, about 20%, 21%, 22%, 23%, 24%, 25%, 26%, 27%, 28%, 29%, 30%, 15-35%, 15-30%, 15-25%, 15-20%, 20-35%, 20-30%, 20-25%, 25-35%, or 25-30% of all branch points of very large dextran in some embodiments branch into long chains. Most (>98% or 99%) or all the other branch points branch into short chains.

The long chains of a very large dextran branching structure can be similar in length in some aspects. By being similar in length, it is meant that the length (DP) of at least 70%, 75%, 80%, 85%, or 90% of all the long chains in a branching structure is within plus/minus 15% (or 10%, 5%) of the mean length of all the long chains of the branching structure. In some aspects, the mean length (average length) of the long chains of a very large dextran is about 10-50 DP (i.e., 10-50 glucose monomers). For example, the mean individual length of the long chains can be about 10, 15, 16, 17, 18, 19, 20, 21, 22, 23, 24, 25, 30, 35, 40, 45, 50, 10-50, 10-40, 10-30, 10-25, 10-20, 15-50, 15-40, 15-30, 15-25, 15-20, 20-50, 20-40, 20-30, or 20-25 DP.

Long chains in certain embodiments of very large dextran can comprise substantially alpha-1,6-glucosidic linkages and a small amount (less than 2.0%) of alpha-1,3- and/or alpha-1,4-glucosidic linkages. For example, very large dextran long chains can comprise about, or at least about, 98%, 98.25%, 98.5%, 98.75%, 99%, 99.25%, 99.5%, 99.75%, or 99.9% alpha-1,6-glucosidic linkages. A dextran long chain in certain embodiments does not comprise alpha-1,4-glucosidic linkages (i.e., such a long chain has mostly alpha-1,6 linkages and a small amount of alpha-1,3 linkages). Conversely, a dextran long chain in some embodiments does not comprise alpha-1,3-glucosidic linkages (i.e., such a long chain has mostly alpha-1,6 linkages and a small amount of alpha-1,4 linkages). Any dextran long chain of the above embodiments may further not comprise alpha-1,2-glucosidic linkages, for example. Still in some aspects, a dextran long chain can comprise 100% alpha-1,6-glucosidic linkages (excepting the linkage used by such long chain to branch from another chain).

Short chains of a very large dextran molecule in some aspects are one to three glucose monomers in length and comprise less than about 5-10% of all the glucose monomers of the dextran polymer. At least about 90%, 91%, 92%, 93%, 94%, 95%, 96%, 97%, 98%, 99%, or all of, short chains herein are 1-3 glucose monomers in length. The short chains of a dextran molecule can comprise less than about 10%, 9%, 8%, 7%, 6%, 5%, 4%, 3%, 2%, or 1% of all the glucose monomers of a very large dextran molecule, for example.

Short chains of a very large dextran molecule in some aspects can comprise alpha-1,2-, alpha-1,3-, and/or alpha-1,4-glucosidic linkages. Short chains, when considered all together (not individually) may comprise (i) all three of these linkages, or (ii) alpha-1,3- and alpha-1,4-glucosidic linkages, for example.

In embodiments in which a very large dextran was used to create a copolymer as presently disclosed, it is contemplated that a "backbone" is a long chain of the very large dextran. A poly alpha-1,3-glucan side chain can be linked to a long chain of a very large dextran in a manner as presently disclosed throughout (e.g., extension from the non-reducing end of a short chain or of a long chain).

The Mw of a very large dextran herein is about 50-200 million, or any Mw as disclosed above falling within this range.

The z-average radius of gyration of a very large dextran herein can be about 200-280 nm. For example, the z-average Rg can be about 200, 205, 210, 215, 220, 225, 230, 235, 240, 245, 250, 255, 260, 265, 270, 275, or 280 nm (or any integer between 200-280 nm). As other examples, the z-average Rg can be about 200-280, 200-270, 200-260, 200-250, 200-240, 200-230, 220-280, 220-270, 220-260, 220-250, 220-240, 220-230, 230-280, 230-270, 230-260, 230-250, 230-240, 240-280, 240-270, 240-260, 240-250, 250-280, 250-270, or 250-260 nm.

The term "radius of gyration" (Rg) herein refers to the mean radius of dextran, and is calculated as the root-mean-square distance of a dextran molecule's components (atoms) from the molecule's center of gravity. Rg can be provided in Angstrom or nanometer (nm) units, for example. The "z-average radius of gyration" of dextran herein refers to the Rg of dextran as measured using light scattering (e.g., MALS). Methods for measuring z-average Rg are known and can be used herein, accordingly. For example, z-average Rg can be measured as disclosed in U.S. Pat. No. 7,531,073, U.S. Patent Appl. Publ. Nos. 2010/0003515 and 2009/0046274, Wyatt (*Anal. Chim. Acta* 272:1-40), and Mori and Barth (Size Exclusion Chromatography, Springer-Verlag, Berlin, 1999), all of which are incorporated herein by reference.

The Mw and/or z-average Rg of very large dextran in some aspects can be measured following a protocol similar to, or the same as, the protocol disclosed in Example 8. For example, a Mw and/or z-average Rg herein can be measured by first dissolving dextran produced by an 0768 gtf at 0.4-0.6 mg/mL (e.g., ~0.5 mg/mL) in 0.05-1.0 M (e.g., ~0.075 M) Tris(hydroxymethyl)aminomethane buffer with 150-250 ppm (e.g., ~200 ppm) $NaN_3$. Solvation of dry dextran can be achieved by shaking for 12-18 hours at 45-55° C. (e.g., ~50° C.). The resulting dextran solution can be entered into a suitable flow injection chromatographic apparatus comprising a separation module (e.g., Alliance™ 2695 separation module from Waters Corporation, Milford, MA) coupled with three online detectors: a differential refractometer (e.g., Waters 2414 refractive index detector), a multiangle light scattering (MALS) photometer (e.g., Heleos™-2 18-angle multiangle MALS photometer) equipped with a quasielastic light scattering (QELS) detector (e.g., QELS detector from Wyatt Technologies, Santa Barbara, CA), and a differential capillary viscometer (e.g., ViscoStar™ differential capillary viscometer from Wyatt). Two suitable size-exclusion columns (e.g., AQUAGEL-OH GUARD columns from Agilent Technologies, Santa Clara, CA) can be used to separate the dextran polymer peak from the injection peak, where the mobile phase can be the same as the sample solvent (above), the flow rate can be about 0.2 mL/min, the injection volumes can be about 0.1 mL, and column temperature can be about 30° C. Suitable software can be used for data acquisition (e.g., Empower™ version 3 software from Waters) and for multidetector data reduction (Astra™ version 6 software from Wyatt). MALS data can provide weight-average molecular weight (Mw) and z-average radius of gyration (Rg), and QELS data can provide z-average hydrodynamic radius, for example.

A very large dextran herein can be a product of a glucosyltransferase enzyme comprising, or consisting of, an amino acid sequence that is 100% identical to, or at least 90%, 91%, 92%, 93%, 94%, 95%, 96%, 97%, 98%, or 99% identical to, SEQ ID NO:6 or SEQ ID NO:7 (and have very large dextran-synthesizing activity). Non-limiting examples of a glucosyltransferase enzyme comprising SEQ ID NO:6 (or a related sequence) include glucosyltransferase enzymes comprising, or consisting of, an amino acid sequence that is 100% identical to, or at least 90%, 91%, 92%, 93%, 94%, 95%, 96%, 97%, 98%, or 99% identical to, SEQ ID NO:7 (and have very large dextran-synthesizing activity). A very large dextran can be a product of a *Leuconostoc pseudomesenteroides* glucosyltransferase enzyme, but not a *Leuconostoc mesenteroides* glucosyltransferase enzyme, in certain embodiments.

A glucosyltransferase enzyme used to produce dextran herein is typically in a mature form lacking an N-terminal signal peptide. An expression system for producing a mature glucosyltransferase enzyme herein may employ an enzyme-encoding polynucleotide that further comprises sequence encoding an N-terminal signal peptide to direct extra-cellular secretion. The signal peptide in such embodiments is cleaved from the enzyme during the secretion process. The signal peptide may either be native or heterologous to the glucosyltransferase.

SEQ ID NO:6 is an example of a mature glucosyltransferase enzyme that lacks an N-terminal signal peptide. Since this and related amino acid sequences do not begin with a methionine residue, it would be understood that an N-terminal start-methionine is preferably added to the sequence (directly or via an intervening heterologous amino acid sequence such as an epitope) if expressing any of these enzymes without using a signal peptide (such as with an expression system where the enzyme is expressed intracellularly and obtained from a cell lysate).

A glucosyltransferase enzyme that produces dextran in certain embodiments can be produced by any means known in the art, such as those disclosed below for producing enzymes that synthesize poly alpha-1,3-glucan.

A glucosyltransferase enzyme that produces dextran in certain embodiments may be used in any purification state (e.g., pure or non-pure) as disclosed below for producing enzymes that synthesize poly alpha-1,3-glucan.

The activity of a glucosyltransferase enzyme that produces dextran can be determined using any method known in the art. For example, such enzyme activity can be determined by measuring the production of reducing sugars (fructose and glucose) in a reaction containing sucrose (~50 g/L), dextran T10 (~1 mg/mL) and potassium phosphate buffer (~pH 6.5, 50 mM), where the solution is held at ~22-25° C. for ~24-30 hours. The reducing sugars can be measured by adding 0.01 mL of the reaction to a mixture containing ~1 N NaOH and ~0.1% triphenyltetrazolium chloride and then monitoring the increase in absorbance at $OD_{480\ nm}$ for ~five minutes. Also for instance, a unit of an enzyme such as gtf 0768 (comprising SEQ ID NO: 1) herein can be defined as the amount of enzyme required to consume 1 g of sucrose in 1 hour at 26° C., pH 6.5, and with 100 g/L of sucrose.

A very large dextran can be a product of a glucosyltransferase as comprised in a glucosyltransferase reaction for producing dextran.

The temperature of a glucosyltransferase reaction for producing dextran can be controlled, if desired. In certain embodiments, the temperature is between about 5° C. to about 50° C. The temperature in certain other embodiments is between about 20° C. to about 40° C. Alternatively, the temperature may be about 20, 21, 22, 23, 24, 25, 26, 27, 28, 29, 30, 31, 32, 33, 34, 35, 36, 37, 38, 39, or 40° C.

The initial concentration of sucrose in a glucosyltransferase reaction herein for producing dextran can be about 20 g/L to 900 g/L, 20 g/L to 400 g/L, 75 g/L to 175 g/L, or 50 g/L to 150 g/L. The initial concentration of sucrose can be about 20, 30, 40, 50, 60, 70, 80, 90, 100, 110, 120, 130, 140, 150, 160, 200, 300, 400, 500, 600, 700, 800, 900, 50-150, 75-125, 90-110, 50-500, 100-500, 200-500, 300-500, 400-500, 50-400, 100-400, 200-400, 300-400, 50-300, 100-300, 200-300, 50-200, 100-200, or 50-100 g/L (or any integer between 20 and 900 g/L), for example. Sucrose can be of a purity as disclosed below for reactions that produce poly alpha-1,3-glucan.

The pH of a glucosyltransferase reaction in certain embodiments for producing dextran can be between about 4.0 to about 8.0. Alternatively, the pH can be about 4.0, 4.5, 5.0, 5.5, 6.0, 6.5, 7.0, 7.5, or 8.0. The pH can be adjusted or controlled by the addition or incorporation of a suitable buffer, including but not limited to: phosphate, tris, citrate, or a combination thereof. Buffer concentration in a gtf reaction can be from 0 mM to about 100 mM, or about 10, 20, or 50 mM, for example.

A glucosyltransferase reaction herein for producing dextran can optionally be agitated via stirring or orbital shaking, for example. Such agitation can be at about 50, 60, 70, 80, 90, 100, 110, 120, 130, 140, 150, 50-150, 60-140, 70-130, 80-120, or 90-110 rpm, for example.

The concentration of glucosyltransferase enzyme in a reaction for producing dextran can be at least about 15, 20, 25, 30, 35, or 40 U/L, for example. In some embodiments, 15-35, 15-30, 15-25, 20-35, 20-30, 20-25, 25-35, 25-30, or 30-35 U/L of glucosyltransferase can be used.

A glucosyltransferase reaction herein for producing dextran can take about 2, 3, 4, 5, 6, 7, 8, 9, 10, 12, 18, 24, 30, 36, 48, 60, 72, 84, 96, 18-30, 20-28, or 22-26 hours to complete. Reaction time may depend, for example, on certain parameters such as the amount of sucrose and glucosyltransferase enzyme used in the reaction.

All the features herein defining a glucosyltransferase reaction for producing dextran can be combined, accordingly. Simply as an example, a reaction using an 0768 glucosyltransferase (comprising SEQ ID NO:1 or related sequence thereof) can initially contain 90-110 g/L (e.g., ~100 g/L) sucrose, 10-30 mM (e.g., ~20 mM) sodium phosphate buffer at pH 6.0-7.0 (e.g., ~pH 6.5), and 20-30 U/L (e.g., ~25 U/L) enzyme. Such a reaction can be held for about 20-28 hours (e.g., ~24 hours) with 50-150 rpm (e.g., ~100 rpm) shaking at 24-28° C. (e.g., ~26° C.).

A graft copolymer herein comprises a dextran backbone from which there are poly alpha-1,3-glucan side chains comprising at least about 95% alpha-1,3-glucosidic linkages. These side chains typically result via reacting a dextran as presently disclosed herein with a glucosyltransferase that can synthesize poly alpha-1,3-glucan. For clarity purposes, these side chains ought not be considered branches of dextran.

A poly alpha-1,3-glucan side chain in certain aspects can comprise about, or at least about, 95%, 96%, 97%, 98%, 99%, 99.5%, or 100% alpha-1,3 glucosidic linkages. Such a side chain is contemplated in some aspects to be synthesized with a glucosyltransferase enzyme using a pendant glucose or other branch portion of dextran (both of which present non-reducing ends to the enzyme for extension) as a primer. Where a side chain is synthesized from a pendant glucose that is itself alpha-1,3-linked to the dextran main chain, the resulting side chain can have 100% or a very high (e.g., 98% or greater) percentage of alpha-1,3-glucosidic linkages. In some embodiments, the glucosidic linkage between a dextran main chain and a pendant glucose or longer branch is considered a linkage of the side chain. In some embodiments, the glucosidic linkage between a dextran main chain and a branch, as well as the glucosidic linkages within a branch from which a side chain was synthesized, are considered in determining the linkage profile of the side chain. Side chains in some embodiments have no alpha-1,6 glucosidic linkages, such as with graft copolymers in which the dextran component is of 100000 to 200000 Daltons.

The Mw of a poly alpha-1,3-glucan side chain herein can be about, or at least about 1620, 1650, 1700, 2000, 5000, 10000, 15000, 16200, 20000, 25000, 30000, 40000, 50000, 60000, 70000, 75000, 80000, 90000, 100000, 110000, 120000, 125000, 130000, 140000, 150000, 160000, 162000, or 165000 Daltons, for example. It is contemplated that the side chains of a graft copolymer herein are relatively homogenous in size. For instance, the sides chains of a graft copolymer may each be at least about 100000, 120000, 140000, 160000, 162000, or 165000 Daltons. Also for instance, the sides chains of a graft copolymer may each have a Mw in the range of about 150000-165000, 155000-165000, or 160000-165000 Daltons. The average Mw of the side chains of a graft copolymer can also be referred to, if desired; any of the foregoing side chain Mw's can be considered an average Mw of all the side chains of a copolymer. Any of the side chain Mw's (or any glucan Mw) disclosed herein can optionally be characterized in terms of DPw (Mw/162.14).

The number of poly alpha-1,3-glucan side chains of a graft copolymer herein can be at least 3, 4, 5, 6, 7, 8, 9, 10, 11, 12, 13, 14, 15, 16, 17, 18, 19, 20, 21, 22, 23, 24, 25, 26, 27, 28, 29, or 30, for example. In some embodiments, the number of side chains is 4, 5, or 6, for example. The foregoing number of poly alpha-1,3-glucan side chains in some aspects is a characteristic of side chains that are at least about 100000, 120000, 140000, 160000, 162000, or 165000 Daltons; any dextran component herein such as a very large dextran or a dextran of 100000 to 200000 Daltons can be comprised in such a copolymer. Still, in further aspects, the foregoing number of poly alpha-1,3-glucan side chains can characterize a graft copolymer in which the dextran component has a pendant glucose and/or branch (from which a side chain can be primed/synthesized) on average once every 15, 16, 17, 18, 19, 20, 21, 22, 23, 24, or 25 glucose units of a dextran main chain. Based on the size of a dextran component (e.g., 100000-200000 Daltons), the positioning of branches/pendant glucoses on the dextran main chain (e.g., about one every 20 glucose units), and the number of poly alpha-1,3-glucan side chains of a graft copolymer, it is contemplated in some cases that a graft copolymer has a majority (e.g., at least 80%, 85%, 90%, 95%) of its original dextran branches/pendant glucoses non-extended into a poly alpha-1,3-glucan side chain (i.e., most of the branches/pendant glucoses are as they existed in the dextran before use thereof to synthesize a graft copolymer herein). Still, in some other embodiments, it is believed possible that a graft copolymer herein can have up to about 50, 100, 500, 1000, 5000, 10000, 15000, or 20000 poly alpha-1,3-glucan side chains.

In certain embodiments in which the dextran component of a graft copolymer has a weight-average molecular weight of at least about 50 million Daltons (e.g., any higher Mw as disclosed above) and/or comprises (i) about 87-93 wt % glucose linked at positions 1 and 6; (ii) about 0.1-1.2 wt % glucose linked at positions 1 and 3; (iii) about 0.1-0.7 wt % glucose linked at positions 1 and 4; (iv) about 7.7-8.6 wt % glucose linked at positions 1, 3 and 6; and (v) about 0.4-1.7 wt % glucose linked at (a) positions 1, 2 and 6, or (b) positions 1, 4 and 6, the side chains of the graft copolymer may comprise at least 30% alpha-1,3-glucosidic linkages and a percentage of alpha-1,6 linkages that brings the total of both the alpha-1,3 and -1,6 linkages in the side chains to 100%. For example, the percentage of alpha-1,3 linkages can be at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, or 95%, while the percentage of alpha-1,6 linkages can be that which brings the total of both the alpha-1,3 and -1,6 linkages in the side chains to 100%. In certain embodiments, such side chains do not comprise alternan (alternating 1,3 and 1,6 linkages). The side chains in some embodiments have a level of alpha-1,3 linkages that render the resulting graft copolymer as insoluble. Glucosyltransferase enzymes that can be used in some aspects to synthesize side chains comprising at least 30% alpha-1,3-glucosidic linkages as above are disclosed in U.S. Patent Appl. Publ. No. 2015/0232819, which is incorporated herein by reference.

All the features disclosed above (aside from chain linkage profile) characterizing side chains comprising at least 95% alpha-1,3-glucosidic linkages (e.g., Mw, number of side chains, spacing on dextran backbone, branch point type) can likewise characterize side chains herein comprising at least 30% alpha-1,3-glucosidic linkages.

The weight-average molecular weight of a dextran-poly alpha-1,3-glucan graft copolymer herein (i.e., the combined Mw of the original dextran molecule and the poly alpha-1,3-glucan side chains of a graft copolymer) can be about, or at least about, 750000, 800000, 900000, 1000000, 1100000, 1200000, 1300000, 1400000, 1500000, 1600000, 1700000, 1800000, 1900000, or 2000000 Daltons, for example. The weight-average molecular weight of a dextran-poly alpha-1,3-glucan graft copolymer that comprises a very large dextran component in some embodiments is believed to similar to the weight as disclosed above for the very large dextran component itself, but with the addition of about 0.5, 0.75, 1, 1.25, 1.5, 1.75 or 2 million Daltons (in embodiments in which there are a few poly alpha-1,3-glucan side chains). In yet some more aspects, the weight-average molecular weight of a dextran-poly alpha-1,3-glucan graft copolymer can be the sum of the Mw of any dextran molecule herein and the Mw of any poly alpha-1,3-glucan side chains (taking into account the number of side chains and Mw of each) disclosed herein. Also, Mw of a graft copolymer herein can optionally be expressed in terms of the dextran component Mw and poly alpha-1,3-glucan side chain Mw. In some aspects, the weight-average molecular weight of a dextran-poly alpha-1,3-glucan graft copolymer is not less than 600000, 650000, or 700000 Daltons.

In certain embodiments, a dextran-poly alpha-1,3-glucan graft copolymer can comprise about, or at least about, 2.0 wt % dextran. The wt % of dextran in a graft copolymer in some additional aspects can be about, or at least about, 0.5%, 1.0%, 1.5%, 2.0%, 2.1%, 2.2%, 2.3%, 2.4%, 2.5%, 3.0%, 3.5%, 4.0%, 5.5%, 6.0%, 6.5%, 7.0%, 7.5%, 8.0%, 8.5%, 9.0%, 9.5%, 10.0%, 10.5%, 11.0%, 11.5%, 12.0%, 15%, 20%, 25%, 30%, 35%, 40%, 45%, 50%, 55%, 60%, 65%, 70%, 75%, 80%, 85%, 90%, 95%, 96%, 97%, 98%, or 99% (or any integer between 1%-99%). A graft copolymer in some embodiments (e.g., those comprising 2%-50%, 2%-11%, 2.5%-10.5%, or >2% dextran) can exhibit enhanced filterability as compared to a graft copolymer comprising the same type of dextran, but at a lower weight percentage (e.g., below 1.6%, 1.5%, 1.4%, 1.3%, 1.2%, 1.1%, 1.0%, 0.9%, or 0.8%). Enhanced filterability herein can optionally refer to the ease by which water and/or an aqueous solution (e.g. liquid portion of an enzymatic reaction used to produce the graft copolymer) can be filtered (e.g., gravity only, displacement washing, applied force) through a bed (e.g., wet cake) of the graft copolymer particles. Graft copolymer herein can exhibit filterability that is about, or at least about, 10%, 20%, 30%, 40%, 50%, 60%, 70%, 80%, 90%, 100%, 150%, 200%, 500%, 1000%, 10000%, or 100000% faster than the filterability of (i) a graft copolymer herein having less than 1.6 wt % dextran (above), or (ii) poly alpha-1,3-glucan homopolymer of 500, 600, 700, 800, 900, or 1000 DPw with at least 95%, 96%, 97%, 98%, 99% or 100% alpha-1,3-linkages. Filterability measurements for making such a comparison can be in units of cake resistance or any other filterability measure. In some cases, the dextran in the foregoing embodiments (graft copolymer comprising at least 2.0 wt % dextran) has an Mw of at least about 50 million or any greater Mw herein. Graft copolymers comprising at least 2.0 wt % dextran herein can appear as particles with an average diameter of about 3.5, 3.75, 4.0, 4.25, 4.5, 4.75, 5.0, 5.25, or 5.5 mm, for example. The enhanced filterability of graft copolymers in certain aspects herein represents an advantage with respect to poly alpha-1,3-glucan homopolymer, which typically is difficult to filter.

The polydispersity index (Mw/Mn) (PDI) of a dextran-poly alpha-1,3-glucan graft copolymer herein can be about, at least about, or less than about, 5.0, 4.75, 4.5, 4.25, 4.0, 3.75, 3.5, 3.25, 3.0, 2.75, 2.5, 2.25, or 2.0, for example. Such a PDI can alternatively characterize all the insoluble products (taken all together) of a glucosyltransferase reaction herein in which both dextran-poly alpha-1,3-glucan graft copolymer and poly alpha-1,3-glucan homopolymer can be produced. In general, a glucosyltransferase reaction herein comprising more initial substrate dextran (e.g., about, or at least about 7.5, 10, 12.5, 15, 17.5, or 20 g/L) yields insoluble product of lower PDI than a glucosyltransferase reaction comprising less initial substrate dextran (e.g., about, or less than about, 5, 4, 3, 2.5, or 2 g/L), all other variables being equal.

A dextran-poly alpha-1,3-glucan graft copolymer as presently disclosed is typically insoluble under aqueous conditions (aqueous insoluble). For example, a graft copolymer can be insoluble or not completely dissolved in water or another aqueous composition at a temperature up to about 50, 60, 70, 80, 90, 100, 110, or 120° C. An aqueous composition herein such as an aqueous solution can comprise a solvent having at least about 10 wt % water. In other embodiments, a solvent is at least about 20, 30, 40, 50, 60, 70, 80, 90, or 100 wt % water (or any integer value between 10 and 100 wt %), for example.

A dextran-poly alpha-1,3-glucan graft copolymer as comprised in a composition herein can absorb an aqueous liquid. An aqueous liquid can be water for instance. An aqueous liquid in certain aspects can be an aqueous solution, such as a salt solution (saline solution). A salt solution can optionally comprise about, or at least about, 0.01, 0.025, 0.05, 0.075, 0.1, 0.25, 0.5, 0.75, 1.0, 1.25, 1.5, 1.75, 2.0, 2.5, 3.0, 3.5, 0.01-3.5, 0.5-3.5, 0.5-2.5, or 0.5-1.5 wt % of salt (such wt % values typically refer to the total concentration of one or more salts). Examples of a salt that can be used in an aqueous solution herein include one or more sodium salts (e.g., NaCl, $Na_2SO_4$). Other non-limiting examples of salts include those having (i) an aluminum, ammonium, barium, calcium, chromium (II or III), copper (I or II), iron (II or III), hydrogen, lead (II), lithium, magnesium, manganese (II or III), mercury (I or II), potassium, silver, sodium strontium, tin (II or IV), or zinc cation, and (ii) an acetate, borate, bromate, bromide, carbonate, chlorate, chloride, chlorite, chromate, cyanamide, cyanide, dichromate, dihydrogen phosphate, ferricyanide, ferrocyanide, fluoride, hydrogen carbonate, hydrogen phosphate, hydrogen sulfate, hydrogen sulfide, hydrogen sulfite, hydride, hydroxide, hypochlorite, iodate, iodide, nitrate, nitride, nitrite, oxalate, oxide, perchlorate, permanganate, peroxide, phosphate, phosphide, phosphite, silicate, stannate, stannite, sulfate, sulfide, sulfite, tartrate, or thiocyanate anion. Thus, any salt having a cation from (i) above and an anion from (ii) above can be in an aqueous liquid as presently disclosed, for example. The level of absorption can be measured by any means known in the art, such as with the protocol presently disclosed in Example 7 (below) regarding measuring WRV (water retention value).

Absorption of an aqueous liquid by a dextran-poly alpha-1,3-glucan graft copolymer as comprised in a composition herein can be gauged by measuring the WRV of the composition, for example. WRV herein can be measured by any means known in the art, such as with the protocol presently disclosed in Example 7 (below). Briefly, WRV can be calculated using the following formula: ((mass of wet polymer−mass of dry polymer)/mass of dry polymer)*100. WRV can be measured with respect to any aqueous liquid as presently disclosed, for example. Thus, while the term WRV contains the word "water", it would be understood that a polymer WRV can be measured regarding any type of aqueous liquid disclosed herein, such as an aqueous solution.

A dextran-poly alpha-1,3-glucan graft copolymer, and/or a composition in which it is comprised, can have a water retention value (WRV) of about, or at least about, 100 in some embodiments. For instance, WRV herein can be about, or at least about, 100, 110, 120, 130, 140, 150, 160, 170, 180, 190, 200, 250, 500, 1000, 1500, 2000, 2500, 3000, 3500, or 4000.

Absorption herein can optionally be measured in terms of the maximum amount of aqueous liquid that can be soaked into and retained by a certain amount of dextran-poly alpha-1,3-glucan graft copolymer (g aqueous liquid/g graft copolymer). Graft copolymer with an absorption capacity of at least 15 g aqueous liquid/g graft copolymer can be characterized as being superabsorbent in some aspects.

While not intending to be held to any particular belief or theory, it is believed that the enhanced WRV of dextran-poly alpha-1,3-glucan graft copolymers herein is attributable, at least in part, to the dextran component thereof. Dextran also appears to "crosslink" (not true chemical crosslinking) poly alpha-1,3-glucan components of individual graft copolymer molecules.

A composition comprising a dextran-poly alpha-1,3-glucan graft copolymer as presently disclosed can be in the form of, or comprised within, a personal care product, household product, medical product, or industrial product, for example. In this context, compositions in certain embodiments can be used as absorbent or superabsorbent materials. Examples of such materials include those that are hypoallergenic. A superabsorbent material herein has an absorption capacity with respect to an aqueous liquid herein of at least 15 g aqueous liquid/g graft copolymer, for example. A personal care product, household product, medical product, or industrial product in some embodiments can comprise an absorbent or superabsorbent material as presently disclosed. One particular advantage of a composition herein is that it is biodegradable and hence environmentally friendly.

Examples of personal care products and/or uses herein include absorbent personal hygiene products such as baby diapers, potty training pants, incontinence products (e.g., pads, adult diapers), and feminine hygiene products (e.g., sanitary napkins/pads, tampons, interlabial products, panty liners).

Examples of industrial products and/or uses herein include telecommunication cable wrappings; food pads; agricultural and forestry applications such as for retaining water in soil and/or to release water to plant roots; firefighting devices; and cleanup of acidic or basic aqueous solutions spills.

Examples of medical products and/or uses herein include wound healing dressings such as bandages and surgical pads; phantoms for ultrasound-based imaging; hospital bed sheets; sanitary towels; controlled drug release devices; cell immobilization islets; three-dimensional cell culture substrates; bioactive scaffolds for regenerative medicine; stomach bulking devices; and disposal of controlled drugs.

Personal care products, household products, and/or medical products in some embodiments herein can absorb a bodily fluid such as urine, blood, blood serum, liquid fecal matter (e.g., diarrhea), bile, stomach acid/juice, vomit, amniotic fluid, breast milk, cerebrospinal fluid, exudate, lymph, mucus (e.g., nasal drainage, phlegm), peritoneal fluid, pleural fluid, pus, rheum, saliva, sputum, synovial fluid, sweat, and/or tears.

One particular advantage of a composition herein is that it is biodegradable and hence environmentally friendly.

A composition as presently disclosed can comprise about, or at least about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99, 99.5, or 99.9 wt %, for example, of one or more dextran-poly alpha-1,3-glucan graft copolymers herein. Dry compositions in certain aspects can be in the form of powder, granules, microcapsules, flakes, or any other form of particulate matter. Other examples include larger compositions such as pellets, bars, kernels, beads, tablets, sticks, or other agglomerates. A dry composition herein typically has less than 3, 2, 1, 0.5, or 0.1 wt % water comprised therein.

Further aspects of the present disclosure are drawn to an enzymatic reaction comprising: (i) water, (ii) sucrose, (iii) dextran with a weight-average molecular weight (Mw) of at least about 100000 Daltons, and (iv) a glucosyltransferase enzyme that synthesizes poly alpha-1,3-glucan comprising at least about 95% alpha-1,3-glucosidic linkages. Such an enzymatic reaction produces a dextran-poly alpha-1,3-glucan graft copolymer as disclosed herein.

Any dextran of at least 100000 Daltons as presently disclosed (e.g., above description or in below Examples) can be used in an enzymatic reaction herein. Dextran as added to an enzymatic reaction can be in the form of a dry powder or a pre-dissolved form, for instance. The initial concentration of dextran in a reaction can be about, or at least about, 0.5 g/L, 1.0 g/L, 1.5 g/L, 2 g/L, 2.5 g/L, 3 g/L, 4 g/L, 5 g/L, 7.5 g/L, 10 g/L, 15 g/L, 20 g/L, or 25 g/L, for example. "Initial concentration of dextran" refers to the dextran concentration in a glucosyltransferase reaction just after all the reaction components have been added (e.g., at least water, sucrose, dextran, glucosyltransferase enzyme).

In some embodiments, an enzymatic reaction may comprise an initial concentration of at least about 2 g/L of dextran (e.g., any other higher concentration as disclosed above) that is at least about 50 million Daltons (e.g., any other higher Mw as disclosed above). Such a reaction can yield a dextran-poly alpha-1,3-glucan graft copolymer with an enhanced filterability profile (any filterability feature[s] as disclosed above). Since advantageous effects on product filterability were observed with initial dextran concentrations as little as 2-10 g/L (Example 6), the initial dextran (Mw≥50 million Daltons) concentration in certain embodiments can be about 2.0 or 2.4 g/L to about 3, 4, 5, 6, 7, 8, 9, or 10 g/L in some instances.

An enzymatic reaction as presently disclosed for producing a graft copolymer comprises a glucosyltransferase enzyme that synthesizes poly alpha-1,3-glucan comprising at least about 95% alpha-1,3-glucosidic linkages. Such an enzyme can synthesize poly alpha-1,3-side chains (as disclosed above) from dextran primer sites, forming a dextran-poly alpha-1,3-glucan graft copolymer herein. Thus, for example, a glucosyltransferase enzyme can synthesize poly alpha-1,3-glucan that (i) comprises at least about 95%, 96%, 97%, 98%, or 99% alpha-1,3-glucosidic linkages, and/or (ii) is at least about 16200 Daltons in Mw.

A glucosyltransferase enzyme in certain embodiments for producing poly alpha-1,3-glucan can comprise, or consist of, an amino acid sequence as disclosed in U.S. Patent Appl. Publ. No. 2014/0087431, for example, which is incorporated herein by reference. Examples of such sequences include those that are 100% identical to, or at least 90%, 91%, 92%, 93%, 94%, 95%, 96%, 97%, 98%, 98.5%, 99%, or 99.5% identical to, SEQ ID NOs: 1, 2, 3, 4, or 5, and have glucosyltransferase activity.

A glucosyltransferase enzyme in certain embodiments can comprise, or consist of, a glucosyltransferase catalytic domain having an amino acid sequence that is 100% identical to, or at least 90%, 91%, 92%, 93%, 94%, 95%, 96%, 97%, 98%, 98.5%, 99%, or 99.5% identical to, amino acid positions 54-957 of SEQ ID NO:1, and have glucosyltransferase activity. A glucosyltransferase enzyme with amino acid positions 54-957 of SEQ ID NO:1 can produce poly alpha-1,3-glucan with 100% alpha-1,3 linkages and a DPw of at least 400 (data not shown, refer to Table 6 of U.S. Pat. Appl. No. 62/180,779), for example.

SEQ ID NOs: 1 (GTF 7527), 2 (GTF 2678), 3 (GTF 6855), 4 (GTF 2919), and 5 (GTF 2765) each represent a glucosyltransferase that, compared to its respective wild type counterpart, lacks the signal peptide domain and all or a substantial portion of the variable domain. Thus, each of these glucosyltransferase enzymes has a catalytic domain followed by a glucan-binding domain. The approximate location of catalytic domain sequences in these enzymes is as follows: 7527 (residues 54-957 of SEQ ID NO: 1), 2678 (residues 55-960 of SEQ ID NO:2), 6855 (residues 55-960 of SEQ ID NO:3), 2919 (residues 55-960 of SEQ ID NO:4), 2765 (residues 55-960 of SEQ ID NO:5). The amino acid sequences of catalytic domains of GTFs 2678, 6855, 2919 and 2765 have about 94.9%, 99.0%, 95.5% and 96.4% identity, respectively, with a catalytic domain sequence of GTF 7527 (i.e., amino acids 54-957 of SEQ ID NO:1). These particular glucosyltransferase enzymes can produce poly alpha-1,3-glucan with 100% alpha-1,3 linkages and a DPw of at least 400 (data not shown, refer to Table 4 of U.S. Pat. Appl. No. 62/180,779). Thus, a glucosyltransferase catalytic domain sequence in certain embodiments can be 100% identical to, or at least 90%, 91%, 92%, 93%, 94%, 95%, 96%, 97%, 98%, 98.5%, 99%, or 99.5% identical to, the amino acid sequence of a catalytic domain of GTF 2678, 6855, 2919, or 2765. In some alternative embodiments, a glucosyltransferase catalytic domain sequence does not comprise residues 54-957 of SEQ ID NO: 1, residues 55-960 of SEQ ID NO:2, residues 55-960 of SEQ ID NO:3, residues 55-960 of SEQ ID NO:4, or residues 55-960 of SEQ ID NO:5.

Although it is believed that a glucosyltransferase enzyme herein need only have a catalytic domain sequence, such as one comprising an amino acid sequence that is at least 90% identical to amino acid positions 54-957 of SEQ ID NO:1 (or positions 55-960 of SEQ ID NO:2, positions 55-960 of SEQ ID NO:3, positions 55-960 of SEQ ID NO:4, or positions 55-960 of SEQ ID NO:5), the glucosyltransferase enzyme can be comprised within a larger amino acid sequence. For example, the catalytic domain may be linked at its C-terminus to a glucan-binding domain, and/or linked at its N-terminus to a variable domain and/or signal peptide.

The catalytic domain of a glucosyltransferase enzyme herein can have activity as exhibited by a catalytic domain of a glucosyltransferase classified under the glycoside hydrolase family 70 (GH70). Such a GH70 glucosyltransferase may be found in the CAZy (Carbohydrate-Active EnZymes) database (Cantarel et al., *Nucleic Acids Res.* 37:D233-238, 2009), for example.

Still further examples of glucosyltransferase enzymes can be any as disclosed herein and that include 1-300 (or any integer there between [e.g., 10, 15, 20, 25, 30, 35, 40, 45, or 50]) residues on the N-terminus and/or C-terminus. Such additional residues may be from a corresponding wild type sequence from which the glucosyltransferase enzyme is derived, or may be a heterologous sequence such as an epitope tag (at either N- or C-terminus) or a heterologous signal peptide (at N-terminus), for example.

A glucosyltransferase enzyme herein typically lacks an N-terminal signal peptide. An expression system for producing a glucosyltransferase enzyme herein may employ an enzyme-encoding polynucleotide that further comprises sequence encoding an N-terminal signal peptide to direct extra-cellular secretion, if desired. The signal peptide in such embodiments is cleaved from the enzyme during the secretion process. The signal peptide may either be native or heterologous to the glucosyltransferase. An example of a signal peptide useful herein is one from a bacterial (e.g., a *Bacillus* species such as *B. subtilis*) or fungal species. An example of a bacterial signal peptide is an aprE signal peptide, such as one from *Bacillus* (e.g., *B. subtilis*, see Vogtentanz et al., *Protein Expr. Purif.* 55:40-52, which is incorporated herein by reference).

A glucosyltransferase enzyme herein can be derived from any microbial source, such as a bacteria or fungus. Examples of bacterial glucosyltransferase enzymes are those derived from a *Streptococcus* species, *Leuconostoc* species or *Lactobacillus* species. Examples of *Streptococcus* species include *S. salivarius, S. sobrinus, S. dentirousetti, S. downei, S. mutans, S. oralis, S. gallolyticus* and *S. sanguinis*. Examples of *Leuconostoc* species include *L. mesenteroides, L. amelibiosum, L. argentinum, L. carnosum, L. citreum, L. cremoris, L. dextranicum* and *L. fructosum*. Examples of *Lactobacillus* species include *L. acidophilus, L. delbrueckii, L. helveticus, L. salivarius, L. casei, L. curvatus, L. plantarum, L. sakei, L. brevis, L. buchneri, L. fermentum* and *L. reuteri*.

A glucosyltransferase enzyme herein can be produced by any means known in the art. For example, a glucosyltransferase enzyme may be produced recombinantly in a heterologous expression system, such as a microbial heterologous expression system. Examples of heterologous expression systems include bacterial (e.g., *E. coli* such as TOP10 or MG1655; *Bacillus* sp.) and eukaryotic (e.g., yeasts such as *Pichia* sp. and *Saccharomyces* sp.) expression systems.

In certain embodiments, a heterologous gene expression system may be one that is designed for protein secretion. A glucosyltransferase enzyme typically comprises a signal peptide (signal sequence) in such embodiments. The signal peptide may be either its native signal peptide or a heterologous signal peptide. A glucosyltransferase enzyme in some embodiments does not occur in nature; for example, an enzyme herein is not believed to be one that is naturally secreted (i.e., mature form) from a microbe (from which the glucosyltransferase enzyme herein could possibly have been derived).

A glucosyltransferase enzyme described herein may be used in any purification state (e.g., pure or non-pure). For example, a glucosyltransferase enzyme may be purified and/or isolated prior to its use. Examples of glucosyltransferase enzymes that are non-pure include those in the form of a cell lysate. A cell lysate or extract may be prepared from a bacteria (e.g., *E. coli*) used to heterologously express the enzyme. For example, the bacteria may be subjected to disruption using a French pressure cell. In alternative embodiments, bacteria may be homogenized with a homogenizer (e.g., APV, Rannie, Gaulin). A glucosyltransferase enzyme is typically soluble in these types of preparations. A bacterial cell lysate, extract, or homogenate herein may be used at about 0.15-0.3% (v/v), for example, in a reaction solution for producing branched alpha-glucan.

The activity of a glucosyltransferase enzyme herein can be determined using any method known in the art. For example, glucosyltransferase enzyme activity can be determined by measuring the production of reducing sugars (fructose and glucose) in a reaction solution containing sucrose (50 g/L), dextran T10 (1 mg/mL) and potassium phosphate buffer (pH 6.5, 50 mM), where the solution is held at 22-25° C. for 24-30 hours. The reducing sugars can be measured, for instance, by adding 0.01 mL of the reaction solution to a mixture containing 1 N NaOH and 0.1% triphenyltetrazolium chloride and then monitoring the increase in absorbance at $OD_{480\ nm}$ for five minutes.

The temperature of an enzymatic reaction herein can be controlled, if desired. In certain embodiments, the temperature of the reaction can be between about 5° C. to about 50° C. The temperature in certain other embodiments can be between about 20° C. to about 40° C., or about 20° C. to about 30° C. (e.g., about 22-25° C.).

The initial concentration of sucrose in a reaction solution herein can be about 20 g/L to about 400 g/L, for example. Alternatively, the initial concentration of sucrose can be about 75 g/L to about 175 g/L, or from about 50 g/L to about 150 g/L. Alternatively still, the initial concentration of sucrose can be about 40, 50, 60, 70, 80, 90, 100, 110, 120, 130, 140, 150, or 160 g/L (or any integer value between 40 and 160 g/L), for example. "Initial concentration of sucrose" refers to the sucrose concentration in a glucosyltransferase reaction just after all the reaction components have been added (e.g., at least water, sucrose, dextran, glucosyltransferase enzyme).

Sucrose used in an enzymatic reaction herein can be highly pure (≥ 99.5%) or be of any other purity or grade. For example, sucrose can have a purity of at least 99.0%, or can be reagent grade sucrose. As another example, incompletely refined sucrose can be used. Incompletely refined sucrose herein refers to sucrose that has not been processed to white refined sucrose. Thus, incompletely refined sucrose can be completely unrefined or partially refined. Examples of unrefined sucrose are "raw sucrose" ("raw sugar") and solutions thereof. Examples of partially refined sucrose have not gone through one, two, three, or more crystallization steps. The ICUMSA (International Commission for Uniform Methods of Sugar Analysis) of incompletely refined sucrose herein can be greater than 150, for example. Sucrose herein may be derived from any renewable sugar source such as sugar cane, sugar beets, cassava, sweet sorghum, or corn. Suitable forms of sucrose useful herein are crystalline form or non-crystalline form (e.g., syrup, cane juice, beet juice), for example.

Methods of determining ICUMSA values for sucrose are well known in the art and disclosed by the International Commission for Uniform Methods of Sugar Analysis in *ICUMSA Methods of Sugar Analysis: Official and Tentative Methods Recommended by the International Commission for Uniform Methods of Sugar Analysis (ICUMSA)* (Ed. H. C. S. de Whalley, Elsevier Pub. Co., 1964), for example, which is incorporated herein by reference. ICUMSA can be measured, for example, by ICUMSA Method GS1/3-7 as described by R. J. McCowage, R. M. Urquhart and M. L. Burge (*Determination of the Solution Colour of Raw Sugars, Brown Sugars and Coloured Syrups at pH 7.0-Official*, Verlag Dr. Albert Bartens, 2011 revision), which is incorporated herein by reference.

The pH of an enzymatic reaction in certain embodiments can be between about 4.0 to about 8.0, or between about 5.0 to about 6.0. Alternatively, the pH can be about 4.0, 4.5, 5.0, 5.5, 6.0, 6.5, 7.0, 7.5, or 8.0, for example. The pH can be adjusted or controlled by the addition or incorporation of a suitable buffer, including but not limited to: phosphate, tris, citrate, or a combination thereof. Buffer concentration in a glucan synthesis reaction can be from 0 mM to about 100 mM, or about 10, 20, or 50 mM, for example.

One or more different glucosyltransferase enzymes may be used in certain aspects. An enzymatic reaction herein may contain one, two, or more glucosyltransferase enzymes, for example.

The present disclosure also concerns a method of preparing a dextran-poly alpha-1,3-glucan graft copolymer, the method comprising:

(a) contacting at least (i) water, (ii) sucrose, (iii) dextran with a weight-average molecular weight (Mw) of at least about 100000 Daltons, and (iv) a glucosyltransferase enzyme that synthesizes poly alpha-1,3-glucan comprising at least about 95% alpha-1,3-glucosidic linkages, whereby a dextran-poly alpha-1,3-glucan graft copolymer is produced; and (b) optionally, isolating the dextran-poly alpha-1,3-glucan graft copolymer produced in step (a). Step (a) in such a method typically entails preparation of an enzymatic reaction comprising each of components (i)-(iv). Any of the above enzymatic reaction conditions, and/or those disclosed in the below Examples, can characterize step (a). Also, any of the following conditions of this method can optionally characterize an enzymatic reaction herein.

A graft copolymer synthesis method as presently disclosed comprises contacting at least water, sucrose, and certain dextran and glucosyltransferase enzyme components with each other. These and optionally other reagents can be added all together or added in any order as discussed below. While step (a) typically begins with formation of a reaction solution, it would be understood that this solution becomes a mixture after synthesis of insoluble graft copolymer product. The contacting step herein can be performed in any number of ways. For example, the desired amount of sucrose and/or dextran can first be dissolved in water (optionally, other components may also be added at this stage of preparation, such as buffer components), followed by addition of glucosyltransferase enzyme. A reaction thus prepared may be kept still, or agitated via stirring or orbital shaking, for example. Typically, an enzymatic reaction herein is cell-free.

Completion of a reaction in certain embodiments can be determined visually (e.g., no more accumulation of insoluble product) and/or by measuring the amount of sucrose left in the solution (residual sucrose), where a percent sucrose consumption of over about 90% can indicate reaction completion, for example. Typically, a reaction of the disclosed process can take about 12, 24, 36, 48, 60, 72, 84, or 96 hours to complete, which may depend on certain parameters such as the amount of sucrose and/or glucosyltransferase enzyme used in the reaction. In some embodiments, reaction time can be 1, 2, 3, 4, or 5 hours.

In certain embodiments of a graft copolymer synthesis method, further present in contacting step (a) is dextran with a weight-average molecular weight less than about 60000 Daltons, wherein the dextran with a weight-average molecular weight of at least about 100000 Daltons (e.g., any higher Mw as disclosed above) is preferentially used as a substrate for side chain synthesis by the glucosyltransferase enzyme. Thus, in certain cases in which a heterogeneous dextran substrate (e.g., PDI over 4, or PDI of 4-15) is used in which there are various dextran species and the Mw range of these species spans from less than 60000 Daltons (or less than 90000, 80000, 70000, 50000, or 40000 Daltons, for example) to more than 100000 Daltons, the distribution of graft copolymer products will skew higher towards those with a dextran component of 100000 Daltons or more. For example, it is believed that at least about 75%, 76%, 77%, 78%, 79%, 80%, 81%, 82%, 83%, 84%, 85%, 86%, 87%, 88%, 89%, 90%, 91%, 92%, 93%, 94%, or 95% by weight of the graft copolymer products comprise a dextran component with a Mw of at least 100000 Daltons.

Such method embodiments can optionally be characterized as a method of partitioning, fractionating, or separating higher Mw dextran from lower Mw dextran. While higher Mw dextran is partitioned to insoluble graft copolymer, lower Mw dextran remains in the solution phase of a glucosyltransferase reaction herein. In some embodiments, the reaction time for this partitioning effect to occur is at least about 12, 15, 18, 21, or 24 hours. The Mw of dextran that partitions to insoluble graft copolymer product in some instances is about 100000 or 150000 to about 200000, 250000, 500000, 750000, or 1000000 Daltons.

In certain embodiments, the PDI of a dextran-poly alpha-1,3-glucan graft copolymer can be controlled in a graft copolymer synthesis method by modulating the amount of dextran substrate entered into an enzymatic reaction (e.g., refer to Table 7). In general, increasing the level of starting dextran in an enzymatic reaction herein leads to production of graft copolymer with a lower PDI, and vice versa. For example, a reduction in product PDI by about, or at least about, 5%, 10%, 20%, 25%, 30%, 40%, 50%, 60%, or 65% can be achieved if the initial concentration of dextran in an enzymatic reaction is increased by about, or at least about, 30%, 40%, 50%, 60%, 70%, 80%, 90%, 100%, 150%, 200%, 250%, 500%, 750%, or 1000%.

Figure 3:
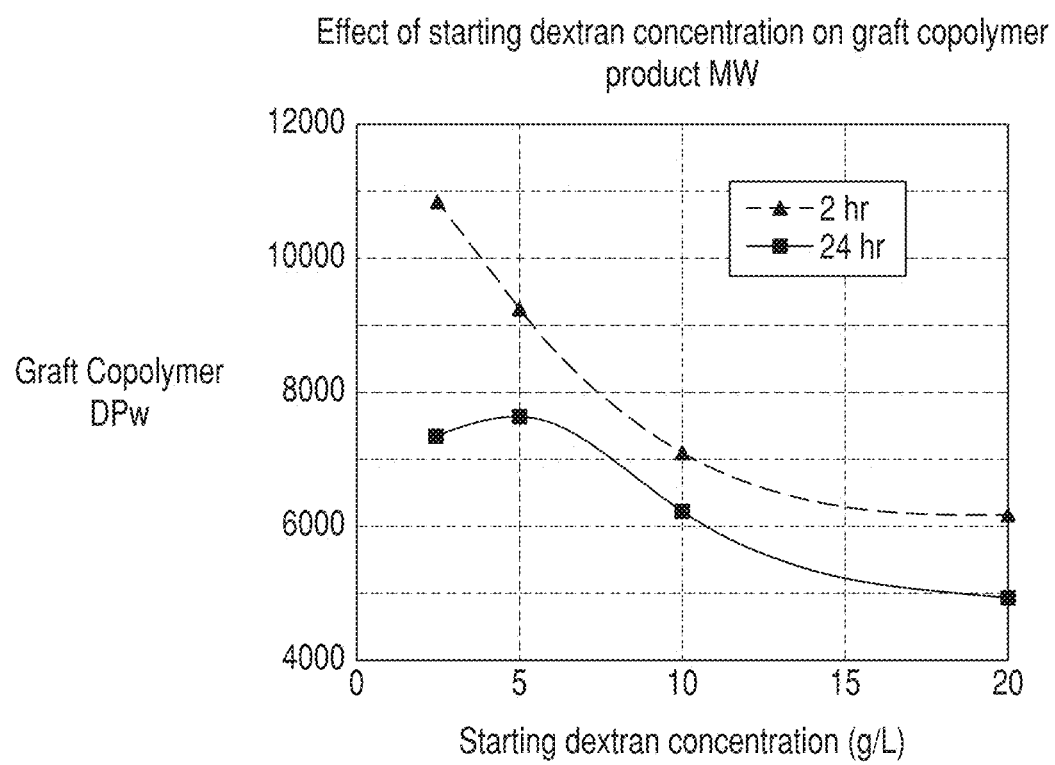

In certain embodiments, the Mw of a dextran-poly alpha-1,3-glucan graft copolymer can be controlled in a graft copolymer synthesis method by modulating the amount of dextran substrate entered into an enzymatic reaction (e.g., refer to Table 7 and FIG. 3). In general, increasing the level of starting dextran in an enzymatic reaction herein leads to production of graft copolymer with a lower Mw, and vice versa. For example, a reduction in product Mw by about, or at least about, 5%, 10%, 20%, 25%, 30%, 40%, or 50% can be achieved if the initial concentration of dextran in an enzymatic reaction is increased by about, or at least about, 30%, 40%, 50%, 60%, 70%, 80%, 90%, 100%, 150%, 200%, 250%, 500%, 750%, or 1000%.

Dextran-poly alpha-1,3-glucan graft copolymer produced in the disclosed synthesis method can optionally be isolated. For example, insoluble graft copolymer can be separated by filtration or centrifugation. In doing so, the graft copolymer is separated from most of the reaction solution, which may comprise water, fructose and certain byproducts (e.g., leucrose, soluble oligosaccharides DP2-DP7, glucose). This solution may also comprise residual sucrose (i.e., unreacted sucrose). Isolation can optionally further comprise washing a graft copolymer product one, two, or more times with water or other aqueous liquid, and/or drying the product. Such washing can use wash volumes of about, or at least about, 0.5-, 1-, 1.5-, or 2-times the volume of the original reaction or of a product sample, and/or involve filtration and/or centrifugation. Washing in some aspects such as filtration can be via displacement washing, in which a wash is passed through a product without agitation and/or any force applied.

In some embodiments (an "enhanced filtration method"), the dextran entered into step (a) of a graft copolymer synthesis method has a weight-average molecular weight of at least about 50 million Daltons and an initial concentration of at least about 2 g/L. The dextran-poly alpha-1,3-glucan graft copolymer produced in step (a) in such embodiments is isolated using a filtration step. The graft copolymer product in these embodiments has a higher filtration rate compared to the filtration rate of a poly alpha-1,3-glucan homopolymer or other control material. The Mw of dextran of this enhanced filtration method can be about 50 million Daltons (or any greater Mw as disclosed herein), and/or the initial dextran concentration in the enzymatic reaction can be about 2 g/L (or any greater concentration as disclosed herein). Enhanced filterability herein can optionally refer to the ease by which water and/or an aqueous solution (e.g. liquid portion from step [a]) can be filtered (e.g., gravity only, displacement washing, applied force) through a bed (e.g., wet cake) of insoluble graft copolymer product.

A graft copolymer product in an enhanced filtration method herein has a higher filtration rate compared to the filtration rate of a poly alpha-1,3-glucan homopolymer or other control material. For example, a graft copolymer herein can exhibit filterability that is at least about 10%, 20%, 30%, 40%, 50%, 60%, 70%, 80%, 90%, 100%, 150%, 200%, 500%, 1000%, 10000%, or 100000% faster than the filterability of poly alpha-1,3-glucan homopolymer or other control material, under otherwise same or similar filtration conditions (e.g., wet cake thickness, filtration apparatus). Filterability measurements for making such a comparison can be in units of cake resistance or any other filterability measure. Cake resistance (filter cake resistance) can be measured according to Earle, R L (*Unit Operations in Food Processing* [Chapter 10: Mechanical Separations], Web Edition, 2004, Pergamon Commonwealth and International Library) or Teoh et al. (*Chem. Eng. Sci.* 61:4957-4965), for example, which are both incorporated herein by reference. A poly alpha-1,3-glucan homopolymer in these embodiments can be about 500, 600, 700, 800, 900, or 1000 DPw, and have at least 95%, 96%, 97%, 98%, 99% or 100% alpha-1,3-linkages, for example. Another control material can be a graft copolymer herein having the same type of dextran used in the enhanced filtration method, but at a content of less than about 1.6%, 1.5%, 1.4%, 1.3%, 1.2%, 1.1%, 1.0%, 0.9%, or 0.8% by weight of the graft copolymer.

A graft copolymer product in an enhanced filtration method herein can comprise about, or at least about, 2 wt % of dextran in some embodiments. For example, such a graft copolymer may comprise 2%-50%, 2%-11%, or 2.5%-10.5% dextran by weight of the copolymer. In some instances, a graft copolymer product can appear as particles with an average diameter of about 3.5, 3.75, 4.0, 4.25, 4.5, 4.75, 5.0, 5.25, or 5.5 mm, for example. The enhanced filterability of graft copolymers in certain aspects herein represents an advantage with respect to poly alpha-1,3-glucan homopolymer, which typically is difficult to filter.

Non-limiting examples of compositions and methods disclosed herein include:
1. A composition comprising a graft copolymer that comprises:
   (i) a backbone comprising dextran with a weight-average molecular weight (Mw) of at least about 100000 Daltons, and
   (ii) poly alpha-1,3-glucan side chains comprising at least about 95% alpha-1,3-glucosidic linkages.
2. The composition of embodiment 1, wherein the poly alpha-1,3-glucan side chains comprise at least about 99% alpha-1,3-glucosidic linkages.
3. The composition of embodiment 1 or 2, wherein the individual Mw of one or more poly alpha-1,3-glucan side chains is at least about 100000 Daltons.
4. The composition of embodiment 1, 2, or 3, wherein the graft copolymer is insoluble under aqueous conditions.
5. The composition of embodiment 1, 2, 3, or 4, wherein the dextran comprises:
   (i) about 87-93 wt % glucose linked at positions 1 and 6;
   (ii) about 0.1-1.2 wt % glucose linked at positions 1 and 3;
   (iii) about 0.1-0.7 wt % glucose linked at positions 1 and 4;
   (iv) about 7.7-8.6 wt % glucose linked at positions 1, 3 and 6; and
   (v) about 0.4-1.7 wt % glucose linked at:
      (a) positions 1, 2 and 6, or (b) positions 1, 4 and 6;
   wherein the Mw of the dextran is about 50-200 million Daltons.
6. The composition of embodiment 5, wherein the Mw of the dextran is at least about 100 million Daltons.
7. The composition of embodiment 5 or 6, wherein the dextran is a product of a glucosyltransferase enzyme comprising an amino acid sequence that is at least 90% identical to SEQ ID NO:6 or SEQ ID NO:7.
8. The composition of embodiment 5, 6, or 7, wherein the graft copolymer comprises at least about 2.0 wt % dextran.
9. The composition of embodiment 1, 2, 3, 4, 5, 6, 7, or 8, wherein the graft polymer has a water retention value (WRV) of at least about 100.
10. The composition of embodiment 1, 2, 3, 4, 5, 6, 7, 8, or 9, wherein the composition is a personal care product, household product, medical product, or industrial product.
11. An enzymatic reaction comprising (i) water, (ii) sucrose, (iii) dextran with a weight-average molecular weight (Mw) of at least about 100000 Daltons, and (iv) a glucosyltransferase enzyme that synthesizes poly alpha-1,3-glucan comprising at least about 95% alpha-1,3-glucosidic linkages,
   wherein the enzymatic reaction produces a graft copolymer according to the composition of embodiment 1, 2, 3, 4, 5, 6, 7, 8, or 9.
12. The enzymatic reaction of embodiment 11, wherein the initial concentration of the dextran in the reaction is at least about 2 g/L, and wherein the Mw of the dextran is at least about 50 million Daltons.
13. A method of preparing a graft copolymer, the method comprising:
   (a) contacting at least (i) water, (ii) sucrose, (iii) dextran with a weight-average molecular weight (Mw) of at least about 100000 Daltons, and (iv) a glucosyltransferase enzyme that synthesizes poly alpha-1,3-glucan comprising at least about 95% alpha-1,3-glucosidic linkages, whereby a graft copolymer according to the composition of embodiment 1, 2, 3, 4, 5, 6, 7, 8, or 9 is produced; and
   (b) optionally, isolating the graft copolymer produced in step (a).
14. The method of embodiment 13, wherein further present in contacting step (a) is dextran with an Mw less than about 60000 Daltons, wherein the dextran with an Mw of at least about 100000 Daltons is preferentially used as a substrate for side chain synthesis by the glucosyltransferase enzyme.
15. The method of embodiment 13 or 14, wherein the dextran entered into step (a) has an Mw of at least about 50 million Daltons and an initial concentration of at least about 2 g/L, wherein the graft copolymer produced in step (a) is isolated, and wherein the isolation step comprises a filtration step, wherein the graft copolymer has a higher filtration rate compared to the filtration rate of a poly alpha-1,3-glucan homopolymer.

EXAMPLES

The present disclosure is further exemplified in Examples 1-3 and 5-8. It should be understood that these Examples, while indicating certain preferred aspects herein, are given by way of illustration only. From the above discussion and these Examples, one skilled in the art can ascertain the essential characteristics of the disclosed embodiments, and without departing from the spirit and scope thereof, can make various changes and modifications to adapt the disclosed embodiments to various uses and conditions.

Example 1

Poly Alpha-1,3-Glucan Synthesis from High Molecular Weight Dextran Primer

This Example describes synthesis of poly alpha-1,3-glucan with a glucosyltransferase enzyme using commercially available dextran with high weight-average molecular weight (average 150 kDa) as a primer. Graft copolymers comprising a dextran backbone and poly alpha-1,3-glucan side chains were produced.

Two separate poly alpha-1,3-glucan polymerizations were performed with reactions (A and B) comprising water, sucrose (~100 g/L), dextran, and a *Streptococcus salivarius*-based glucosyltransferase enzyme that synthesizes poly alpha-1,3-glucan with all or nearly all alpha-1,3-glucosidic linkages. Examples of glucosyltransferases that be used in such reactions include those disclosed in U.S. Patent Appl. Publ. No. 2014/0087431, which is incorporated herein by reference.

Each of reactions A and B was prepared by mixing 940 g DI (deionized) water, 100 g sucrose (OmniPur Calbiochem 8550; Lot VF20C; FW 342.30), and 1.36 g potassium monophosphate (MW 136.09; Sigma P5379). The pH was measured to be 5.6 using a conductivity meter, and adjusted down to 5.54 using a few drops of 1N $H_2SO_4$. A 1-mL sample was taken for HPLC time point zero (pre-addition of dextran). Then, 5 g and 10 g of 150-kDa (avg) dextran (Sigma D4876) were added to reactions A and B, respectively. 500-mL of each reaction was loaded into individual flasks.

After mixing each reaction at about 190 RPM to dissolve the added dextran, 1-mL HPLC samples were taken from each reaction for time point zero (post-addition of dextran) analysis. Each reaction was placed into a circulating heater/chiller set to 25° C. and stirring was commenced at 150 rpm.

The reactions were allowed to come up to temperature (~24.4° C.). and stirred for about 45 min before enzyme addition. 50 U of glucosyltransferase enzyme was then added to each reaction.

Filtrate samples (i.e., liquid separated from insoluble products) (1 mL) from each of reactions A and B were taken for HPLC at 2 hr and at the end of each reaction (24 hr). The samples were deactivated for HPLC by heat quenching at 90° C. for 10 min. The samples were filtered through 0.45-μm PTFE filters and diluted for HPLC analysis.

Two identical dilutions were made for all of the time-point filtrate samples, with the exception of the 2-hr and 24-hr samples of reaction B. Samples A 2-hr, B 2-hr, and B 24-hr were all very difficult to filter through the 0.45-μm PTFE filters. All the samples were run in duplicate in various HPLC columns.

A whole-reaction sample (50-ml) was taken at 2 hr from each of reactions A and B and suction-filtered as dry as possible through a plastic-disposable filter. Before washing the insoluble products twice with 50 mL of hot water, the filtrate was removed and saved separately. The insoluble polymer samples were saved in glass vials and stored at 10° C. before analyzing by size-exclusion chromatography (SEC) to determine apparent DP (degree of polymerization), true DP, apparent IV (inherent viscosity), and true IV. Excess insoluble polymer from each 2-hr sample was dried in a vacuum oven at 60° C. under nitrogen for 3 days, and weighed to determine percent solids.

Pulling the filtrate from the synthesized polymer with suction took longer than expected, and was likely related to the continued production of insoluble polymer in the filtrate, which still contained sucrose and glucosyltransferase enzyme. Once the filtrate was all collected, a 1-mL sample was taken and deactivated for HPLC (see above), while the remainder was deactivated in a 70-80° C. water bath for 15 minutes, allowed to cool, and then filtered to remove insoluble polymer products.

The filtrate was then placed in dialysis tubing (14 kDa molecular weight cut-off [MWCO]) and dialyzed for 2 days in running water to remove monosaccharides (fructose, glucose) and oligomers (DP 2-7). Some minor solids were formed during dialysis, so the contents were first filtered and then rotary-evaporated (rotovapped) to a liquid concentrate, which was frozen in liquid nitrogen. The frozen concentrate was then lyophilized for 2-3 days, after which the dry solids were weighed analyzed by SEC.

After 24 hr, the polymer product slurries created in each of reactions A and B were suction-filtered. Each filtrate was saved separately and an HPLC sample was taken. The polymer was washed twice with 500 ml distilled water (room temperature), after which gross water was sucked off leaving a wet cake. The wet cake was weighed and a sample thereof was taken for SEC analysis. A wet cake sample (~5-6 g) was oven-dried (60° C. for 3 days) and the total insoluble polymer product yield was calculated based on initial wet cake weight. The remaining polymer wet cake was frozen for later analysis. The remaining filtrate was deactivated in a 90° C. water bath for 15 min and dialyzed for 2 days in running water as above. The dialysate was filtered, rotovapped to ~80 mL, lyophilized, weighed and submitted for SEC. Per HPLC analysis, monosaccharide and oligomer (DP 2-7) generation was normal and similar between polymerizations A and B. Wet cake samples were dissolved for SEC analysis by shaking in DMSO/2% LiCl for 10 min at room temperature.

Various aspects of the filtrates and insoluble products of reactions A and B are provided in Tables 1-4 below.

TABLE 1

Total Solids Present in Filtrate
Lyophilized Filtrate Solids*

| Reaction | 2 hr | 24 hr |
|---|---|---|
| A | 0.27 g | 3.13 g |
| B | 0.37 g | 4.75 g |

*includes oligomers

TABLE 2

Sucrose and Dextran Conversion

| Reaction | Sucrose Conversion | Dextran Conversion |
|---|---|---|
| A | 99.3% | 73% |
| B | 99.3% | 64% |

TABLE 3

Dextran Recovered in Filtrate
Recovered Dextran

| Reaction/Time point | Mn | Mw | DPw | Mz | Mw/Mn |
|---|---|---|---|---|---|
| A/2 hr | 15196 | 212556 | 1312 | 2644592 | 13.99 |
| A/24 hr | 10195 | 30003 | 185 | 72429 | 2.94 |
| B/2 hr | 15541 | 190473 | 1176 | 1921736 | 12.26 |
| B/24 hr | 11340 | 45326 | 280 | 137362 | 4.00 |
| starting dextran | 20120 | 244127 | 1507 | 1260514 | 12.13 |

TABLE 4

Molecular Weight Profile of Dextran-Poly
Alpha-1,3-Glucan Copolymer Products

| | Dextran-Poly Alpha-1,3-Glucan Copolymer | | | | |
|---|---|---|---|---|---|
| Reaction/ Time point | Mn (kDa) | Mw (kDa) | DPw | Mz (kDa) | Mw/Mn |
| A/2 hr | 525 | 1156 | 7137 | 1942 | 2.2 |
| A/24 hr | 322 | 1011 | 6244 | 2126 | 3.14 |
| B/2 hr | 465 | 1005 | 6202 | 1765 | 2.16 |
| B/24 hr | 285 | 802 | 4948 | 1764 | 2.81 |

Figure 2:
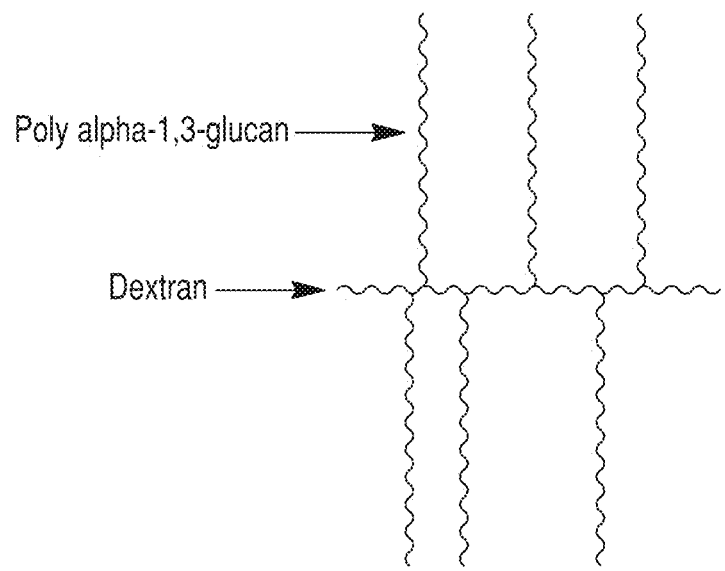

SEC analysis of the starting dextran used in each reaction showed that it was branched. It was estimated that there was a pendant glucose branching from the starting dextran about every 20 monomeric units of the dextran. Each polymerization reaction (24 hr) gave a water-insoluble polymer with a high DPw: ~ 6000 for reaction A (10 g/L dextran loading) and ~5000 for reaction B (20 g/L dextran loading) (Table 4). Poly alpha-1,3-glucan chains grew off of the dextran branch points, forming a graft copolymer (refer to FIGS. 1 and 2).

Dextranase degradation analyses indicated that the poly alpha-1,3-glucan side chains each had a DPw of roughly 1000. Briefly, dextranase assays were conducted by individually reacting dextran-poly alpha-1,3-glucan graft copolymer products with dextranase in a buffered reaction (pH 5.3-5.7, room temperature, nutation) for about 4 days.

Thus, considering that the starting dextran had a measured DPw of about 1500 (Table 3), and each side chain was about 1000 DPw, there may have been on average about 4-5 poly alpha-1,3-glucan chains on each dextran. Based on this observation, it appears that only a small fraction of the pendant glucose units of the dextran served to prime poly alpha-1,3-glucan side chain synthesis (i.e., there were likely only about 4-5 side chains, whereas it might have been possible to have had about 75 side chains given the presence of a pendant glucose group every 20 monomeric units of the dextran [DPw 1507 divided by 20]).

The molecular weight of dextran recovered in filtrate samples of 24-hr reactions was low, in comparison to the starting dextran molecular weight (Table 3). While one hypothesis was that the dextran may have been degraded by the glucosyltransferase enzyme in the reaction, this was found not to be the case (see Example 3). Thus, it was likely that the dextran was effectively fractionated during the reaction, with higher molecular weight dextran preferentially being used as a substrate for priming poly alpha-1,3-glucan side chain synthesis. Following this scenario, the larger dextran molecules used to prime synthesis of insoluble graft copolymer would have been removed from the soluble pool, leaving behind smaller dextran molecules in reaction filtrates. This observation is intriguing, especially given that other work (WO15/119859) suggested that dextran molecular weight does not play a role in dextran priming of 1,3-glucosidic link-comprising glucan synthesis by glucosyltransferase enzymes.

Thus, graft copolymers comprising a dextran backbone and poly alpha-1,3-glucan side chains were produced. It is potentially of interest that there were relatively few side chains (4-5), considering that, theoretically, there could have been at least 10-15 times more side chains synthesized. Also, in reactions for preparing this graft copolymer, it appears that high molecular weight dextran, as opposed to lower molecular weight dextran, is preferentially used as a substrate by glucosyltransferases that synthesize glucan comprising mostly alpha-1,3-glucosidic linkages.

Example 2

Controlling the Molecular Weight and Polydispersity of Dextran-Poly Alpha-1,3-Glucan Graft Copolymer Products of a Glucosyltransferase Enzyme Reaction This Example is in addition to Example 1, which together demonstrate, for example, that the molecular weight and polydispersity of dextran-poly alpha-1,3-glucan graft copolymer product can be controlled by modifying the concentration of dextran entered into a glucosyltransferase enzyme reaction.

In general, except as noted below, the procedures described in Example 1 were applied to synthesize and analyzed dextran-poly alpha-1,3-glucan copolymers.

Briefly, two 500-mL glucan synthesis reactions were run at about 25° C. with 100 g/L sucrose and 100 U/L of an *S. salivarius*-based glucosyltransferase enzyme that synthesizes poly alpha-1,3-glucan with all or nearly all alpha-1,3-glucosidic linkages with stirring at 150 rpm. To set up these reactions, 100 g of sucrose (OmniPur Calbiochem 8550) and 1.36 g of potassium monophosphate (Sigma P5379) were dissolved in 940 g tap water and adjusted to pH 5.5 with NaOH. A 1-mL sample (t=0) was taken for HPLC analysis after which the solution was divided in two 500-mL portions. Flasks for reactions A and B were each charged with 500 mL of the sucrose solution and 1.25 g or 2.5 g, respectively, of 150-kDa (avg) dextran (Sigma D4876). HPLC (t=0) samples were taken after which the glucosyltransferase enzyme was added.

At 2 hr post enzyme addition, 50-mL samples (reaction solution and insoluble product) were taken from each of reactions A and B and suction-filtered. The filtrates were saved; 1 mL of each filtrate was removed for HPLC (t=2 hr).

The insoluble polymer products were washed twice with 50 mL hot water and analyzed by SEC. The filtrates were deactivated in an 80° C. water bath for 15 min, refiltered and dialyzed (14 kDa MWCO) for 18 days in running water to remove monosaccharides (fructose, glucose) and oligomers (DP 2-7).

At 24 hr post enzyme addition, the polymer product slurries created in each of reactions A and B were heated to 65° C. in a circulating bath and stirred for 1 hr to deactivate the enzyme. The slurries were then suction-filtered; each filtrate was saved and a 1-mL sample (t=24 hr) was taken for HPLC analysis. The polymer was washed, after which gross water was sucked off leaving a wet cake. The wet cake was weighed and a sample thereof was taken for SEC analysis. A wet cake sample was oven-dried (60° C. for 3 days) and the total insoluble polymer product yield was calculated based on initial wet cake weight. The remaining polymer wet cake was frozen for later analysis. The filtrate was dialyzed for 17 days in running water as above. The dialysate was filtered, rotovapped to ~80 mL, lyophilized, weighed and submitted for SEC. Per HPLC analysis, monosaccharide and oligomer (DP 2-7) generation was normal and similar between polymerizations A and B.

Various aspects of the filtrates and insoluble products of reactions A and B of this Example are provided in Tables 5-7 below.

TABLE 5

Total Solids Present in Filtrate
Lyophilized Filtrate Solids*

| Reaction | 2 hr | 24 hr |
|---|---|---|
| A | 0.057 g | 0.086 g |
| B | 0.099 g | 0.322 g |

*monosaccharides and oligomers removed

TABLE 6

Sucrose and Dextran Conversion

| Reaction | Sucrose Conversion | Mass Balance | Dextran Conversion |
|---|---|---|---|
| A | 99.3% | 98.2% | 92% |
| B | 99.4% | 99.0% | 86% |

TABLE 7

Molecular Weight Profile of Dextran-Poly Alpha-1,3-Glucan Copolymer Products

| Reaction | Time point | Starting Dextran Concentration | Dextran-Poly Alpha-1,3-Glucan Copolymer | | | | |
|---|---|---|---|---|---|---|---|
| | | | Mn (kDa) | Mw (kDa) | DPw | Mz (kDa) | Mw/Mn |
| A (Example 2) | 24 hr | 2.5 g/L | 261 | 1198 | 7394 | 2520 | 4.59 |
| B (Example 2) | 24 hr | 5 g/L | 301 | 1236 | 7629 | 2518 | 4.10 |
| A (Example 1) | 24 hr | 10 g/L | 322 | 1011 | 6244 | 2126 | 3.14 |
| B (Example 1) | 24 hr | 20 g/L | 285 | 802 | 4948 | 1764 | 2.81 |
| A (Example 2) | 2 hr | 2.5 g/L | 177 | 1762 | 10873 | 2814 | 9.96 |
| B (Example 2) | 2 hr | 5 g/L | 259 | 1499 | 9255 | 2555 | 5.78 |
| A (Example 1) | 2 hr | 10 g/L | 525 | 1156 | 7137 | 1942 | 2.2 |
| B (Example 1) | 2 hr | 20 g/L | 465 | 1005 | 6202 | 1765 | 2.16 |

Each polymerization reaction after 24 hr in this Example produced water-insoluble polymer with a high DPw of about 7500 (Table 7). The polydispersities (Mw/Mn) of the insoluble polymer products were relatively high, especially for reactions with less starting dextran, (Table 7), suggesting there is poly alpha-1,3-glucan homopolymer present in the insoluble products in addition to dextran-poly alpha-1,3-glucan graft copolymer. Such a result was to be expected in a system starved for dextran; indeed, reactions with higher amounts of starting dextran (Example 1) yielded products with lower polydispersity (Table 7). It thus appears that the polydispersity of a dextran-poly alpha-1,3-glucan graft copolymer produced herein can be controlled as a function of the level of dextran entered into a glucosyltransferase reaction.

FIG. 3 shows, for 24 hr reactions in which most of the starting dextran has been consumed, the relationship between starting dextran concentration and DPw of the dextran-poly alpha-1,3-glucan graft copolymer product formed. Homopolymerization of poly alpha-1,3-glucan alone competes with dextran priming at low dextran concentrations, while each of the dextran chains gets fewer glucan grafts at higher dextran concentrations. The maximum graft copolymer molecular weight, appears to be produced when using 5 g/L dextran (FIG. 3, Table 7) in a reaction having 100 g/L sucrose and 100 U/L glucosyltransferase enzyme. It thus appears that the molecular weight of a dextran-poly alpha-1,3-glucan graft copolymer produced herein can be controlled as a function of the level of dextran entered into a glucosyltransferase reaction.

Thus, graft copolymers comprising a dextran backbone and poly alpha-1,3-glucan side chains were produced. Also, the molecular weight and polydispersity of dextran-poly alpha-1,3-glucan copolymer products can be controlled by modifying the concentration of dextran entered into a glucosyltransferase enzyme reaction.

Example 3

Glucosyltransferase Enzyme Activity Does Not Degrade Dextran

This Example demonstrates that the glucosyltransferase used in Examples 1 and 2 to synthesize dextran-poly alpha-1,3-glucan graft copolymer does not degrade dextran. Therefore, the apparent dextran partitioning effect observed in the above reactions was not due to dextran degradation from glucosyltransferase activity.

As described in Example 1, when poly alpha-1,3-glucan synthesis with a glucosyltransferase enzyme is primed with dextran, the recovered unreacted dextran has a significantly lower molecular weight than the dextran which was initially used in the reaction. It was not known whether the dextran was effectively fractionated in the glucosyltransferase reaction—preferentially reacting larger dextran chains to form insoluble dextran-poly alpha-1,3-glucan copolymer, leaving smaller unreacted dextran chains in the reaction solution—or whether the glucosyltransferase enzyme was capable of degrading the dextran.

The purpose of this experiment was to examine if exposing dextran to the glucosyltransferase enzyme used in Examples 1 and 2 under normal reaction conditions, but without sucrose, would lead to dextran degradation. 2.5 g of 150-kDa (avg) dextran (Sigma D4876) and 0.68 g of potassium monophosphate (Sigma P5379) were dissolved in 490 g tap water to provide a solution at pH 5.59. This solution was stirred at 25° C. in a reactor after which 50 U of the glucosyltransferase enzyme was added. The solution was then stirred at 150 rpm for 24 hr and then rotovapped from a hot water bath to leave a damp solid. The solid was taken up in 20 mL of distilled water and the resulting hazy solution was clarified by suction-filtration; a very small amount (~0.1 g) of light brown solids was removed. The filtrate was lyophilized to recover 2.87 g dextran, which was analyzed by SEC and compared with the starting dextran (Table 8).

TABLE 8

Analysis of Dextran Molecular Weight Before and After Exposure to Glucosyltransferase Enzyme

| Dextran | Mn (kDa) | Mp (kDa) | Mw (kDa) | Mz (kDa) | Mw/Mn | DPw |
|---|---|---|---|---|---|---|
| Starting | 60.07 | 83.6 | 258 | 1221 | 4.29 | 1593 |
| Recovered | 58.01 | 83.6 | 249 | 1255 | 4.30 | 1537 |

The results in Table 8 show that the glucosyltransferase enzyme does not degrade dextran under the reaction conditions employed in Examples 1 and 2 (but without sucrose). This result indicates that the enzymatic process of poly alpha-1,3-glucan grafting onto dextran effectively acts to fractionate the dextran based on molecular weight as described above.

Example 4

Poly Alpha-1,3-Glucan Synthesis from Lower Molecular Weight Dextran (Comparative)

This Example describes synthesis of poly alpha-1,3-glucan with a glucosyltransferase enzyme using commercially available dextran primer with a weight-average molecular weight of about 40 kDa.

The purpose of this experiment was to synthesize a dextran-poly alpha-1,3-glucan graft copolymer using dextran having a lower molecular weight than the dextran used in Examples 1 and 2. The dextran used in this experiment has a molecular weight of about 35-45 kDa, which is roughly four times less than the molecular weight of the dextran employed in Examples 1 and 2.

A 1000-mL poly alpha-1,3-glucan polymerization reaction was performed as follows. Sucrose (100 g; OmniPur Calbiochem 8550), dextran (10 g, 35-45 kDa, DPw=220-280, Sigma D1662) and potassium monophosphate (1.36 g, Sigma P5379) were dissolved in 940 g of tap water to give pH 5.67. Stirring at 25° C./150 rpm was then commenced after which 100 U of the glucosyltransferase used in the above Examples was added; stirring at 25° C./150 rpm was continued for 24 hr. After 1.5 hr, a 50-mL insoluble product sample was suction-filtered, washed and suctioned to a damp wet cake (8.7 g) and submitted for SEC analysis. At 24 hr, the insoluble product slurry was suction-filtered and washed three times with 500 mL hot tap water. The gross water was suction-removed and the wet cake was weighed (480 g). Wet cake samples were taken for SEC analysis and percent solids determination (7.6 wt %), the latter of which was done by oven-drying (60° C. for 3 days). The total insoluble dextran-poly alpha-1,3-glucan product yield was calculated based on initial wet cake weight and percent solids. The molecular weight profile of each insoluble product at 1.5 hr and 12 hr was determined (Table 9).

TABLE 9

Molecular Weight Profile of Dextran-Poly Alpha-1,3-Glucan Copolymer Products

| | Dextran-Poly Alpha-1,3-Glucan Copolymer | | | | | |
|---|---|---|---|---|---|---|
| Time point | Mn (kDa) | Mp (kDa) | Mw (kDa) | DPw | Mz (kDa) | Mw/Mn |
| 1.5 hr | 359 | 478 | 593 | 3660 | 946 | 1.65 |
| 24 hr | 210 | 365 | 474 | 2926 | 836 | 2.26 |

Based on measured DPw, it appears that two or at most three poly alpha-1,3-glucan side chains were synthesized on the dextran. This result seems interesting, since dextran (150-kDa avg, Example 1) roughly four times larger than the dextran (40 kDa) used in this Example had about 4-5 poly alpha-1,3-glucan side chains synthesized thereupon (see Example 1). If 2-3 side chains could be synthesized on a 40 kDa dextran, it might have been expected that about 8-12 side chains (instead of 4-5) would have been synthesized on a 150-kDa dextran.

As shown in this Example, dextran of about 40 kDa could be used to prime poly alpha-1,3-glucan side chain synthesis. This result is noteworthy in view of Example 1, which shows that dextran of similar molecular weight did not prime such side chain synthesis when in the presence of larger dextran molecules. The partitioning effect observed in Example 1 (larger dextran preferentially used to prime synthesis of insoluble product, whereas smaller dextran remained in solution) is thus further intriguing, given the results of the present Example showing that smaller molecular weight dextran, when alone, can prime poly alpha-1,3-glucan side chain synthesis.

Example 5

Poly Alpha-1,3-Glucan Polymerization from Very High Molecular Weight Dextran Primer This Example describes synthesis of poly alpha-1,3-glucan with a glucosyltransferase enzyme using dextran with very high weight-average molecular weight (at least 50 million Daltons). Graft copolymers comprising a very large dextran backbone and poly alpha-1,3-glucan side chains were produced.

Dextran with a very high weight-average molecular weight was first prepared as described in Example 8 below, but with an enzymatic reaction comprising 300 g/L sucrose. The structure of this dextran comprises (i) about 87-93 wt % glucose linked at positions 1 and 6; (ii) about 0.1-1.2 wt % glucose linked at positions 1 and 3; (iii) about 0.1-0.7 wt % glucose linked at positions 1 and 4; (iv) about 7.7-8.6 wt % glucose linked at positions 1, 3 and 6; and (v) about 0.4-1.7 wt % glucose linked at: (a) positions 1, 2 and 6, or (b) positions 1, 4 and 6. This dextran was used in the following enzymatic reaction.

A 500-mL poly alpha-1,3-glucan synthesis reaction was run at 25° C. with stirring at 150 rpm using 100 g/L sucrose, 9.8 g/L dextran and 100 U/L of the glucosyltransferase used in the above Examples. To set up this reaction, dextran (4.9 g) was ground in a mortar and pestle and stirred at 50° C. with 470 g of tap water for 16 hr to give a hazy solution. Then sucrose (50 g, OmniPur Calbiochem 8550) and potassium monophosphate (0.68 g, Sigma P5379) were added and dissolved with stirring to give pH 5.75. The solution was stirred at 25° C. in a reactor, after which the glucosyltransferase enzyme (50 U) was added. In about half an hour, the reaction had become a suspension of firm, spongy particles of about 5 mm in size.

At 2 hr, a 50-mL sample was removed from the reaction (the polymer particles clogged the pipette, so not much insoluble product was obtained). This sample (a suspension) stood for a couple of hours before it was suction-filtered, washed and suctioned to a damp wet cake (1.3 g) and submitted for SEC analysis. The sample was not deactivated to kill enzyme activity, so additional poly alpha-1,3-glucan likely formed before it was suction-filtered. The filtrate was heated to deactivate the enzyme in it. The reaction was continued to 24 hr, after which the insoluble product slurry was suction-filtered; the filtrate (350 mL) was saved and analyzed by HPLC.

The initial filtrate was dialyzed by circulating across a Millipore PELLICON 2 PLCTK regenerated cellulose crossflow membrane (30-kDa cutoff; 0.1 $m^2$) at 100 mL/min and 10 psig. This dialysis served to remove monosaccharides and oligomers (via permeate), and leave unreacted, soluble dextran in the retentate. Deionized water was continuously added to the recirculating feed to replace water lost to permeate; ultimately, 3500 ml of water was used to wash out monosaccharides and oligomers. The retentate was then lyophilized to recover <0.1 g unreacted dextran. These results of only a small amount of soluble dextran in the enzyme reaction indicate that most of the dextran was used to prime poly alpha-1,3-glucan synthesis, thus drawing the dextran to the insoluble products of the reaction. That there was no apparent partitioning effect (unlike Example 1) was possibly related to the starting dextran being of relatively high homogeneity.

The insoluble product (dextran-poly alpha-1,3-glucan graft copolymer) of the glucosyltransferase reaction was washed three times with 500 mL of hot tap water; the product consisted of mostly 5-mm particles and a small amount of fines. The gross water was suction-removed and the damp particles were weighed (82.8 g; 24-hr sample); product samples were removed for SEC and percent solids determination. A wet cake sample (1.105 g) was oven-dried (60° C./2 days) for this purpose. The isolated dextran-poly alpha-1,3-glucan graft copolymer comprised about 25% dextran and 75% poly alpha-1,3-glucan.

Dextranase degradation analyses (performed as described in Example 1) indicated that the poly alpha-1,3-glucan side chains of the synthesized copolymer each had a DPw of roughly 1000. This side chain length molecular weight estimate is the same as that observed for side chains synthesized from lower molecular weight dextran (Example 1-2).

Thus, graft copolymers comprising (i) a very large, branched dextran backbone and (ii) poly alpha-1,3-glucan side chains were produced. Such copolymers had enhanced filterability and absorption profiles, as described in Examples 6-7 below.

Example 6

Filterability of Dextran-Poly Alpha-1,3-Glucan Graft Copolymer Comprising Very High Molecular Weight Dextran This Example describes the filterability of dextran-poly alpha-1,3-glucan graft copolymer product. In general, copolymer comprising an elevated content of very high molecular weight dextran was more easily filter-separated compared to copolymer with a lower content of such dextran.

Eight glucosyltransferase (100 U/L) reactions were set up and run generally as described in Example 5, but with the following modifications. The reactions were run at 25° C. in 1-L reactions stirred at 150 rpm using helical ribbon stirrers. Table 10 lists the amount of dextran and sucrose entered into each reaction. The pH of the reactions was 5.2-5.8 and left unadjusted. Insoluble product samples were taken at 24 hr after starting the reactions; these samples were worked up by filtering and washing. The resulting wet cakes were weighed and a sample thereof was dried to determine percent solids and yield. Insoluble product samples were analyzed by SEC and NMR. The results of each reaction are summarized in Table 10.

TABLE 10

Filterability Properties of Dextran-Poly Alpha-1,3-Glucan Graft Copolymers Produced in Glucosyltransferase Reactions

| 1-L Reaction | | | Copolymer Product Profile | | |
|---|---|---|---|---|---|
| Dextran (g) | Sucrose (g) | Sucrose Converted (%) | Copolymer Yield (g) | Dextran in Copolymer (wt %) | Copolymer Appearance |
| 5 | 100 | 100 | 40.0 | 10.6 | Stopped stirring; large particles (~5 mm balls), very coarse particulate, no fines, settled |
| 5 | 200 | 100 | 68.8 | 5.9 | Large particles (~4 mm) suspended in fine slurry; mostly granular |
| 2 | 100 | 100 | 38.4 | 4.5 | Stopped stirring; large particles remained suspended |
| 5 | 300 | 69 | 78.9 | 4.1 | Small particles suspended in fine slurry |
| 3 | 200 | 100 | 67.5 | 3.9 | Particles the size of sand grains suspended in fine slurry |
| 3 | 300 | 71 | 84.5 | 2.4 | Large particles (~4 mm) suspended in fine slurry |
| 1 | 200 | 99 | 75.8 | 1.4 | Fine particles; more difficult to filter than above products (rows 1-6) |
| 1 | 300 | 77 | 105.3 | 0.9 | Fine particles; more difficult to filter than above products (rows 1-6) |

Figure 4:
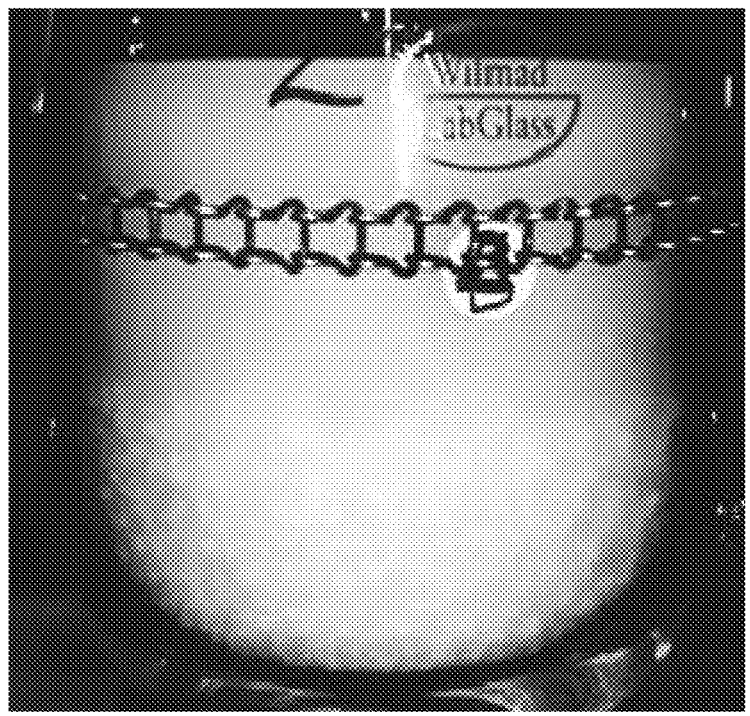
FIG. 4 shows a photograph of a dextran-poly alpha-1,3-glucan graft copolymer sample containing 10.6 wt % dextran. Refer to Example 6.
Figure 5:
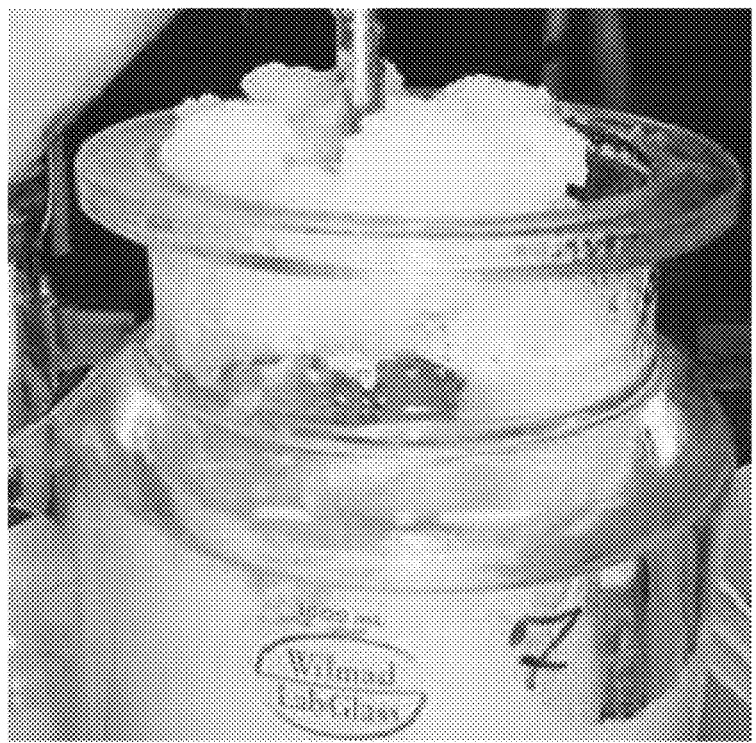
FIG. 5 shows a photograph of a dextran-poly alpha-1,3-glucan graft copolymer sample containing 0.9 wt % dextran. Refer to Example 6.

As shown in Table 10, the dextran-poly alpha-1,3-glucan graft copolymer products of the different reactions were characterized by their filterability. Overall, graft copolymers with a higher dextran content (e.g., 2.4-10.6 wt %) appeared as larger particles and were more easily filtered compared to their counterparts with lower dextran content (e.g., 0.9-1.4 wt %). FIGS. 4 and 5 show photographs of graft copolymer samples containing 10.6 wt % dextran (Table 10, row 1, more filterable) and 0.9 wt % dextran (Table 10, row 8, less filterable), respectively.

It is intriguing that the filterability of graft copolymer product depended, at least in part, on the content of dextran in the graft copolymer. This result is of some utility: it can now be seen that including a very high molecular weight dextran (>50 million Daltons) in a poly alpha-1,3-glucan synthesis reaction can lead to synthesis of a filterable product mostly comprised of poly alpha-1,3-glucan (note that the highest dextran content was 10.6 wt %, with other filterable products with an even lower dextran content). This is an enhancement over insoluble poly alpha-1,3-glucan homopolymer, which tends to exhibit poor filtration qualities. Thus, dextran-poly alpha-1,3-glucan graft copolymers with a dextran (very high molecular weight) content of at least about 2.4 wt % (and probably at least about 2.0 wt %), for example, may offer economic advantages over poly alpha-1,3-glucan homopolymer in terms of its synthesis and isolation. Furthermore, it can be seen from Table 10 that only a small amount of very high molecular weight dextran in the glucosyltransferase reaction was needed to induce this effect. Based on Table 10, it appears that using as little as 2 g/L, for example, of very high molecular weight dextran in a glucosyltransferase reaction can yield more filterable graft copolymer product. Finally, this effect on filterability was not readily observed with dextran-poly alpha-1,3-glucan graft copolymers produced in a glucosyltransferase reaction in which a lower molecular weight dextran (150-kDa [avg], Sigma D4876) was used as primer (data not shown).

Thus, dextran-poly alpha-1,3-glucan graft copolymer comprising at least about 2 wt %, for example, of very high molecular weight dextran is more filterable compared to graft copolymer with a lower dextran content.

Example 7

Absorption of Aqueous Liquid by Dextran-Poly Alpha-1,3-Glucan Graft Copolymers Comprising Very High Molecular Weight Dextran This Example describes the water retention values (WRVs) of various dextran-poly alpha-1,3-glucan graft copolymers. The WRVs measured with these copolymers are greater than the WRV measured with poly alpha-1,3-glucan homopolymer.

Three glucosyltransferase (100 U/L) reactions were set up and run generally as described in Example 6, using 100 g/L sucrose and dextran at 2, 5, or 10 g/L. These reactions (24 hr) produced dextran-poly alpha-1,3-glucan graft copolymers comprising, respectively, 95%, 87.5%, or 75% alpha-1,3 glucosidic linkages. This product linkage profile is consistent with the products listed in rows 1 and 3 of Table 10, which were made under similar reaction conditions (initial sucrose and dextran levels) (note that the dextran component in each product large represents alpha-1,6-glucosidic linkages).

The WRV of each of these graft copolymer products was measured, and compared to the WRV of poly alpha-1,3-glucan homopolymer (DPw 800) (Table 11). The WRV of each polymer was measured as follows. Dried polymer powder (1 g) was immersed in 20 mL of DI water and left to equilibrate for 2 hours (note that polymer drying did not involve any freeze-drying step). The solid material (appeared as a slurry) was then transferred into a 50-mL FALCON tube containing a 0.45-micron PVDF filter insert on the top half of the tube. The FALCON tube was then centrifuged at 4500 rpm for 20 minutes in an EPPENDORF 5804 centrifuge with fixed rotor. The filter insert allowed removal/separation of bulk excess liquid from the wet material during centrifugation. The mass of the wet material was then measured on a balance, after which it was dried overnight in an oven at 60° C. The dry mass was then measured. WRV for each polymer was calculated using the following formula: ((mass of wet polymer−mass of dry polymer)/mass of dry polymer)*100.

TABLE 11

Water Retention Values (WRVs) of Poly Alpha-1,3-Glucan Homopolymer
and Dextran-Poly Alpha-1,3-Glucan Graft Copolymers

|  | Poly Alpha-1,3-Glucan Homopolymer (DPw 800) | Dextran-Poly Alpha-1,3-Glucan Graft Copolymer | | |
|---|---|---|---|---|
| Dextran conc. in reaction | na | 2 g/L | 5 g/L | 10 g/L |
| % alpha-1,3 linkage | 100% | 95% | 87.5% | 75% |
| WRV | 80 | 132 | 129 | 172 |

The results in Table 11 indicate that dextran-poly alpha-1,3-glucan graft copolymers, even when containing a small amount of alpha-1,6 glucosidic linkages (<5%), have significantly higher WRVs compared to the WRV of poly alpha-1,3-glucan homopolymer.

Additional glucosyltransferase (100 U/L) reactions (24 hr) were run as described above, but in which 50 g/L of very high molecular weight dextran and various amounts of sucrose (20-200 g/L) were used. The WRV of each synthesized dextran-poly alpha-1,3-glucan graft copolymer produced in these reactions was measured as described above, but with the following modifications since the products became gel-like upon water addition (typically occurred when measured WRV exceeded ~1000). This protocol modification was made to avoid filter clogging during centrifugation. Specifically, after adding water, the swollen material was added to a 50-mL FALCON tube without a PVDF filter insert, and centrifuged at 4500 rpm for 20 minutes in an EPPENDORF 5804. The swollen gel phase settles at the bottom of the tube during this centrifugation, and the excess water can easily be decanted. The mass of the wet material was then measured on a balance, after which it was dried overnight in an oven at 60° C., and the dry material was weighed. WRV's were then determined following the above formula and are provided in Table 12.

TABLE 12

Water Retention Values (WRVs) of Dextran-Poly Alpha-1,3-Glucan
Graft Copolymers Produced in Reactions Comprising a High Amount
of Dextran

| | Sucrose Concentration in Reaction | | | | |
|---|---|---|---|---|---|
| | 200 g/L | 150 g/L | 100 g/L | 50 g/L | 20 g/L |
| WRV | 2811 | 3562 | 1988 | 2685 | 3186 |

The results in Table 12 indicate that dextran-poly alpha-1,3-glucan graft copolymers produced in glucosyltransferase reactions comprising high amounts of very high molecular weight dextran (50 g/L) have enhanced WRVs.

Thus, compositions comprising dextran-poly alpha-1,3-glucan graft copolymers are able to absorb aqueous liquid. Such absorbency indicates that these compositions are likely suitable for use in various personal care items whose performance is based, in part, on aqueous liquid absorption (e.g., diapers, certain feminine hygiene products). In addition, it is notable that the enhanced WRV of these materials was achieved without the need of chemical modifications (e.g., cross-linking), which could otherwise render material less suitable for certain personal care applications (e.g., chemical processing can leave impurities that have been linked to skin inflammation).

Example 8

Synthesis and Analysis of Dextran with Very High Molecular Weight

This Example describes production of dextran with very high molecular weight (greater than 50 million Daltons). Such dextran was used in Examples 5-7 (above) to produce dextran-poly alpha-1,3-glucan graft copolymers with enhanced features.

Gtf 0768 Production

A putative YG repeat-containing hydrolase (categorized in GENBANK under GI number 339480768, but now having GI number 497964659) with 1484 amino acids was identified from *Leuconostoc pseudomesenteroides* strain KCTC3652 by whole genome shotgun sequencing. This putative glucosyltransferase (designated herein as gtf 0768) belongs to the GH70 family of glycosyl hydrolases containing a glucan-binding domain. The N-terminal 37 amino acid segment of gtf 0768 was deduced as the signal peptide of the enzyme by the SIGNALP 4.0 program (Petersen et al., Nature Methods 8:785-786). The mature form of gtf 0768 is represented by SEQ ID NO:6.

To construct a plasmid for bacterial expression of gtf 0768, a DNA sequence encoding a mature form of the gtf without the signal peptide was synthesized by GenScript USA Inc. (Piscataway, NJ). The synthesized sequence was subcloned into the NheI and HindIII sites of the pET23D+ vector (NOVAGEN®; Merck KGaA, Darmstadt, Germany). The 0768 gtf (SEQ ID NO:7) encoded by this construct included a start methionine and 3 additional amino acids (Ala-Ser-Ala) at the N-terminus, and 6 histidine residues at the C-terminus, compared to the wild type mature (predicted) form of gtf 0768 (SEQ ID NO:6) (i.e., SEQ ID NO:6 is comprised in SEQ ID NO:7). The plasmid construct was sequence-confirmed and transformed into *E. coli* BL21 DE3 host cells with ampicillin selection, resulting in expression strain EC0052.

Cells of EC0052 and a control strain containing only empty pET23D+ vector were grown in LB medium with 100 µg/mL ampicillin to $OD_{600}$ ~0.5, and then induced with 1 mM IPTG at 37° C. for 3 hours or alternatively induced at 23° C. overnight. Following this induction period, cells were collected by centrifugation at 4000×g for 10 min and resuspended in PBS buffer pH 6.8. The cells were then lysed by passing through a French Press at 14,000 psi (~96.53 MPa) twice, after which cell debris was pelleted by centrifugation at 15,000×g for 20 min. The supernatants of each crude cell lysate were aliquoted and frozen at −80° C.

The activity of crude cell lysate from EC0052 cells was checked by reaction with sucrose. A control reaction was set up similarly using cell lysate prepared from cells containing the empty vector. Each sucrose reaction was set up using 10% (v/v) of cell lysate with 100 g/L sucrose, 10 mM sodium citrate pH 5, and 1 mM $CaCl_2$). After incubation of the reactions at 37° C. for a few hours, a gel-like product, believed to be a dextran, was formed in the tube in which EC0052 cell lysate had been added. No gel-like product was formed in the control reaction. HPLC analysis confirmed that sucrose was consumed in the reaction containing EC0052 cell lysate, and not in the control reaction. This result suggested that the EC0052 crude cell lysate expressed active gtf 0768 enzyme, and that this gtf produced a dextran product having high viscosity.

Synthesis and Analysis of Very High Molecular Weight Dextran

Reactions comprising water, sucrose and gtf 0768 were set up, and analyses were performed to determine the structural features of the dextran product.

Reagents for preparing gtf reaction:
Sucrose (Sigma Prod. No. S-9378).
Sodium phosphate buffer stock (1 M, pH 6.5, Teknova Cat No: S0276).
Gtf 0768 enzyme (comprising SEQ ID NO:6) solution (cell lysate as prepared above).

Gtf reaction conditions:

A 50-mL reaction was prepared containing 20 mM sodium phosphate buffer (buffer was diluted 50-fold with ddH2O from 1 M stock, pH 6.5), 100 g/L sucrose, and 0.1 mL of gtf 0768 enzyme (comprising SEQ ID NO:6) solution. The reaction was shaken at 100 rpm in an incubator shaker (Innova, Model 4000) at 26° C. for 43 hours; the reaction became viscous after about 24 hours. Other reactions (24 hours) containing 200, 300 or 800 g/L sucrose were also performed (data not shown).

The gtf enzyme was deactivated by heating the reaction at 80° C. for 10 minutes. The deactivated viscous reaction was then mixed with 75 mL of 100% methanol to precipitate the viscous product. A white precipitate was formed. After carefully decanting the supernatant, the white precipitate was washed twice with 75 mL of 100% methanol. The solid product was dried at 45° C. under vacuum in an oven for 48 hours.

Samples (1 mL) of the reaction were taken at 0, 0.5, 1, 2, and 24 hours, respectively. The gtf enzyme was deactivated in each sample by heating at 80° C. for 10 minutes. Each sample was then diluted 10-fold with sterile water. 500 μL of diluted sample was transferred into a centrifuge tube filter (SPIN-X, 0.45-μm Nylon, 2.0 mL Polypropylene Tube, Costar #8170) and centrifuged at 12,000 rpm in a table centrifuge for 60 minutes, after which 200 μL of flow-through was used for HPLC analysis to measure sucrose consumption during the reaction. The following HPLC conditions were applied for analyzing each sample: column (AMINEX HPX-87C carbohydrate column, 300×7.8 mm, Bio-Rad, No. 125-0095), eluent (water), flow rate (0.6 mL/min), temperature (85° C.), refractive index detector. HPLC analysis of the samples indicated substantial sucrose consumption during the 0768 gtf reaction.

HPLC was also used to analyze other products of the reaction. Polymer yield was back-calculated by subtracting the amount of all other saccharides left in the reaction from the amount of the starting sucrose. The back-calculated number was consistent with the viscous product dry weight analysis. Sucrose, leucrose, glucose and fructose were quantified by HPLC with an HPX-87C column (HPLC conditions as described above). DP2-7 oligosaccharides were quantified by HPLC with the following conditions: column (AMINEX HPX-42A carbohydrate column, 300×7.8 mm, Bio-Rad, No. 125-0097), eluent (water), flow rate (0.6 mL/min), temperature (85° C.), refractive index detector. These HPLC analyses indicated that the glucosyl-containing saccharide products of the 0768 gtf reaction consisted of 92.3% polymer product, 1.3% glucose, 5.0% leucrose, and 1.4% DP2-7 oligosaccharides.

A sample of dry dextran powder product (~0.2 g) of the above reaction was used for molecular weight analysis. Molecular weight was determined by a flow injection chromatographic method using an Alliance™ 2695 separation module from Waters Corporation (Milford, MA) coupled with three online detectors: a differential refractometer 2414 from Waters, a Heleos™-2 18-angle multiangle light scattering (MALS) photometer with quasielastic light scattering (QELS) detector from Wyatt Technologies (Santa Barbara, CA), and a ViscoStar™ differential capillary viscometer from Wyatt. The dry dextran powder was dissolved at 0.5 mg/ml in aqueous Tris (Tris[hydroxymethyl]aminomethane) buffer (0.075 M) containing 200 ppm $NaN_3$. The dissolution of dextran was achieved by shaking overnight at 50° C. Two AQUAGEL-OH GUARD columns from Agilent Technologies (Santa Clara, CA) were used to separate the dextran polymer peak from the injection peak. The mobile base for this procedure was the same as the dextran solvent, the flow rate was 0.2 mL/min, the injection volume was 0.1 mL, and the column temperature was 30° C. Empower™ version 3 software from Waters was used for data acquisition, and Astra™ version 6 software from Wyatt was used for multidetector data reduction. It was determined from this work that the dextran polymer product had a weight-average molecular weight (Mw) of $1.022$ $(+/-0.025) \times 10^8$ g/mol (i.e., roughly 100 million Daltons) (from MALS analysis), a z-average radius of gyration of 243.33 (+/−0.42) nm (from MALS analysis), and a z-average hydrodynamic radius of 215 nm (from QELS analysis). It was also determined from QELS analysis that the dextran has a standard deviation of particle size distribution (PSD) of about 0.259, indicating that the dextran likely is polydisperse in terms of hydrodynamic size.

For glycosidic linkage analysis purposes, a 50-mL gtf reaction was prepared as described above in this Example (100 g/L sucrose), except that the reaction time was 24 hours (reaction had become viscous). The gtf enzyme was deactivated by heating the reaction at 80° C. for 10 minutes. The deactivated viscous reaction was then placed into a regenerated cellulose sturdy dialysis tubing with a molecular weight cut-off (MWCO) of 12-14 kDa (Spectra/Por® 4 Dialysis Tubing, Part No. 132706, Spectrum Laboratories, Inc.) and dialyzed against 4 L of filter water at room temperature over one week. Water was exchanged every day during this dialysis. The dialyzed viscous reaction was then precipitated and dried as described above in this Example. About 0.2 g of dry powder was submitted for GC/MS linkage analysis.

Linkage analysis was performed according to methods described by Pettolino et al. (*Nature Protocols* 7:1590-1607), which is incorporated herein by reference. Briefly, a dry dextran sample was dissolved in dimethyl sulfoxide (DMSO) or 5% lithium chloride in DMSO, then all free hydroxyl groups were methylated by sequential addition of a sodium hydroxide/DMSO slurry followed by iodomethane. The methylated polymer was then extracted into methylene chloride and hydrolyzed to monomeric units using aqueous trifluoroacetic acid (TFA) at 120° C. The TFA was then evaporated from the sample and reductive ring opening was done using sodium borodeuteride, which also labeled the reducing end with a deuterium atom. The hydroxyl groups created by hydrolyzing the glycosidic linkages were then acetylated by treating with acetyl chloride and TFA at a temperature of 50° ° C. Finally, the derivatizing reagents were evaporated and the resulting methylated/acetylated monomers were reconstituted in acetonitrile and analyzed by gas chromatography with mass spectrometry (GC/MS) using a biscyanopropyl cyanopropylphenyl polysiloxane column. The relative positioning of the methyl and acetyl functionalities, along with the deuterium label, yielded species that have distinctive retention time indices and mass spectra that can be compared to published databases. In this way, the derivatives of the monomeric units indicated how each monomer was originally linked in the dextran polymer and whether the monomer was a branch point. The results of analyzing these samples (dextran initially dissolved in DMSO or DMSO/5% LiCl) are provided in Table 13.

TABLE 13

Linkage Profile of Gtf 0768 Dextran Product

| Sample | Wt %/Mol % of Glucose Monomers in Dextran | | | | |
|---|---|---|---|---|---|
| | 3-glc [a] | 6-glc [b] | 4-glc [c] | 3,6-glc [d] | 2,6- + 4,6-glc [e] |
| DMSO | 0.4 | 90.2 | 0.4 | 8.3 | 0.7 |
| DMSO/5% LiCl | 0.9 | 89.3 | 0.4 | 8.0 | 1.4 |

[a] Glucose monomer linked at carbon positions 1 and 3.
[b] Glucose monomer linked at carbon positions 1 and 6.
[c] Glucose monomer linked at carbon positions 1 and 4.
[d] Glucose monomer linked at carbon positions 1, 3 and 6.
[e] Glucose monomer linked at carbon positions 1, 2 and 6, or 1, 4 and 6.

In general, the results in Table 13 indicate that the dextran product analyzed above comprises:

(i) about 87-93 wt % glucose linked only at positions 1 and 6;
(ii) about 0.1-1.2 wt % glucose linked only at positions 1 and 3;
(iii) about 0.1-0.7 wt % glucose linked only at positions 1 and 4;
(iv) about 7.7-8.6 wt % glucose linked only at positions 1, 3 and 6; and
(v) about 0.4-1.7 wt % glucose linked only at (a) positions 1, 2 and 6, or (b) positions 1, 4 and 6.

Based on this information and some other studies (data not shown), it is contemplated that this product is a branched structure in which there are long chains (containing mostly or all alpha-1,6-linkages) of about 20 DP in length (average) that iteratively branch from each other (e.g., a long chain can be a branch from another long chain, which in turn can itself be a branch from another long chain, and so on). The branched structure also appears to comprise short branches from the long chains; these short chains are believed to be 1-3 DP in length and mostly comprise alpha-1,3 and -1,4 linkages, for example. Branch points in the dextran, whether from a long chain branching from another long chain, or a short chain branching from a long chain, appear to comprise alpha-1,3, -1,4, or -1,2 linkages off of a glucose involved in alpha-1,6 linkage. Roughly 25% of all the branch points of the dextran branched into a long chain.

Thus, a very high molecular weight dextran was produced having unique structural characteristics. This dextran was used in Examples 5-7 (above) to produce dextran-poly alpha-1,3-glucan graft copolymers with enhanced features.

SEQUENCE LISTING

<160> NUMBER OF SEQ ID NOS: 7

<210> SEQ ID NO 1
<211> LENGTH: 1341
<212> TYPE: PRT
<213> ORGANISM: Streptococcus salivarius

<400> SEQUENCE: 1

Met Ile Asp Gly Lys Tyr Tyr Val Asn Glu Asp Gly Ser His Lys
1               5                   10                  15

Glu Asn Phe Ala Ile Thr Val Asn Gly Gln Leu Leu Tyr Phe Gly Lys
            20                  25                  30

Asp Gly Ala Leu Thr Ser Ser Ser Thr Tyr Ser Phe Thr Pro Gly Thr
        35                  40                  45

Thr Asn Ile Val Asp Gly Phe Ser Ile Asn Asn Arg Ala Tyr Asp Ser
    50                  55                  60

Ser Glu Ala Ser Phe Glu Leu Ile Asp Gly Tyr Leu Thr Ala Asp Ser
65                  70                  75                  80

Trp Tyr Arg Pro Ala Ser Ile Ile Lys Asp Gly Val Thr Trp Gln Ala
                85                  90                  95

Ser Thr Ala Glu Asp Phe Arg Pro Leu Leu Met Ala Trp Trp Pro Asn
            100                 105                 110

Val Asp Thr Gln Val Asn Tyr Leu Asn Tyr Met Ser Lys Val Phe Asn
        115                 120                 125

Leu Asp Ala Lys Tyr Ser Ser Thr Asp Lys Gln Glu Thr Leu Lys Val
    130                 135                 140

Ala Ala Lys Asp Ile Gln Ile Lys Ile Glu Gln Lys Ile Gln Ala Glu
145                 150                 155                 160

Lys Ser Thr Gln Trp Leu Arg Glu Thr Ile Ser Ala Phe Val Lys Thr
                165                 170                 175

Gln Pro Gln Trp Asn Lys Glu Thr Glu Asn Tyr Ser Lys Gly Gly Gly
            180                 185                 190

-continued

Glu Asp His Leu Gln Gly Gly Ala Leu Leu Tyr Val Asn Asp Ser Arg
            195                 200                 205

Thr Pro Trp Ala Asn Ser Asp Tyr Arg Arg Leu Asn Arg Thr Ala Thr
210                 215                 220

Asn Gln Thr Gly Thr Ile Asp Lys Ser Ile Leu Asp Glu Gln Ser Asp
225                 230                 235                 240

Pro Asn His Met Gly Gly Phe Asp Phe Leu Leu Ala Asn Asp Val Asp
                245                 250                 255

Leu Ser Asn Pro Val Val Gln Ala Glu Gln Leu Asn Gln Ile His Tyr
            260                 265                 270

Leu Met Asn Trp Gly Ser Ile Val Met Gly Asp Lys Asp Ala Asn Phe
        275                 280                 285

Asp Gly Ile Arg Val Asp Ala Val Asp Asn Val Asp Ala Asp Met Leu
    290                 295                 300

Gln Leu Tyr Thr Asn Tyr Phe Arg Glu Tyr Tyr Gly Val Asn Lys Ser
305                 310                 315                 320

Glu Ala Asn Ala Leu Ala His Ile Ser Val Leu Glu Ala Trp Ser Leu
                325                 330                 335

Asn Asp Asn His Tyr Asn Asp Lys Thr Asp Gly Ala Ala Leu Ala Met
            340                 345                 350

Glu Asn Lys Gln Arg Leu Ala Leu Leu Phe Ser Leu Ala Lys Pro Ile
        355                 360                 365

Lys Glu Arg Thr Pro Ala Val Ser Pro Leu Tyr Asn Asn Thr Phe Asn
    370                 375                 380

Thr Thr Gln Arg Asp Glu Lys Thr Asp Trp Ile Asn Lys Asp Gly Ser
385                 390                 395                 400

Lys Ala Tyr Asn Glu Asp Gly Thr Val Lys Gln Ser Thr Ile Gly Lys
                405                 410                 415

Tyr Asn Glu Lys Tyr Gly Asp Ala Ser Gly Asn Tyr Val Phe Ile Arg
            420                 425                 430

Ala His Asp Asn Asn Val Gln Asp Ile Ile Ala Glu Ile Ile Lys Lys
        435                 440                 445

Glu Ile Asn Pro Lys Ser Asp Gly Phe Thr Ile Thr Asp Ala Glu Met
450                 455                 460

Lys Gln Ala Phe Glu Ile Tyr Asn Lys Asp Met Leu Ser Ser Asp Lys
465                 470                 475                 480

Lys Tyr Thr Leu Asn Asn Ile Pro Ala Ala Tyr Ala Val Met Leu Gln
                485                 490                 495

Asn Met Glu Thr Ile Thr Arg Val Tyr Tyr Gly Asp Leu Tyr Thr Asp
            500                 505                 510

Asp Gly His Tyr Met Glu Thr Lys Ser Pro Tyr Tyr Asp Thr Ile Val
        515                 520                 525

Asn Leu Met Lys Ser Arg Ile Lys Tyr Val Ser Gly Gly Gln Ala Gln
    530                 535                 540

Arg Ser Tyr Trp Leu Pro Thr Asp Gly Lys Met Asp Asn Ser Asp Val
545                 550                 555                 560

Glu Leu Tyr Arg Thr Asn Glu Val Tyr Thr Ser Val Arg Tyr Gly Lys
                565                 570                 575

Asp Ile Met Thr Ala Asn Asp Thr Glu Gly Ser Lys Tyr Ser Arg Thr
            580                 585                 590

Ser Gly Gln Val Thr Leu Val Ala Asn Asn Pro Lys Leu Asn Leu Asp
        595                 600                 605

Gln Ser Ala Lys Leu Asn Val Glu Met Gly Lys Ile His Ala Asn Gln

```
                610             615             620
Lys Tyr Arg Ala Leu Ile Val Gly Thr Ala Asp Gly Ile Lys Asn Phe
625             630             635             640

Thr Ser Asp Ala Asp Ala Ile Ala Ala Gly Tyr Val Lys Glu Thr Asp
                645             650             655

Ser Asn Gly Val Leu Thr Phe Gly Ala Asn Asp Ile Lys Gly Tyr Glu
                660             665             670

Thr Phe Asp Met Ser Gly Phe Val Ala Val Trp Val Pro Val Gly Ala
                675             680             685

Ser Asp Asn Gln Asp Ile Arg Val Ala Pro Ser Thr Glu Ala Lys Lys
690             695             700

Glu Gly Glu Leu Thr Leu Lys Ala Thr Glu Ala Tyr Asp Ser Gln Leu
705             710             715             720

Ile Tyr Glu Gly Phe Ser Asn Phe Gln Thr Ile Pro Asp Gly Ser Asp
                725             730             735

Pro Ser Val Tyr Thr Asn Arg Lys Ile Ala Glu Asn Val Asp Leu Phe
                740             745             750

Lys Ser Trp Gly Val Thr Ser Phe Glu Met Ala Pro Gln Phe Val Ser
                755             760             765

Ala Asp Asp Gly Thr Phe Leu Asp Ser Val Ile Gln Asn Gly Tyr Ala
770             775             780

Phe Ala Asp Arg Tyr Asp Leu Ala Met Ser Lys Asn Asn Lys Tyr Gly
785             790             795             800

Ser Lys Glu Asp Leu Arg Asp Ala Leu Lys Ala Leu His Lys Ala Gly
                805             810             815

Ile Gln Ala Ile Ala Asp Trp Val Pro Asp Gln Ile Tyr Gln Leu Pro
                820             825             830

Gly Lys Glu Val Val Thr Ala Thr Arg Thr Asp Gly Ala Gly Arg Lys
                835             840             845

Ile Ala Asp Ala Ile Ile Asp His Ser Leu Tyr Val Ala Asn Ser Lys
850             855             860

Ser Ser Gly Lys Asp Tyr Gln Ala Lys Tyr Gly Gly Glu Phe Leu Ala
865             870             875             880

Glu Leu Lys Ala Lys Tyr Pro Glu Met Phe Lys Val Asn Met Ile Ser
                885             890             895

Thr Gly Lys Pro Ile Asp Asp Ser Val Lys Leu Lys Gln Trp Lys Ala
                900             905             910

Glu Tyr Phe Asn Gly Thr Asn Val Leu Glu Arg Gly Val Gly Tyr Val
                915             920             925

Leu Ser Asp Glu Ala Thr Gly Lys Tyr Phe Thr Val Thr Lys Glu Gly
930             935             940

Asn Phe Ile Pro Leu Gln Leu Thr Gly Lys Glu Lys Val Ile Thr Gly
945             950             955             960

Phe Ser Ser Asp Gly Lys Gly Ile Thr Tyr Phe Gly Thr Ser Gly Thr
                965             970             975

Gln Ala Lys Ser Ala Phe Val Thr Phe Asn Gly Asn Thr Tyr Tyr Phe
                980             985             990

Asp Ala Arg Gly His Met Val Thr  Asn Ser Glu Tyr Ser  Pro Asn Gly
                995             1000            1005

Lys Asp  Val Tyr Arg Phe Leu  Pro Asn Gly Ile Met  Leu Ser Asn
    1010            1015             1020

Ala Phe  Tyr Ile Asp Ala Asn  Gly Asn Thr Tyr Leu  Tyr Asn Ser
    1025            1030             1035
```

Lys Gly Gln Met Tyr Lys Gly Gly Tyr Thr Lys Phe Asp Val Ser
     1040              1045                1050

Glu Thr Asp Lys Asp Gly Lys Glu Ser Lys Val Val Lys Phe Arg
     1055              1060                1065

Tyr Phe Thr Asn Glu Gly Val Met Ala Lys Gly Val Thr Val Ile
     1070              1075                1080

Asp Gly Phe Thr Gln Tyr Phe Gly Glu Asp Gly Phe Gln Ala Lys
     1085              1090                1095

Asp Lys Leu Val Thr Phe Lys Gly Lys Thr Tyr Tyr Phe Asp Ala
     1100              1105                1110

His Thr Gly Asn Gly Ile Lys Asp Thr Trp Arg Asn Ile Asn Gly
     1115              1120                1125

Lys Trp Tyr Tyr Phe Asp Ala Asn Gly Val Ala Ala Thr Gly Ala
     1130              1135                1140

Gln Val Ile Asn Gly Gln Lys Leu Tyr Phe Asn Glu Asp Gly Ser
     1145              1150                1155

Gln Val Lys Gly Gly Val Val Lys Asn Ala Asp Gly Thr Tyr Ser
     1160              1165                1170

Lys Tyr Lys Glu Gly Phe Gly Glu Leu Val Thr Asn Glu Phe Phe
     1175              1180                1185

Thr Thr Asp Gly Asn Val Trp Tyr Tyr Ala Gly Ala Asn Gly Lys
     1190              1195                1200

Thr Val Thr Gly Ala Gln Val Ile Asn Gly Gln His Leu Tyr Phe
     1205              1210                1215

Asn Ala Asp Gly Ser Gln Val Lys Gly Gly Val Val Lys Asn Ala
     1220              1225                1230

Asp Gly Thr Tyr Ser Lys Tyr Asn Ala Ser Thr Gly Glu Arg Leu
     1235              1240                1245

Thr Asn Glu Phe Phe Thr Thr Gly Asp Asn Asn Trp Tyr Tyr Ile
     1250              1255                1260

Gly Ala Asn Gly Lys Ser Val Thr Gly Glu Val Lys Ile Gly Asp
     1265              1270                1275

Asp Thr Tyr Phe Phe Ala Lys Asp Gly Lys Gln Val Lys Gly Gln
     1280              1285                1290

Thr Val Ser Ala Gly Asn Gly Arg Ile Ser Tyr Tyr Tyr Gly Asp
     1295              1300                1305

Ser Gly Lys Arg Ala Val Ser Thr Trp Ile Glu Ile Gln Pro Gly
     1310              1315                1320

Val Tyr Val Tyr Phe Asp Lys Asn Gly Leu Ala Tyr Pro Pro Arg
     1325              1330                1335

Val Leu Asn
     1340

<210> SEQ ID NO 2
<211> LENGTH: 1341
<212> TYPE: PRT
<213> ORGANISM: Streptococcus salivarius K12

<400> SEQUENCE: 2

Met Thr Asp Gly Lys Tyr Tyr Val Asn Glu Asp Gly Ser His Lys
1               5                   10                  15

Glu Asn Phe Ala Ile Thr Val Asn Gly Gln Leu Leu Tyr Phe Gly Lys
            20                  25                  30

Asp Gly Ala Leu Thr Ser Ser Ser Thr His Ser Phe Thr Pro Gly Thr

```
            35                  40                  45
Thr Asn Ile Val Asp Gly Phe Ser Ile Asn Asn Arg Ala Tyr Asp Ser
 50                  55                  60

Ser Glu Ala Ser Phe Glu Leu Ile Asn Gly Tyr Leu Thr Ala Asp Ser
 65                  70                  75                  80

Trp Tyr Arg Pro Val Ser Ile Ile Lys Asp Gly Val Thr Trp Gln Ala
                     85                  90                  95

Ser Thr Ala Glu Asp Phe Arg Pro Leu Leu Met Ala Trp Trp Pro Asn
                100                 105                 110

Val Asp Thr Gln Val Asn Tyr Leu Asn Tyr Met Ser Lys Val Phe Asn
                115                 120                 125

Leu Glu Ala Lys Tyr Thr Ser Thr Asp Lys Gln Ala Asp Leu Asn Arg
    130                 135                 140

Ala Ala Lys Asp Ile Gln Val Lys Ile Glu Gln Lys Ile Gln Ala Glu
145                 150                 155                 160

Lys Ser Thr Gln Trp Leu Arg Glu Thr Ile Ser Ala Phe Val Lys Thr
                165                 170                 175

Gln Pro Gln Trp Asn Lys Glu Thr Glu Asn Tyr Ser Lys Gly Gly Gly
                180                 185                 190

Glu Asp His Leu Gln Gly Gly Ala Leu Leu Tyr Val Asn Asp Ser Arg
    195                 200                 205

Thr Pro Trp Ala Asn Ser Asn Tyr Arg Leu Leu Asn Arg Thr Ala Thr
    210                 215                 220

Asn Gln Thr Gly Thr Ile Asn Lys Ser Val Leu Asp Glu Gln Ser Asp
225                 230                 235                 240

Pro Asn His Met Gly Gly Phe Asp Phe Leu Leu Ala Asn Asp Val Asp
                245                 250                 255

Leu Ser Asn Pro Val Val Gln Ala Glu Gln Leu Asn Gln Ile His Tyr
                260                 265                 270

Leu Met Asn Trp Gly Ser Ile Val Met Gly Asp Lys Asp Ala Asn Phe
    275                 280                 285

Asp Gly Ile Arg Val Asp Ala Val Asp Asn Val Asn Ala Asp Met Leu
    290                 295                 300

Gln Leu Tyr Thr Asn Tyr Phe Arg Glu Tyr Tyr Gly Val Asn Lys Ser
305                 310                 315                 320

Glu Ala Gln Ala Leu Ala His Ile Ser Val Leu Glu Ala Trp Ser Leu
                325                 330                 335

Asn Asp Asn His Tyr Asn Asp Lys Thr Asp Gly Ala Ala Leu Ala Met
                340                 345                 350

Glu Asn Lys Gln Arg Leu Ala Leu Leu Phe Ser Leu Ala Lys Pro Ile
    355                 360                 365

Lys Asp Arg Thr Pro Ala Val Ser Pro Leu Tyr Asn Asn Thr Phe Asn
    370                 375                 380

Thr Thr Gln Arg Asp Phe Lys Thr Asp Trp Ile Asn Lys Asp Gly Ser
385                 390                 395                 400

Thr Ala Tyr Asn Glu Asp Gly Thr Ala Lys Gln Ser Thr Ile Gly Lys
                405                 410                 415

Tyr Asn Glu Lys Tyr Gly Asp Ala Ser Gly Asn Tyr Val Phe Ile Arg
                420                 425                 430

Ala His Asp Asn Asn Val Gln Asp Ile Ile Ala Glu Ile Ile Lys Lys
    435                 440                 445

Glu Ile Asn Lys Lys Ser Asp Gly Phe Thr Ile Ser Asp Ser Glu Met
450                 455                 460
```

```
Lys Gln Ala Phe Glu Ile Tyr Asn Lys Asp Met Leu Ser Ser Asn Lys
465                 470                 475                 480

Lys Tyr Thr Leu Asn Asn Ile Pro Ala Ala Tyr Ala Val Met Leu Gln
                485                 490                 495

Asn Met Glu Thr Ile Thr Arg Val Tyr Tyr Gly Asp Leu Tyr Thr Asp
            500                 505                 510

Asp Gly His Tyr Met Glu Thr Lys Ser Pro Tyr His Asp Thr Ile Val
        515                 520                 525

Asn Leu Met Lys Asn Arg Ile Lys Tyr Val Ser Gly Gly Gln Ala Gln
    530                 535                 540

Arg Ser Tyr Trp Leu Pro Thr Asp Gly Lys Met Asp Asn Ser Asp Val
545                 550                 555                 560

Glu Leu Tyr Arg Thr Ser Glu Val Tyr Thr Ser Val Arg Tyr Gly Lys
                565                 570                 575

Asp Ile Met Thr Ala Asp Asp Thr Glu Gly Ser Lys Tyr Ser Arg Thr
            580                 585                 590

Ser Gly Gln Val Thr Leu Val Val Asn Asn Pro Lys Leu Thr Leu His
        595                 600                 605

Glu Ser Ala Lys Leu Asn Val Glu Met Gly Lys Ile His Ala Asn Gln
    610                 615                 620

Lys Tyr Arg Ala Leu Ile Val Gly Thr Ala Asp Gly Ile Lys Asn Phe
625                 630                 635                 640

Thr Ser Asp Ala Glu Ala Ile Ala Ala Gly Tyr Val Lys Glu Thr Asp
                645                 650                 655

Ser Asn Gly Val Leu Thr Phe Gly Ala Asn Asp Ile Lys Gly Tyr Glu
            660                 665                 670

Thr Phe Asp Met Ser Gly Phe Val Ala Val Trp Val Pro Val Gly Ala
        675                 680                 685

Ser Asp Asp Gln Asp Ile Arg Val Ala Pro Ser Thr Glu Ala Lys Lys
    690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp
                725                 730                 735

Pro Ser Val Tyr Thr Asn Arg Lys Ile Ala Glu Asn Val Asp Leu Phe
            740                 745                 750

Lys Ser Trp Gly Val Thr Ser Phe Glu Met Ala Pro Gln Phe Val Ser
        755                 760                 765

Ala Asp Asp Gly Thr Phe Leu Asp Ser Val Ile Gln Asn Gly Tyr Ala
    770                 775                 780

Phe Ala Asp Arg Tyr Asp Leu Ala Met Ser Lys Asn Asn Lys Tyr Gly
785                 790                 795                 800

Ser Lys Glu Asp Leu Arg Asp Ala Leu Lys Ala Leu His Lys Ala Gly
                805                 810                 815

Ile Gln Ala Ile Ala Asp Trp Val Pro Asp Gln Ile Tyr Gln Leu Pro
            820                 825                 830

Gly Lys Glu Val Val Thr Ala Thr Arg Thr Asp Gly Ala Gly Arg Lys
        835                 840                 845

Ile Ala Asp Ala Ile Asp His Ser Leu Tyr Val Ala Asn Ser Lys
    850                 855                 860

Ser Ser Gly Arg Asp Tyr Gln Ala Gln Tyr Gly Gly Glu Phe Leu Ala
865                 870                 875                 880
```

Glu Leu Lys Ala Lys Tyr Pro Lys Met Phe Thr Glu Asn Met Ile Ser
            885                 890                 895

Thr Gly Lys Pro Ile Asp Asp Ser Val Lys Leu Lys Gln Trp Lys Ala
        900                 905                 910

Lys Tyr Phe Asn Gly Thr Asn Val Leu Asp Arg Gly Val Gly Tyr Val
            915                 920                 925

Leu Ser Asp Glu Ala Thr Gly Lys Tyr Phe Val Thr Lys Glu Gly
930                 935                 940

Asn Phe Ile Pro Leu Gln Leu Thr Gly Asn Glu Lys Ala Val Thr Gly
945                 950                 955                 960

Phe Ser Asn Asp Gly Lys Gly Ile Thr Tyr Phe Gly Thr Ser Gly Asn
            965                 970                 975

Gln Ala Lys Ser Ala Phe Val Thr Phe Asn Gly Asn Thr Tyr Tyr Phe
            980                 985                 990

Asp Ala Arg Gly His Met Val Thr Asn Gly Glu Tyr Ser Pro Asn Gly
            995                 1000                1005

Lys Asp Val Tyr Arg Phe Leu Pro Asn Gly Ile Met Leu Ser Asn
    1010                1015                1020

Ala Phe Tyr Val Asp Ala Asn Gly Asn Thr Tyr Leu Tyr Asn Tyr
    1025                1030                1035

Lys Gly Gln Met Tyr Lys Gly Gly Tyr Thr Lys Phe Asp Val Thr
    1040                1045                1050

Glu Thr Asp Lys Asp Gly Asn Glu Ser Lys Val Val Lys Phe Arg
    1055                1060                1065

Tyr Phe Thr Asn Glu Gly Val Met Ala Lys Gly Leu Thr Val Ile
    1070                1075                1080

Asp Gly Ser Thr Gln Tyr Phe Gly Glu Asp Gly Phe Gln Thr Lys
    1085                1090                1095

Asp Lys Leu Ala Thr Tyr Lys Gly Lys Thr Tyr Phe Glu Ala
    1100                1105                1110

His Thr Gly Asn Ala Ile Lys Asn Thr Trp Arg Asn Ile Asp Gly
    1115                1120                1125

Lys Trp Tyr His Phe Asp Glu Asn Gly Val Ala Ala Thr Gly Ala
    1130                1135                1140

Gln Val Ile Asn Gly Gln Lys Leu Tyr Phe Asn Glu Asp Gly Ser
    1145                1150                1155

Gln Val Lys Gly Gly Val Val Lys Asn Ala Asp Gly Thr Tyr Ser
    1160                1165                1170

Lys Tyr Lys Glu Gly Ser Gly Glu Leu Val Thr Asn Glu Phe Phe
    1175                1180                1185

Thr Thr Asp Gly Asn Val Trp Tyr Tyr Ala Gly Ala Asp Gly Lys
    1190                1195                1200

Thr Val Thr Gly Ala Gln Val Ile Asn Gly Gln His Leu Tyr Phe
    1205                1210                1215

Lys Glu Asp Gly Ser Gln Val Lys Gly Gly Val Val Lys Asn Ala
    1220                1225                1230

Asp Gly Thr Tyr Ser Lys Tyr Asp Ala Ala Thr Gly Glu Arg Leu
    1235                1240                1245

Thr Asn Glu Phe Phe Thr Thr Gly Asp Asn Asn Trp Tyr Tyr Ile
    1250                1255                1260

Gly Ser Asn Gly Lys Thr Val Thr Gly Glu Val Lys Ile Gly Ala
    1265                1270                1275

Asp Thr Tyr Tyr Phe Ala Lys Asp Gly Lys Gln Val Lys Gly Gln

```
                        1280                1285                1290
Thr Val Thr Ala Gly Asn Gly Arg Ile Ser Tyr Tyr Tyr Gly Asp
            1295                1300                1305
Ser Gly Lys Lys Ala Ile Ser Thr Trp Ile Glu Ile Gln Pro Gly
            1310                1315                1320
Ile Tyr Val Tyr Phe Asp Lys Thr Gly Ile Ala Tyr Pro Pro Arg
            1325                1330                1335
Val Leu Asn
    1340

<210> SEQ ID NO 3
<211> LENGTH: 1341
<212> TYPE: PRT
<213> ORGANISM: Streptococcus salivarius SK126

<400> SEQUENCE: 3

Met Ile Asp Gly Lys Tyr Tyr Tyr Val Asn Glu Asp Gly Ser His Lys
1               5                   10                  15

Glu Asn Phe Ala Ile Thr Val Asn Gly Gln Leu Leu Tyr Phe Gly Lys
                20                  25                  30

Asp Gly Ala Leu Thr Ser Ser Thr Tyr Ser Phe Thr Pro Gly Thr
            35                  40                  45

Thr Asn Ile Val Asp Gly Phe Ser Ile Asn Asn Arg Ala Tyr Asp Ser
        50                  55                  60

Ser Glu Ala Ser Phe Glu Leu Ile Asp Gly Tyr Leu Thr Ala Asp Ser
65              70                  75                  80

Trp Tyr Arg Pro Ala Ser Ile Ile Lys Asp Gly Val Thr Trp Gln Ala
                85                  90                  95

Ser Thr Ala Glu Asp Phe Arg Pro Leu Leu Met Ala Trp Trp Pro Asn
            100                 105                 110

Val Asp Thr Gln Val Asn Tyr Leu Asn Tyr Met Ser Lys Val Phe Asn
        115                 120                 125

Leu Asp Ala Lys Tyr Ser Ser Thr Asp Lys Gln Glu Thr Leu Lys Val
    130                 135                 140

Ala Ala Lys Asp Ile Gln Ile Lys Ile Glu Gln Lys Ile Gln Ala Glu
145                 150                 155                 160

Lys Ser Thr Gln Trp Leu Arg Glu Thr Ile Ser Ala Phe Val Lys Thr
                165                 170                 175

Gln Pro Gln Trp Asn Lys Glu Thr Glu Asn Tyr Ser Lys Gly Gly Gly
            180                 185                 190

Glu Asp His Leu Gln Gly Gly Ala Leu Leu Tyr Val Asn Asp Ser Arg
        195                 200                 205

Thr Pro Trp Ala Asn Ser Asp Tyr Arg Arg Leu Asn Arg Thr Ala Thr
    210                 215                 220

Asn Gln Thr Gly Thr Ile Asp Lys Ser Ile Leu Asp Glu Gln Ser Asp
225                 230                 235                 240

Pro Asn His Met Gly Gly Phe Asp Phe Leu Leu Ala Asn Asp Val Asp
                245                 250                 255

Leu Ser Asn Pro Val Val Gln Ala Glu Gln Leu Asn Gln Ile His Tyr
            260                 265                 270

Leu Met Asn Trp Gly Ser Ile Val Met Gly Asp Lys Asp Ala Asn Phe
        275                 280                 285

Asp Gly Ile Arg Val Asp Ala Val Asp Asn Val Asp Ala Asp Met Leu
    290                 295                 300
```

-continued

Gln Leu Tyr Thr Asn Tyr Phe Arg Glu Tyr Tyr Gly Val Asn Lys Ser
305                 310                 315                 320

Glu Ala Asn Ala Leu Ala His Ile Ser Val Leu Glu Ala Trp Ser Leu
            325                 330                 335

Asn Asp Asn His Tyr Asn Asp Lys Thr Asp Gly Ala Ala Leu Ala Met
            340                 345                 350

Glu Asn Lys Gln Arg Leu Ala Leu Leu Phe Ser Leu Ala Lys Pro Ile
            355                 360                 365

Lys Glu Arg Thr Pro Ala Val Ser Pro Leu Tyr Asn Asn Thr Phe Asn
            370                 375                 380

Thr Thr Gln Arg Asp Glu Lys Thr Asp Trp Ile Asn Lys Asp Gly Ser
385                 390                 395                 400

Lys Ala Tyr Asn Glu Asp Gly Thr Val Lys Gln Ser Thr Ile Gly Lys
            405                 410                 415

Tyr Asn Glu Lys Tyr Gly Asp Ala Ser Gly Asn Tyr Val Phe Ile Arg
            420                 425                 430

Ala His Asp Asn Asn Val Gln Asp Ile Ile Ala Glu Ile Ile Lys Lys
            435                 440                 445

Glu Ile Asn Pro Lys Ser Asp Gly Phe Thr Ile Thr Asp Ala Glu Met
450                 455                 460

Lys Gln Ala Phe Glu Ile Tyr Asn Lys Asp Met Leu Ser Ser Asp Lys
465                 470                 475                 480

Lys Tyr Thr Leu Asn Asn Ile Pro Ala Ala Tyr Ala Val Met Leu Gln
            485                 490                 495

Asn Met Glu Thr Ile Thr Arg Val Tyr Tyr Gly Asp Leu Tyr Thr Asp
            500                 505                 510

Asp Gly His Tyr Met Glu Thr Lys Ser Pro Tyr Tyr Asp Thr Ile Val
            515                 520                 525

Asn Leu Met Lys Ser Arg Ile Lys Tyr Val Ser Gly Gly Gln Ala Gln
            530                 535                 540

Arg Ser Tyr Trp Leu Pro Thr Asp Gly Lys Met Asp Asn Ser Asp Val
545                 550                 555                 560

Glu Leu Tyr Arg Thr Asn Glu Val Tyr Thr Ser Val Arg Tyr Gly Lys
            565                 570                 575

Asp Ile Met Thr Ala Asn Asp Thr Glu Gly Ser Lys Tyr Ser Arg Thr
            580                 585                 590

Ser Gly Gln Val Thr Leu Val Ala Asn Asn Pro Lys Leu Thr Leu Asp
            595                 600                 605

Gln Ser Ala Lys Leu Asn Val Glu Met Gly Lys Ile His Ala Asn Gln
            610                 615                 620

Lys Tyr Arg Ala Leu Ile Val Gly Thr Ala Asp Gly Ile Lys Asn Phe
625                 630                 635                 640

Thr Ser Asp Ala Asp Ala Ile Ala Ala Gly Tyr Val Lys Glu Thr Asp
            645                 650                 655

Ser Asn Gly Val Leu Thr Phe Gly Ala Asn Asp Ile Lys Gly Tyr Glu
            660                 665                 670

Thr Phe Asp Met Ser Gly Phe Val Ala Val Trp Val Pro Val Gly Ala
            675                 680                 685

Ser Asp Asp Gln Asp Ile Arg Val Ala Pro Ser Thr Glu Ala Lys Lys
            690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp

-continued

```
               725                 730                 735
Pro Ser Val Tyr Thr Asn Arg Lys Ile Ala Glu Asn Val Asp Leu Phe
            740                 745                 750

Lys Ser Trp Gly Val Thr Ser Phe Glu Met Ala Pro Gln Phe Val Ser
            755                 760                 765

Ala Asp Asp Gly Thr Phe Leu Asp Ser Val Ile Gln Asn Gly Tyr Ala
            770                 775                 780

Phe Ala Asp Arg Tyr Asp Leu Ala Met Ser Lys Asn Asn Lys Tyr Gly
785                 790                 795                 800

Ser Lys Glu Asp Leu Arg Asp Ala Leu Lys Ala Leu His Lys Ala Gly
            805                 810                 815

Ile Gln Ala Ile Ala Asp Trp Val Pro Asp Gln Ile Tyr Gln Leu Pro
            820                 825                 830

Gly Lys Glu Val Val Thr Ala Thr Arg Thr Asp Gly Ala Gly Arg Lys
            835                 840                 845

Ile Ala Asp Ala Ile Ile Asp His Ser Leu Tyr Val Ala Asn Thr Lys
            850                 855                 860

Ser Ser Gly Lys Asp Tyr Gln Ala Lys Tyr Gly Gly Glu Phe Leu Ala
865                 870                 875                 880

Glu Leu Lys Ala Lys Tyr Pro Glu Met Phe Lys Val Asn Met Ile Ser
            885                 890                 895

Thr Gly Lys Pro Ile Asp Asp Ser Val Lys Leu Lys Gln Trp Lys Ala
            900                 905                 910

Glu Tyr Phe Asn Gly Thr Asn Val Leu Glu Arg Gly Val Gly Tyr Val
            915                 920                 925

Leu Ser Asp Glu Ala Thr Gly Lys Tyr Phe Thr Val Thr Lys Asp Gly
            930                 935                 940

Asn Phe Ile Pro Leu Gln Leu Thr Gly Asn Glu Lys Val Val Thr Gly
945                 950                 955                 960

Phe Ser Asn Asp Gly Lys Gly Ile Thr Tyr Phe Gly Thr Ser Gly Thr
            965                 970                 975

Gln Ala Lys Ser Ala Phe Val Thr Phe Asn Gly Asn Thr Tyr Tyr Phe
            980                 985                 990

Asp Ala Arg Gly His Met Val Thr Asn Gly Glu Tyr Ser Pro Asn Gly
            995                 1000                1005

Lys Asp Val Tyr Arg Phe Leu Pro Asn Gly Ile Met Leu Ser Asn
            1010                1015                1020

Ala Phe Tyr Val Asp Ala Asn Gly Asn Thr Tyr Leu Tyr Asn Ser
            1025                1030                1035

Lys Gly Gln Met Tyr Lys Gly Gly Tyr Thr Lys Phe Asp Val Thr
            1040                1045                1050

Glu Thr Asp Lys Asp Gly Lys Glu Ser Lys Val Val Lys Phe Arg
            1055                1060                1065

Tyr Phe Thr Asn Glu Gly Val Met Ala Lys Gly Val Thr Val Ile
            1070                1075                1080

Asp Gly Phe Thr Gln Tyr Phe Gly Glu Asp Gly Phe Gln Ala Lys
            1085                1090                1095

Asp Lys Leu Val Thr Phe Lys Gly Lys Thr Tyr Tyr Phe Asp Ala
            1100                1105                1110

His Thr Gly Asn Ala Ile Lys Asp Thr Trp Arg Asn Ile Asn Gly
            1115                1120                1125

Lys Trp Tyr His Phe Asp Ala Asn Gly Val Ala Ala Thr Gly Ala
            1130                1135                1140
```

Gln Val Ile Asn Gly Gln Lys Leu Tyr Phe Asn Glu Asp Gly Ser
    1145                1150                1155

Gln Val Lys Gly Gly Val Val Lys Asn Ala Asp Gly Thr Tyr Ser
    1160                1165                1170

Lys Tyr Lys Glu Gly Ser Gly Glu Leu Val Thr Asn Glu Phe Phe
    1175                1180                1185

Thr Thr Asp Gly Asn Val Trp Tyr Tyr Ala Gly Ala Asn Gly Lys
    1190                1195                1200

Thr Val Thr Gly Ala Gln Val Ile Asn Gly Gln His Leu Tyr Phe
    1205                1210                1215

Asn Ala Asp Gly Ser Gln Val Lys Gly Gly Val Val Lys Asn Ala
    1220                1225                1230

Asp Gly Thr Tyr Ser Lys Tyr Asp Ala Ser Thr Gly Glu Arg Leu
    1235                1240                1245

Thr Asn Glu Phe Phe Thr Thr Gly Asp Asn Asn Trp Tyr Tyr Ile
    1250                1255                1260

Gly Ala Asn Gly Lys Ser Val Thr Gly Glu Val Lys Ile Gly Asp
    1265                1270                1275

Asp Thr Tyr Phe Phe Ala Lys Asp Gly Lys Gln Val Lys Gly Gln
    1280                1285                1290

Thr Val Ser Ala Gly Asn Gly Arg Ile Ser Tyr Tyr Tyr Gly Asp
    1295                1300                1305

Ser Gly Lys Arg Ala Val Ser Thr Trp Ile Glu Ile Gln Pro Gly
    1310                1315                1320

Val Tyr Val Tyr Phe Asp Lys Asn Gly Ile Ala Tyr Pro Pro Arg
    1325                1330                1335

Val Leu Asn
    1340

<210> SEQ ID NO 4
<211> LENGTH: 1340
<212> TYPE: PRT
<213> ORGANISM: Streptococcus salivarius PS4

<400> SEQUENCE: 4

Met Ile Asp Gly Lys Tyr Tyr Val Asn Lys Asp Gly Ser His Lys
1               5                   10                  15

Glu Asn Phe Ala Ile Thr Val Asn Gly Gln Leu Leu Tyr Phe Gly Lys
                20                  25                  30

Asp Gly Ala Leu Thr Ser Ser Thr Tyr Ser Phe Thr Gln Gly Thr
            35                  40                  45

Thr Asn Ile Val Asp Gly Phe Ser Lys Asn Asn Arg Ala Tyr Asp Ser
    50                  55                  60

Ser Glu Ala Ser Phe Glu Leu Ile Asp Gly Tyr Leu Thr Ala Asp Ser
65                  70                  75                  80

Trp Tyr Arg Pro Val Ser Ile Ile Lys Asp Gly Val Thr Trp Gln Ala
                85                  90                  95

Ser Thr Lys Glu Asp Phe Arg Pro Leu Leu Met Ala Trp Trp Pro Asn
            100                 105                 110

Val Asp Thr Gln Val Asn Tyr Leu Asn Tyr Met Ser Lys Val Phe Asn
            115                 120                 125

Leu Asp Ala Lys Tyr Thr Ser Thr Asp Lys Gln Val Asp Leu Asn Arg
        130                 135                 140

Ala Ala Lys Asp Ile Gln Val Lys Ile Glu Gln Lys Ile Gln Ala Glu

```
            145                 150                 155                 160
Lys Ser Thr Gln Trp Leu Arg Glu Ala Ile Ser Ala Phe Val Lys Thr
                    165                 170                 175
Gln Pro Gln Trp Asn Lys Glu Thr Glu Asn Phe Ser Lys Gly Gly
                    180                 185                 190
Glu Asp His Leu Gln Gly Gly Ala Leu Leu Tyr Val Asn Asp Pro Arg
                    195                 200                 205
Thr Pro Trp Ala Asn Ser Asn Tyr Arg Leu Leu Asn Arg Thr Ala Thr
                    210                 215                 220
Asn Gln Thr Gly Thr Ile Asp Lys Ser Val Leu Asp Glu Gln Ser Asp
225                 230                 235                 240
Pro Asn His Met Gly Gly Phe Asp Phe Leu Leu Ala Asn Asp Val Asp
                    245                 250                 255
Thr Ser Asn Pro Val Val Gln Ala Glu Gln Leu Asn Gln Ile His Tyr
                    260                 265                 270
Leu Met Asn Trp Gly Ser Ile Val Met Gly Asp Lys Asp Ala Asn Phe
                    275                 280                 285
Asp Gly Ile Arg Val Asp Ala Val Asp Asn Val Asp Ala Asp Met Leu
                    290                 295                 300
Gln Leu Tyr Thr Asn Tyr Phe Arg Glu Tyr Tyr Gly Val Asn Lys Ser
305                 310                 315                 320
Glu Ala Asn Ala Leu Ala His Ile Ser Val Leu Glu Ala Trp Ser Leu
                    325                 330                 335
Asn Asp Asn His Tyr Asn Asp Lys Thr Asp Gly Ala Ala Leu Ala Met
                    340                 345                 350
Glu Asn Lys Gln Arg Leu Ala Leu Leu Phe Ser Leu Ala Lys Pro Ile
                    355                 360                 365
Lys Glu Arg Thr Pro Ala Val Ser Pro Leu Tyr Asn Asn Thr Phe Asn
                    370                 375                 380
Thr Thr Gln Arg Asp Glu Lys Thr Asp Trp Ile Asn Lys Asp Gly Ser
385                 390                 395                 400
Lys Ala Tyr Asn Glu Asp Gly Thr Val Lys Gln Ser Thr Ile Gly Lys
                    405                 410                 415
Tyr Asn Glu Lys Tyr Gly Asp Ala Ser Gly Asn Tyr Val Phe Ile Arg
                    420                 425                 430
Ala His Asp Asn Val Gln Asp Ile Ile Ala Glu Ile Ile Lys Lys
                    435                 440                 445
Glu Ile Asn Pro Lys Ser Asp Gly Phe Thr Ile Thr Asp Ala Glu Met
450                 455                 460
Lys Lys Ala Phe Glu Ile Tyr Asn Lys Asp Met Leu Ser Ser Asp Lys
465                 470                 475                 480
Lys Tyr Thr Leu Asn Asn Ile Pro Ala Ala Tyr Ala Val Met Leu Gln
                    485                 490                 495
Asn Met Glu Thr Ile Thr Arg Val Tyr Tyr Gly Asp Leu Tyr Thr Asp
                    500                 505                 510
Asp Gly His Tyr Met Glu Thr Lys Ser Pro Tyr Tyr Asp Thr Ile Val
                    515                 520                 525
Asn Leu Met Lys Asn Arg Ile Lys Tyr Val Ser Gly Gly Gln Ala Gln
                    530                 535                 540
Arg Ser Tyr Trp Leu Pro Thr Asp Gly Lys Met Asp Lys Ser Asp Val
545                 550                 555                 560
Glu Leu Tyr Arg Thr Asn Glu Val Tyr Thr Ser Val Arg Tyr Gly Lys
                    565                 570                 575
```

```
Asp Ile Met Thr Ala Asp Asp Thr Gln Gly Ser Lys Tyr Ser Arg Thr
            580                 585                 590

Ser Gly Gln Val Thr Leu Val Val Asn Asn Pro Lys Leu Ser Leu Asp
        595                 600                 605

Lys Ser Ala Lys Leu Asp Val Glu Met Gly Lys Ile His Ala Asn Gln
        610                 615                 620

Lys Tyr Arg Ala Leu Ile Val Gly Thr Pro Asn Gly Ile Lys Asn Phe
625                 630                 635                 640

Thr Ser Asp Ala Glu Ala Ile Ala Ala Gly Tyr Val Lys Glu Thr Asp
                645                 650                 655

Gly Asn Gly Val Leu Thr Phe Gly Ala Asn Asp Ile Lys Gly Tyr Glu
            660                 665                 670

Thr Phe Asp Met Ser Gly Phe Val Ala Val Trp Val Pro Val Gly Ala
        675                 680                 685

Ser Asp Asp Gln Asp Ile Arg Val Ala Ala Ser Thr Ala Ala Lys Lys
        690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp
                725                 730                 735

Pro Ser Val Tyr Thr Asn Arg Lys Ile Ala Glu Asn Val Asp Leu Phe
            740                 745                 750

Lys Ser Trp Gly Val Thr Ser Phe Glu Met Ala Pro Gln Phe Val Ser
        755                 760                 765

Ala Asp Asp Gly Thr Phe Leu Asp Ser Val Ile Gln Asn Gly Tyr Ala
        770                 775                 780

Phe Ala Asp Arg Tyr Asp Leu Ala Met Ser Lys Asn Asn Lys Tyr Gly
785                 790                 795                 800

Ser Lys Glu Asp Leu Arg Asn Ala Leu Lys Ala Leu His Lys Ala Gly
                805                 810                 815

Ile Gln Ala Ile Ala Asp Trp Val Pro Asp Gln Ile Tyr Gln Leu Pro
            820                 825                 830

Gly Lys Glu Val Val Thr Ala Thr Arg Thr Asp Gly Ala Gly Arg Lys
        835                 840                 845

Ile Ser Asp Ala Ile Ile Asp His Ser Leu Tyr Val Ala Asn Ser Lys
        850                 855                 860

Ser Ser Gly Lys Asp Tyr Gln Ala Lys Tyr Gly Gly Glu Phe Leu Ala
865                 870                 875                 880

Glu Leu Lys Ala Lys Tyr Pro Glu Met Phe Lys Val Asn Met Ile Ser
                885                 890                 895

Thr Gly Lys Pro Ile Asp Asp Ser Val Lys Leu Lys Gln Trp Lys Ala
            900                 905                 910

Glu Tyr Phe Asn Gly Thr Asn Val Leu Asp Arg Gly Val Gly Tyr Val
        915                 920                 925

Leu Ser Asp Glu Ala Thr Gly Lys Tyr Phe Thr Val Thr Lys Glu Gly
        930                 935                 940

Asn Phe Ile Pro Leu Gln Leu Lys Gly Asn Glu Lys Val Ile Thr Gly
945                 950                 955                 960

Phe Ser Ser Asp Gly Lys Gly Ile Thr Tyr Phe Gly Thr Ser Gly Asn
                965                 970                 975

Gln Ala Lys Ser Ala Phe Val Thr Phe Asn Gly Asn Thr Tyr Tyr Phe
            980                 985                 990
```

```
Asp Ala Arg Gly His Met Val Thr Asn Gly Glu Tyr Ser Pro Asn Gly
            995                 1000                1005

Lys Asp Val Tyr Arg Phe Leu Pro Asn Gly Ile Met Leu Ser Asn
    1010                1015                1020

Ala Phe Tyr Val Asp Gly Asn Gly Asn Thr Tyr Leu Tyr Asn Ser
    1025                1030                1035

Lys Gly Gln Met Tyr Lys Gly Gly Tyr Ser Lys Phe Asp Val Thr
    1040                1045                1050

Glu Thr Lys Asp Gly Lys Glu Ser Lys Val Val Lys Phe Arg Tyr
    1055                1060                1065

Phe Thr Asn Glu Gly Val Met Ala Lys Gly Val Thr Val Val Asp
    1070                1075                1080

Gly Phe Thr Gln Tyr Phe Asn Glu Asp Gly Ile Gln Ser Lys Asp
    1085                1090                1095

Glu Leu Val Thr Tyr Asn Gly Lys Thr Tyr Tyr Phe Glu Ala His
    1100                1105                1110

Thr Gly Asn Ala Ile Lys Asn Thr Trp Arg Asn Ile Lys Gly Lys
    1115                1120                1125

Trp Tyr His Phe Asp Ala Asn Gly Val Ala Ala Thr Gly Ala Gln
    1130                1135                1140

Val Ile Asn Gly Gln His Leu Tyr Phe Asn Glu Asp Gly Ser Gln
    1145                1150                1155

Val Lys Gly Gly Val Val Lys Asn Ala Asp Gly Thr Phe Ser Lys
    1160                1165                1170

Tyr Lys Asp Gly Ser Gly Asp Leu Val Val Asn Glu Phe Phe Thr
    1175                1180                1185

Thr Gly Asp Asn Val Trp Tyr Tyr Ala Gly Ala Asn Gly Lys Thr
    1190                1195                1200

Val Thr Gly Ala Gln Val Ile Asn Gly Gln His Leu Phe Phe Lys
    1205                1210                1215

Glu Asp Gly Ser Gln Val Lys Gly Asp Phe Val Lys Asn Ser Asp
    1220                1225                1230

Gly Thr Tyr Ser Lys Tyr Asp Ala Ala Ser Gly Glu Arg Leu Thr
    1235                1240                1245

Asn Glu Phe Phe Thr Thr Gly Asp Asn His Trp Tyr Tyr Ile Gly
    1250                1255                1260

Ala Asn Gly Lys Thr Val Thr Gly Glu Val Lys Ile Gly Asp Asp
    1265                1270                1275

Thr Tyr Phe Phe Ala Lys Asp Gly Lys Gln Leu Lys Gly Gln Ile
    1280                1285                1290

Val Thr Thr Arg Ser Gly Arg Ile Ser Tyr Tyr Phe Gly Asp Ser
    1295                1300                1305

Gly Lys Lys Ala Ile Ser Thr Trp Val Glu Ile Gln Pro Gly Val
    1310                1315                1320

Phe Val Phe Phe Asp Lys Asn Gly Leu Ala Tyr Pro Pro Glu Asn
    1325                1330                1335

Met Asn
    1340

<210> SEQ ID NO 5
<211> LENGTH: 1340
<212> TYPE: PRT
<213> ORGANISM: Unknown
<220> FEATURE:
<223> OTHER INFORMATION: unknown Streptococcus sp. C150
```

<400> SEQUENCE: 5

```
Met Ile Asp Gly Lys Tyr Tyr Tyr Val Asn Glu Asp Gly Ser His Lys
1               5                   10                  15

Glu Asn Phe Ala Ile Thr Val Asn Gly Gln Leu Leu Tyr Phe Gly Lys
            20                  25                  30

Asp Gly Ala Leu Thr Ser Ser Thr Tyr Ser Phe Thr Gln Gly Thr
        35                  40                  45

Thr Asn Ile Val Asp Gly Phe Ser Ile Asn Asn Arg Ala Tyr Asp Ser
    50                  55                  60

Ser Glu Ala Ser Phe Glu Leu Ile Asp Gly Tyr Leu Thr Ala Asp Ser
65                  70                  75                  80

Trp Tyr Arg Pro Ala Ser Ile Ile Lys Asp Gly Val Thr Trp Gln Ala
                85                  90                  95

Ser Thr Ala Glu Asp Phe Arg Pro Leu Leu Met Ala Trp Trp Pro Asn
            100                 105                 110

Val Asp Thr Gln Val Asn Tyr Leu Asn Tyr Met Ser Lys Val Phe Asn
        115                 120                 125

Leu Asp Ala Lys Tyr Ser Ser Thr Asp Lys Gln Glu Thr Leu Lys Val
130                 135                 140

Ala Ala Lys Asp Ile Gln Ile Lys Ile Glu Gln Lys Ile Gln Ala Glu
145                 150                 155                 160

Lys Ser Thr Gln Trp Leu Arg Glu Thr Ile Ser Ala Phe Val Lys Thr
                165                 170                 175

Gln Pro Gln Trp Asn Lys Glu Thr Glu Asn Tyr Ser Lys Gly Gly Gly
            180                 185                 190

Glu Asp His Leu Gln Gly Gly Ala Leu Leu Tyr Val Asn Asp Ser Arg
        195                 200                 205

Thr Pro Trp Ala Asn Ser Asn Tyr Arg Leu Leu Asn Arg Thr Ala Thr
    210                 215                 220

Asn Gln Thr Gly Thr Ile Asp Lys Ser Ile Leu Asp Glu Gln Ser Asp
225                 230                 235                 240

Pro Asn His Met Gly Gly Phe Asp Phe Leu Leu Ala Asn Asp Val Asp
                245                 250                 255

Leu Ser Asn Pro Val Val Gln Ala Glu Gln Leu Asn Gln Ile His Tyr
            260                 265                 270

Leu Met Asn Trp Gly Ser Ile Val Met Gly Asp Lys Asp Ala Asn Phe
        275                 280                 285

Asp Gly Ile Arg Val Asp Ala Val Asp Asn Val Asp Ala Asp Met Leu
    290                 295                 300

Gln Leu Tyr Thr Asn Tyr Phe Arg Glu Tyr Tyr Gly Val Asn Lys Ser
305                 310                 315                 320

Glu Ala Asn Ala Leu Ala His Ile Ser Val Leu Glu Ala Trp Ser Leu
                325                 330                 335

Asn Asp Asn His Tyr Asn Asp Lys Thr Asp Val Ala Ala Leu Ala Met
            340                 345                 350

Glu Asn Lys Gln Arg Leu Ala Leu Leu Phe Ser Leu Ala Lys Pro Ile
        355                 360                 365

Lys Glu Arg Thr Pro Ala Val Ser Pro Leu Tyr Asn Asn Thr Phe Asn
    370                 375                 380

Thr Thr Gln Arg Asp Glu Lys Thr Asp Trp Ile Asn Lys Asp Gly Ser
385                 390                 395                 400

Lys Ala Tyr Asn Glu Asp Gly Thr Val Lys Lys Ser Thr Ile Gly Lys
```

-continued

```
            405                 410                 415
Tyr Asn Glu Lys Tyr Gly Asp Ala Ser Gly Asn Tyr Val Phe Ile Arg
            420                 425                 430
Ala His Asp Asn Asn Val Gln Asp Ile Ile Ala Glu Ile Ile Lys Lys
            435                 440                 445
Glu Ile Asn Glu Lys Ser Asp Gly Phe Thr Ile Thr Asp Ser Glu Met
450                 455                 460
Lys Arg Ala Phe Glu Ile Tyr Asn Lys Asp Met Leu Ser Asn Asp Lys
465                 470                 475                 480
Lys Tyr Thr Leu Asn Asn Ile Pro Ala Ala Tyr Ala Val Met Leu Gln
                485                 490                 495
Asn Met Glu Thr Ile Thr Arg Val Tyr Tyr Gly Asp Leu Tyr Thr Asp
                500                 505                 510
Asp Gly Asn Tyr Met Glu Ala Lys Ser Pro Tyr Tyr Asp Thr Ile Val
                515                 520                 525
Asn Leu Met Lys Ser Arg Ile Lys Tyr Val Ser Gly Gly Gln Ala Gln
            530                 535                 540
Arg Ser Tyr Trp Leu Pro Thr Asp Gly Lys Met Asp Lys Ser Asp Val
545                 550                 555                 560
Glu Leu Tyr Arg Thr Asn Glu Val Tyr Thr Ser Val Arg Tyr Gly Lys
                565                 570                 575
Asp Ile Met Thr Ala Asp Asp Thr Gln Gly Ser Lys Tyr Ser Arg Thr
            580                 585                 590
Ser Gly Gln Val Thr Leu Val Val Asn Asn Pro Lys Leu Thr Leu Asp
            595                 600                 605
Gln Ser Ala Lys Leu Asn Val Val Met Gly Lys Ile His Ala Asn Gln
    610                 615                 620
Lys Tyr Arg Ala Leu Ile Val Gly Thr Pro Asn Gly Ile Lys Asn Phe
625                 630                 635                 640
Thr Ser Asp Ala Glu Ala Ile Ala Ala Gly Tyr Val Lys Glu Thr Asp
                645                 650                 655
Gly Asn Gly Val Leu Thr Phe Gly Ala Asn Asp Ile Lys Gly Tyr Glu
            660                 665                 670
Thr Phe Asp Met Ser Gly Phe Val Ala Val Trp Val Pro Val Gly Ala
        675                 680                 685
Ser Asp Asp Gln Asp Ile Arg Val Ala Ala Ser Thr Ala Ala Lys Lys
    690                 695                 700
Glu Gly Glu Leu Thr Leu Lys Ala Thr Glu Ala Tyr Asp Ser Gln Leu
705                 710                 715                 720
Ile Tyr Glu Gly Phe Ser Asn Phe Gln Thr Ile Pro Asp Gly Ser Asp
                725                 730                 735
Pro Ser Val Tyr Thr Asn Arg Lys Ile Ala Glu Asn Val Asp Leu Phe
            740                 745                 750
Lys Ser Trp Gly Val Thr Ser Phe Glu Met Ala Pro Gln Phe Val Ser
            755                 760                 765
Ala Asp Asp Gly Thr Phe Leu Asp Ser Val Ile Gln Asn Gly Tyr Ala
    770                 775                 780
Phe Ala Asp Arg Tyr Asp Leu Ala Met Ser Lys Asn Asn Lys Tyr Gly
785                 790                 795                 800
Ser Lys Glu Asp Leu Arg Asn Ala Leu Lys Ala Leu His Lys Ala Gly
                805                 810                 815
Ile Gln Ala Ile Ala Asp Trp Val Pro Asp Gln Ile Tyr Gln Leu Pro
        820                 825                 830
```

-continued

Gly Lys Glu Val Val Thr Ala Thr Arg Thr Asp Gly Ala Gly Arg Lys
        835                 840                 845

Ile Ser Asp Ala Ile Ile Asp His Ser Leu Tyr Val Ala Asn Ser Lys
850                 855                 860

Ser Ser Gly Lys Asp Tyr Gln Ala Lys Tyr Gly Gly Glu Phe Leu Ala
865                 870                 875                 880

Glu Leu Lys Ala Lys Tyr Pro Glu Met Phe Lys Val Asn Met Ile Ser
            885                 890                 895

Thr Gly Lys Pro Ile Asp Asp Ser Val Lys Leu Lys Gln Trp Lys Ala
            900                 905                 910

Glu Tyr Phe Asn Gly Thr Asn Val Leu Asp Arg Gly Val Gly Tyr Val
            915                 920                 925

Leu Ser Asp Glu Ala Thr Gly Lys Tyr Phe Thr Val Thr Lys Glu Gly
930                 935                 940

Asn Phe Ile Pro Leu Gln Leu Lys Gly Asn Lys Lys Val Ile Thr Gly
945                 950                 955                 960

Phe Ser Ser Asp Gly Lys Gly Ile Thr Tyr Phe Gly Thr Ser Gly Asn
                965                 970                 975

Gln Ala Lys Ser Ala Phe Val Thr Phe Asn Gly Asn Thr Tyr Tyr Phe
            980                 985                 990

Asp Ala Arg Gly His Met Val Thr Asn Gly Glu Tyr Ser Pro Asn Gly
            995                 1000                1005

Lys Asp Val Tyr Arg Phe Leu Pro Asn Gly Ile Met Leu Ser Asn
    1010                1015                1020

Ala Phe Tyr Val Asp Gly Asn Gly Asn Thr Tyr Leu Tyr Asn Ser
    1025                1030                1035

Lys Gly Gln Met Tyr Lys Gly Gly Tyr Ser Lys Phe Asp Val Thr
    1040                1045                1050

Glu Thr Lys Asp Gly Lys Glu Ser Lys Val Val Lys Phe Arg Tyr
    1055                1060                1065

Phe Thr Asn Glu Gly Val Met Ala Lys Gly Val Thr Val Val Asp
    1070                1075                1080

Gly Phe Thr Gln Tyr Phe Asn Glu Asp Gly Ile Gln Ser Lys Asp
    1085                1090                1095

Glu Leu Val Thr Tyr Asn Gly Lys Thr Tyr Tyr Phe Glu Ala His
    1100                1105                1110

Thr Gly Asn Ala Ile Lys Asn Thr Trp Arg Asn Ile Lys Gly Lys
    1115                1120                1125

Trp Tyr His Phe Asp Ala Asn Gly Val Ala Ala Thr Gly Ala Gln
    1130                1135                1140

Val Ile Asn Gly Gln His Leu Tyr Phe Asn Glu Asp Gly Ser Gln
    1145                1150                1155

Val Lys Gly Ser Ile Val Lys Asn Ala Asp Gly Thr Phe Ser Lys
    1160                1165                1170

Tyr Lys Asp Ser Ser Gly Asp Leu Val Val Asn Glu Phe Phe Thr
    1175                1180                1185

Thr Gly Asp Asn Val Trp Tyr Tyr Ala Gly Ala Asn Gly Lys Thr
    1190                1195                1200

Val Thr Gly Ala Gln Val Ile Asn Gly Gln His Leu Phe Phe Lys
    1205                1210                1215

Glu Asp Gly Ser Gln Val Lys Gly Asp Phe Val Lys Asn Ser Asp
    1220                1225                1230

```
Gly Thr Tyr Ser Lys Tyr Asp Ala Ala Ser Gly Glu Arg Leu Thr
    1235                1240                1245

Asn Glu Phe Phe Thr Thr Gly Asp Asn His Trp Tyr Tyr Ile Gly
    1250                1255                1260

Ala Asn Gly Lys Thr Val Thr Gly Glu Val Lys Ile Gly Asp Asp
    1265                1270                1275

Thr Tyr Phe Phe Ala Lys Asp Gly Lys Gln Leu Lys Gly Gln Ile
    1280                1285                1290

Val Thr Thr Arg Ser Gly Arg Ile Ser Tyr Phe Gly Asp Ser
    1295                1300                1305

Gly Lys Lys Ala Ile Ser Thr Trp Val Glu Ile Gln Pro Gly Val
    1310                1315                1320

Phe Val Phe Phe Asp Lys Asn Gly Leu Ala Tyr Pro Pro Glu Asn
    1325                1330                1335

Met Asn
    1340

<210> SEQ ID NO 6
<211> LENGTH: 1447
<212> TYPE: PRT
<213> ORGANISM: Leuconostoc pseudomesenteroides

<400> SEQUENCE: 6

Asp Gln Asn Val Asn Asp Pro Ser Val Ala Thr Thr Gln Asn Val
1               5                   10                  15

Val Thr Asp Gln Asp Thr Ser Ile Asp Ala Ser Val Ala Thr Thr Val
            20                  25                  30

Asn Pro Asn Leu Asp Asp Thr Gln Ala Asp Asn Thr Asn Ile Gln Thr
        35                  40                  45

Pro Thr Asp Gln Asn Asp Glu Ser Lys Asp Thr Thr Pro Lys Val Glu
    50                  55                  60

Thr Gly Asp Thr Thr Asn Ser Gln Ser Thr Glu Ala Gln Glu Thr Thr
65                  70                  75                  80

Ala Gln Thr Asn Asn Asp Val Glu Thr Pro Gln Asn Ser Asp Ala Ala
                85                  90                  95

Ile Glu Thr Gly Leu Leu Thr Thr Asn Asn Gln Ile Arg Tyr Val Asn
            100                 105                 110

Pro Asp Gly Thr Val Leu Thr Gly Ala Tyr Lys Thr Ile Asn Gly Asn
        115                 120                 125

Thr Tyr Tyr Phe Asp Asp Ser Gly Val Ala Leu Val Gly Leu His
    130                 135                 140

Lys Ile Gly Asp Thr Leu Lys Gly Phe Ser Leu Asn Gly Val Gln Val
145                 150                 155                 160

Lys Gly Asp Tyr Leu Thr Ala Ala Asn Gly Asp Lys Tyr Tyr Phe Asp
                165                 170                 175

Ser Asn Gly Asn Ala Val Ser Gly Val Gln Gln Ile Asn Gly Lys Thr
            180                 185                 190

Tyr Tyr Phe Asp Ser Thr Gly Lys Leu Met Lys Gly Tyr Thr Ala Val
        195                 200                 205

Leu Asn Gly Val Val Thr Phe Phe Asn Ser Thr Gly Glu Ala Asp
    210                 215                 220

Asn Thr Asp Ala Ser Thr Ile Lys Thr Gly Val Thr Ile Asp Asn Ser
225                 230                 235                 240

Asp Tyr Thr Val His Asn Ala Ala Tyr Asp Asn Thr Ala Ala Ser Phe
                245                 250                 255
```

-continued

```
Asp Asn Ile Asn Gly Tyr Leu Thr Ala Glu Ser Trp Tyr Arg Pro Lys
                260                 265                 270

Glu Ile Leu Glu Asn Gly Glu Ser Trp Arg Pro Ser Thr Ala Glu Asp
            275                 280                 285

Lys Arg Pro Ile Leu Ile Thr Trp Gln Pro Asp Ile Val Thr Glu Val
290                 295                 300

Asn Tyr Leu Asn Met Met Ala Ala Asn Gly Leu Leu Ser Ile Asn Ala
305                 310                 315                 320

Pro Phe Thr Thr Ala Ser Asp Leu Ala Ile Met Asn Asp Ala Val Arg
                325                 330                 335

Ala Val Gln Lys Asn Ile Glu Met Arg Ile Ser Gln Glu Lys Ser Thr
            340                 345                 350

Asp Trp Leu Lys Ala Leu Met Thr Gln Phe Ile Asn Thr Gln Pro Gln
        355                 360                 365

Trp Asn Glu Val Ser Glu Ser Pro Ser Asn Asp His Leu Gln Gly Gly
    370                 375                 380

Ala Leu Thr Tyr Val Asn Ser Pro Leu Thr Pro Asp Ala Asn Ser Asn
385                 390                 395                 400

Phe Arg Leu Leu Asn Arg Thr Pro Thr Asn Gln Ser Gly Thr Thr Arg
                405                 410                 415

Tyr Asp Thr Asp Lys Ser Lys Gly Gly Phe Glu Leu Leu Leu Ala Asn
            420                 425                 430

Asp Val Asp Asn Ser Asn Pro Val Val Gln Ala Glu Gln Leu Asn Trp
        435                 440                 445

Leu Tyr Tyr Leu Met Asn Phe Gly Ser Ile Thr Ala Asn Asp Pro Thr
    450                 455                 460

Ala Asn Phe Asp Gly Ile Arg Val Asp Ala Val Asp Asn Val Asp Ala
465                 470                 475                 480

Asp Leu Leu Gln Ile Ala Ser Asp Tyr Phe Lys Leu Ala Tyr Gly Thr
                485                 490                 495

Ser Leu Ser Asp Thr Asn Ala Asn Gln His Leu Ser Ile Leu Glu Asp
            500                 505                 510

Trp Ser Ala Asn Asp Ala Glu Tyr Met Ser Lys Thr Gly Ser Asn Gln
        515                 520                 525

Leu Thr Met Asp Thr Tyr Thr Gln Gln Gln Leu Leu Phe Ser Leu Thr
    530                 535                 540

Lys Gln Val Gly Asn Arg Ala Asp Met Arg Arg Phe Leu Glu Tyr Phe
545                 550                 555                 560

Met Ile Asn Arg Ala Asn Asp Ser Thr Glu Asn Val Ala Thr Pro Asn
                565                 570                 575

Tyr Ser Phe Val Arg Ala His Asp Ser Glu Val Gln Thr Val Ile Ala
            580                 585                 590

Thr Ile Ile Lys Asp Leu His Pro Asp Val Val Asn Ser Leu Ala Pro
        595                 600                 605

Thr Gln Ala Gln Leu Glu Glu Ala Phe Ala Val Tyr Asn Ala Asp Met
    610                 615                 620

Asn Arg Val Asp Lys Gln Tyr Thr Gln Tyr Asn Met Pro Ser Ala Tyr
625                 630                 635                 640

Ala Met Leu Leu Thr Asn Lys Asp Thr Ile Pro Arg Val Tyr Tyr Gly
                645                 650                 655

Asp Leu Tyr Thr Asp Asp Gly Glu Tyr Met Gly Thr Gln Thr Pro Tyr
            660                 665                 670
```

-continued

Tyr Asp Ala Ile Val Asn Leu Leu Gln Ser Arg Val Lys Tyr Val Ala
        675                 680                 685

Gly Gly Gln Ser Met Ala Val Asp Gln His Asp Ile Leu Thr Ser Val
690                 695                 700

Arg Tyr Gly Lys Asn Leu Ala Asp Ala Asn Ala Thr Ser Asp Asp Leu
705                 710                 715                 720

Thr Ser Ile Asn Ser Gly Ile Gly Val Ile Val Ser Asn Asn Pro Asn
                725                 730                 735

Leu Ser Leu Ala Ser Gly Glu Thr Val Val Leu His Met Gly Ile Ala
            740                 745                 750

His Ala Asn Gln Val Tyr Arg Glu Ile Leu Glu Thr Thr Asp Asn Gly
        755                 760                 765

Ile Ala Asn Asn Thr Asp Ile Phe Lys Thr Thr Asp Ser Asn Gly Asp
770                 775                 780

Leu Ile Phe Thr Ala Ser Glu Ile His Gly Tyr Ser Asn Val Gln Val
785                 790                 795                 800

Ser Gly Phe Leu Ser Val Trp Ala Pro Lys Asp Ala Thr Asp Asp Gln
                805                 810                 815

Asp Val Arg Thr Ala Ala Ser Glu Ser Thr Ser Asn Asp Gly Asn Thr
            820                 825                 830

Leu His Ser Asn Ala Ala Leu Asp Ser Asn Leu Ile Tyr Glu Gly Phe
        835                 840                 845

Ser Asn Phe Gln Ser Thr Pro Gln Ser Glu Ser Glu Phe Ala Asn Val
850                 855                 860

Lys Ile Ala Ala Asn Val Asn Leu Phe Lys Ser Trp Gly Val Thr Ser
865                 870                 875                 880

Phe Gln Met Ala Pro Gln Tyr Arg Ser Ser Thr Asp Thr Ser Phe Leu
                885                 890                 895

Asp Ser Ile Ile Gln Asn Gly Tyr Ala Phe Thr Asp Arg Tyr Asp Leu
            900                 905                 910

Gly Phe Glu Thr Pro Thr Lys Tyr Gly Thr Asp Gln Gln Leu Arg Asp
        915                 920                 925

Ala Ile Lys Ala Leu His Ala Asn Gly Ile Gln Ala Met Ala Asp Phe
930                 935                 940

Val Pro Asp Gln Ile Tyr Asn Leu Pro Gln Thr Glu Leu Val Ser Val
945                 950                 955                 960

Ser Arg Thr Asp Ser Leu Gly Asn Gln Ser Ala Asn Ser Asn Ala Ala
                965                 970                 975

Asn Val Leu Tyr Val Ser His Thr Val Gly Gly Gly Tyr Gln Ser
            980                 985                 990

Lys Tyr Gly Gly Glu Phe Leu Ala Ile Ile Lys Ser Lys Tyr Pro Ser
        995                 1000                1005

Leu Phe Lys Thr Ile Gln Val Ser Thr Gly Leu Pro Ile Asp Asp
        1010                1015                1020

Ser Thr Lys Ile Lys Glu Trp Ser Ala Lys Tyr Phe Asn Gly Ser
        1025                1030                1035

Asn Ile Gln Gly Arg Gly Phe Gly Tyr Val Leu Ser Asp Gly Gly
        1040                1045                1050

Thr Gln Asn Tyr Phe Lys Val Ile Ser Asn Ser Thr Asp Asp Asp
        1055                1060                1065

Phe Leu Pro Asn Gln Leu Thr Gly Lys Pro Thr Met Thr Gly Phe
        1070                1075                1080

Glu Gln Thr Ser Lys Gly Ile Val Tyr Tyr Ser Lys Ser Gly Ile

```
                    1085                1090                1095
Gln Ala Lys Asn Gln Phe Val Lys Asp Asp Val Ser Gly Asn Tyr
            1100                1105                1110
Tyr Tyr Phe Asn Lys Asn Gly Leu Met Thr Val Gly Ser Lys Thr
            1115                1120                1125
Ile Asn Gly Lys Asn Tyr Met Phe Leu Pro Asn Gly Val Glu Leu
            1130                1135                1140
Arg Gly Ser Phe Leu Gln Thr Ala Asp Gly Thr Val Asn Tyr Tyr
            1145                1150                1155
Ala Thr Asn Gly Ala Gln Val Gln Asp Ser Tyr Val Thr Asp Thr
            1160                1165                1170
Glu Gly Asn Ser Tyr Tyr Phe Asp Gly Asp Gly Glu Met Val Thr
            1175                1180                1185
Gly Thr Tyr Thr Val Asp Gly His Ala Gln Tyr Phe Asp Val Asn
            1190                1195                1200
Gly Val Gln Thr Lys Gly Ala Ile Ile Thr Leu Gly Gly Val Gln
            1205                1210                1215
Arg Tyr Tyr Gln Ala Gly Asn Gly Asn Leu Ala Thr Asn Gln Tyr
            1220                1225                1230
Val Ser Tyr Asn Asn Ser Trp Tyr Tyr Ala Asn Thr Lys Gly Glu
            1235                1240                1245
Leu Val Thr Gly Val Gln Ser Ile Asn Gly Asn Val Gln Tyr Phe
            1250                1255                1260
Ala Ser Asn Gly Gln Gln Ile Lys Gly Gln Ile Val Val Thr Gly
            1265                1270                1275
Asn Gln Lys Ser Tyr Tyr Asp Ala Asn Thr Gly Asn Leu Ile Lys
            1280                1285                1290
Asn Asp Phe Leu Thr Pro Asp Gln Gly Lys Thr Trp Tyr Tyr Ala
            1295                1300                1305
Asp Gln Asp Gly Asn Leu Val Val Gly Ala Gln Glu Val Asn Gly
            1310                1315                1320
His Lys Leu Tyr Phe Asp Asn Gly Ile Gln Ile Lys Asp Gln
            1325                1330                1335
Ile Ile Ser Asn Asp Gly Gln Gln Tyr Tyr Gln Gly Gly Asn
            1340                1345                1350
Gly Asp Leu Val Thr Asn Arg Tyr Ile Ser Tyr Asn Asp Ser Trp
            1355                1360                1365
Tyr Tyr Ala Asp Ala Thr Gly Val Leu Val Thr Gly Gln Gln Ile
            1370                1375                1380
Ile Asn Gly Glu Thr Gln Tyr Phe Arg Thr Asp Gly Arg Gln Val
            1385                1390                1395
Lys Gly Gln Ile Ile Ala Asp Gly Asp Lys Gln His Tyr Tyr Asp
            1400                1405                1410
Ala Asp Ser Gly Asn Leu Val Lys Asn Asn Phe Val Thr Val Asp
            1415                1420                1425
Gln Gly Lys Thr Trp Tyr Tyr Ala Asp Gln Asp Gly Asn Leu Ser
            1430                1435                1440
Leu Val Asp Arg
            1445

<210> SEQ ID NO 7
<211> LENGTH: 1457
<212> TYPE: PRT
<213> ORGANISM: Artificial sequence
```

<220> FEATURE:
<223> OTHER INFORMATION: 0768 gtf mature protein with start codon and
       other added sequence

<400> SEQUENCE: 7

| | | | | | | | | | | | | | | |
|---|---|---|---|---|---|---|---|---|---|---|---|---|---|---|
| Met | Ala | Ser | Ala | Asp | Gln | Asn | Val | Asn | Asp | Pro | Ser | Val | Ala | Thr | Thr |
| 1 | | | | 5 | | | | | 10 | | | | | 15 | |
| Thr | Gln | Asn | Val | Val | Thr | Asp | Gln | Asp | Thr | Ser | Ile | Asp | Ala | Ser | Val |
| | | | 20 | | | | | 25 | | | | | 30 | | |
| Ala | Thr | Thr | Val | Asn | Pro | Asn | Leu | Asp | Asp | Thr | Gln | Ala | Asp | Asn | Thr |
| | | 35 | | | | | 40 | | | | | 45 | | | |
| Asn | Ile | Gln | Thr | Pro | Thr | Asp | Gln | Asn | Asp | Glu | Ser | Lys | Asp | Thr | Thr |
| | 50 | | | | | 55 | | | | | 60 | | | | |
| Pro | Lys | Val | Glu | Thr | Gly | Asp | Thr | Thr | Asn | Ser | Gln | Ser | Thr | Glu | Ala |
| 65 | | | | | 70 | | | | | 75 | | | | | 80 |
| Gln | Glu | Thr | Thr | Ala | Gln | Thr | Asn | Asn | Asp | Val | Glu | Thr | Pro | Gln | Asn |
| | | | | 85 | | | | | 90 | | | | | 95 | |
| Ser | Asp | Ala | Ala | Ile | Glu | Thr | Gly | Leu | Leu | Thr | Thr | Asn | Asn | Gln | Ile |
| | | | 100 | | | | | 105 | | | | | 110 | | |
| Arg | Tyr | Val | Asn | Pro | Asp | Gly | Thr | Val | Leu | Thr | Gly | Ala | Tyr | Lys | Thr |
| | | 115 | | | | | 120 | | | | | 125 | | | |
| Ile | Asn | Gly | Asn | Thr | Tyr | Tyr | Phe | Asp | Asp | Ser | Gly | Val | Ala | Leu |
| | 130 | | | | | 135 | | | | | 140 | | | | |
| Val | Gly | Leu | His | Lys | Ile | Gly | Asp | Thr | Leu | Lys | Gly | Phe | Ser | Leu | Asn |
| 145 | | | | | 150 | | | | | 155 | | | | | 160 |
| Gly | Val | Gln | Val | Lys | Gly | Asp | Tyr | Leu | Thr | Ala | Ala | Asn | Gly | Asp | Lys |
| | | | | 165 | | | | | 170 | | | | | 175 | |
| Tyr | Tyr | Phe | Asp | Ser | Asn | Gly | Asn | Ala | Val | Ser | Gly | Val | Gln | Gln | Ile |
| | | | 180 | | | | | 185 | | | | | 190 | | |
| Asn | Gly | Lys | Thr | Tyr | Tyr | Phe | Asp | Ser | Thr | Gly | Lys | Leu | Met | Lys | Gly |
| | | 195 | | | | | 200 | | | | | 205 | | | |
| Tyr | Thr | Ala | Val | Leu | Asn | Gly | Val | Val | Thr | Phe | Phe | Asn | Ser | Thr | Thr |
| | 210 | | | | | 215 | | | | | 220 | | | | |
| Gly | Glu | Ala | Asp | Asn | Thr | Asp | Ala | Ser | Thr | Ile | Lys | Thr | Gly | Val | Thr |
| 225 | | | | | 230 | | | | | 235 | | | | | 240 |
| Ile | Asp | Asn | Ser | Asp | Tyr | Thr | Val | His | Asn | Ala | Ala | Tyr | Asp | Asn | Thr |
| | | | | 245 | | | | | 250 | | | | | 255 | |
| Ala | Ala | Ser | Phe | Asp | Asn | Ile | Asn | Gly | Tyr | Leu | Thr | Ala | Glu | Ser | Trp |
| | | | 260 | | | | | 265 | | | | | 270 | | |
| Tyr | Arg | Pro | Lys | Glu | Ile | Leu | Glu | Asn | Gly | Glu | Ser | Trp | Arg | Pro | Ser |
| | | 275 | | | | | 280 | | | | | 285 | | | |
| Thr | Ala | Glu | Asp | Lys | Arg | Pro | Ile | Leu | Ile | Thr | Trp | Gln | Pro | Asp | Ile |
| | 290 | | | | | 295 | | | | | 300 | | | | |
| Val | Thr | Glu | Val | Asn | Tyr | Leu | Asn | Met | Met | Ala | Ala | Asn | Gly | Leu | Leu |
| 305 | | | | | 310 | | | | | 315 | | | | | 320 |
| Ser | Ile | Asn | Ala | Pro | Phe | Thr | Thr | Ala | Ser | Asp | Leu | Ala | Ile | Met | Asn |
| | | | | 325 | | | | | 330 | | | | | 335 | |
| Asp | Ala | Val | Arg | Ala | Val | Gln | Lys | Asn | Ile | Glu | Met | Arg | Ile | Ser | Gln |
| | | | 340 | | | | | 345 | | | | | 350 | | |
| Glu | Lys | Ser | Thr | Asp | Trp | Leu | Lys | Ala | Leu | Met | Thr | Gln | Phe | Ile | Asn |
| | | 355 | | | | | 360 | | | | | 365 | | | |
| Thr | Gln | Pro | Gln | Trp | Asn | Glu | Val | Ser | Glu | Ser | Pro | Ser | Asn | Asp | His |
| | 370 | | | | | 375 | | | | | 380 | | | | |
| Leu | Gln | Gly | Gly | Ala | Leu | Thr | Tyr | Val | Asn | Ser | Pro | Leu | Thr | Pro | Asp |

```
                385                 390                 395                 400
Ala Asn Ser Asn Phe Arg Leu Leu Asn Arg Thr Pro Thr Asn Gln Ser
                    405                 410                 415

Gly Thr Thr Arg Tyr Asp Thr Asp Lys Ser Lys Gly Gly Phe Glu Leu
                    420                 425                 430

Leu Leu Ala Asn Asp Val Asp Asn Ser Asn Pro Val Gln Ala Glu
                    435                 440                 445

Gln Leu Asn Trp Leu Tyr Tyr Leu Met Asn Phe Gly Ser Ile Thr Ala
            450                 455                 460

Asn Asp Pro Thr Ala Asn Phe Asp Gly Ile Arg Val Asp Ala Val Asp
465                 470                 475                 480

Asn Val Asp Ala Asp Leu Leu Gln Ile Ala Ser Asp Tyr Phe Lys Leu
                    485                 490                 495

Ala Tyr Gly Thr Ser Leu Ser Asp Thr Asn Ala Asn Gln His Leu Ser
                    500                 505                 510

Ile Leu Glu Asp Trp Ser Ala Asn Asp Ala Glu Tyr Met Ser Lys Thr
            515                 520                 525

Gly Ser Asn Gln Leu Thr Met Asp Thr Tyr Thr Gln Gln Leu Leu
            530                 535                 540

Phe Ser Leu Thr Lys Gln Val Gly Asn Arg Ala Asp Met Arg Arg Phe
545                 550                 555                 560

Leu Glu Tyr Phe Met Ile Asn Arg Ala Asn Asp Ser Thr Glu Asn Val
                    565                 570                 575

Ala Thr Pro Asn Tyr Ser Phe Val Arg Ala His Asp Ser Glu Val Gln
                    580                 585                 590

Thr Val Ile Ala Thr Ile Ile Lys Asp Leu His Pro Asp Val Val Asn
            595                 600                 605

Ser Leu Ala Pro Thr Gln Ala Gln Leu Glu Glu Ala Phe Ala Val Tyr
            610                 615                 620

Asn Ala Asp Met Asn Arg Val Asp Lys Gln Tyr Thr Gln Tyr Asn Met
625                 630                 635                 640

Pro Ser Ala Tyr Ala Met Leu Leu Thr Asn Lys Asp Thr Ile Pro Arg
                    645                 650                 655

Val Tyr Tyr Gly Asp Leu Tyr Thr Asp Asp Gly Glu Tyr Met Gly Thr
                    660                 665                 670

Gln Thr Pro Tyr Tyr Asp Ala Ile Val Asn Leu Leu Gln Ser Arg Val
            675                 680                 685

Lys Tyr Val Ala Gly Gly Gln Ser Met Ala Val Asp Gln His Asp Ile
            690                 695                 700

Leu Thr Ser Val Arg Tyr Gly Lys Asn Leu Ala Asp Ala Asn Ala Thr
705                 710                 715                 720

Ser Asp Asp Leu Thr Ser Ile Asn Ser Gly Ile Gly Val Ile Val Ser
                    725                 730                 735

Asn Asn Pro Asn Leu Ser Leu Ala Ser Gly Glu Thr Val Val Leu His
                    740                 745                 750

Met Gly Ile Ala His Ala Asn Gln Val Tyr Arg Glu Ile Leu Glu Thr
            755                 760                 765

Thr Asp Asn Gly Ile Ala Asn Asn Thr Asp Ile Phe Lys Thr Thr Asp
            770                 775                 780

Ser Asn Gly Asp Leu Ile Phe Thr Ala Ser Glu Ile His Gly Tyr Ser
785                 790                 795                 800

Asn Val Gln Val Ser Gly Phe Leu Ser Val Trp Ala Pro Lys Asp Ala
                    805                 810                 815
```

-continued

Thr Asp Asp Gln Asp Val Arg Thr Ala Ala Ser Glu Ser Thr Ser Asn
        820                 825                 830

Asp Gly Asn Thr Leu His Ser Asn Ala Ala Leu Asp Ser Asn Leu Ile
        835                 840                 845

Tyr Glu Gly Phe Ser Asn Phe Gln Ser Thr Pro Gln Ser Glu Ser Glu
850                     855                 860

Phe Ala Asn Val Lys Ile Ala Ala Asn Val Asn Leu Phe Lys Ser Trp
865                     870                 875                 880

Gly Val Thr Ser Phe Gln Met Ala Pro Gln Tyr Arg Ser Ser Thr Asp
                885                 890                 895

Thr Ser Phe Leu Asp Ser Ile Ile Gln Asn Gly Tyr Ala Phe Thr Asp
            900                 905                 910

Arg Tyr Asp Leu Gly Phe Glu Thr Pro Thr Lys Tyr Gly Thr Asp Gln
        915                 920                 925

Gln Leu Arg Asp Ala Ile Lys Ala Leu His Ala Asn Gly Ile Gln Ala
        930                 935                 940

Met Ala Asp Phe Val Pro Asp Gln Ile Tyr Asn Leu Pro Gln Thr Glu
945                 950                 955                 960

Leu Val Ser Val Ser Arg Thr Asp Ser Leu Gly Asn Gln Ser Ala Asn
                965                 970                 975

Ser Asn Ala Ala Asn Val Leu Tyr Val Ser His Thr Val Gly Gly Gly
            980                 985                 990

Glu Tyr Gln Ser Lys Tyr Gly Gly Glu Phe Leu Ala Ile Ile Lys Ser
            995                 1000                1005

Lys Tyr Pro Ser Leu Phe Lys Thr Ile Gln Val Ser Thr Gly Leu
        1010                1015                1020

Pro Ile Asp Asp Ser Thr Lys Ile Lys Glu Trp Ser Ala Lys Tyr
        1025                1030                1035

Phe Asn Gly Ser Asn Ile Gln Gly Arg Gly Phe Gly Tyr Val Leu
        1040                1045                1050

Ser Asp Gly Gly Thr Gln Asn Tyr Phe Lys Val Ile Ser Asn Ser
        1055                1060                1065

Thr Asp Asp Asp Phe Leu Pro Asn Gln Leu Thr Gly Lys Pro Thr
        1070                1075                1080

Met Thr Gly Phe Glu Gln Thr Ser Lys Gly Ile Val Tyr Tyr Ser
        1085                1090                1095

Lys Ser Gly Ile Gln Ala Lys Asn Gln Phe Val Lys Asp Asp Val
        1100                1105                1110

Ser Gly Asn Tyr Tyr Tyr Phe Asn Lys Asn Gly Leu Met Thr Val
        1115                1120                1125

Gly Ser Lys Thr Ile Asn Gly Lys Asn Tyr Met Phe Leu Pro Asn
        1130                1135                1140

Gly Val Glu Leu Arg Gly Ser Phe Leu Gln Thr Ala Asp Gly Thr
        1145                1150                1155

Val Asn Tyr Tyr Ala Thr Asn Gly Ala Gln Val Gln Asp Ser Tyr
        1160                1165                1170

Val Thr Asp Thr Glu Gly Asn Ser Tyr Tyr Phe Asp Gly Asp Gly
        1175                1180                1185

Glu Met Val Thr Gly Thr Tyr Thr Val Asp Gly His Ala Gln Tyr
        1190                1195                1200

Phe Asp Val Asn Gly Val Gln Thr Lys Gly Ala Ile Ile Thr Leu
        1205                1210                1215

-continued

| | | | | | | | | | | | | |
|---|---|---|---|---|---|---|---|---|---|---|---|---|
| Gly | Gly<br>1220 | Val | Gln | Arg | Tyr<br>1225 | Tyr | Gln | Ala | Gly | Asn<br>1230 | Gly | Asn Leu Ala |
| Thr | Asn<br>1235 | Gln | Tyr | Val | Ser<br>1240 | Tyr | Asn | Asn | Ser | Trp<br>1245 | Tyr | Tyr Ala Asn |
| Thr | Lys<br>1250 | Gly | Glu | Leu | Val | Thr<br>1255 | Gly | Val | Gln | Ser | Ile<br>1260 | Asn Gly Asn |
| Val | Gln<br>1265 | Tyr | Phe | Ala | Ser | Asn<br>1270 | Gly | Gln | Gln | Ile | Lys<br>1275 | Gly Gln Ile |
| Val | Val<br>1280 | Thr | Gly | Asn | Gln | Lys<br>1285 | Ser | Tyr | Tyr | Asp | Ala<br>1290 | Asn Thr Gly |
| Asn | Leu<br>1295 | Ile | Lys | Asn | Asp | Phe<br>1300 | Leu | Thr | Pro | Asp | Gln<br>1305 | Gly Lys Thr |
| Trp | Tyr<br>1310 | Tyr | Ala | Asp | Gln | Asp<br>1315 | Gly | Asn | Leu | Val | Val<br>1320 | Gly Ala Gln |
| Glu | Val<br>1325 | Asn | Gly | His | Lys | Leu<br>1330 | Tyr | Phe | Asp | Asp | Asn<br>1335 | Gly Ile Gln |
| Ile | Lys<br>1340 | Asp | Gln | Ile | Ile | Ser<br>1345 | Asn | Asp | Gly | Gln | Gln<br>1350 | Tyr Tyr Tyr |
| Gln | Gly<br>1355 | Gly | Asn | Gly | Asp | Leu<br>1360 | Val | Thr | Asn | Arg | Tyr<br>1365 | Ile Ser Tyr |
| Asn | Asp<br>1370 | Ser | Trp | Tyr | Tyr | Ala<br>1375 | Asp | Ala | Thr | Gly | Val<br>1380 | Leu Val Thr |
| Gly | Gln<br>1385 | Gln | Ile | Ile | Asn | Gly<br>1390 | Glu | Thr | Gln | Tyr | Phe<br>1395 | Arg Thr Asp |
| Gly | Arg<br>1400 | Gln | Val | Lys | Gly | Gln<br>1405 | Ile | Ile | Ala | Asp | Gly<br>1410 | Asp Lys Gln |
| His | Tyr<br>1415 | Tyr | Asp | Ala | Asp | Ser<br>1420 | Gly | Asn | Leu | Val | Lys<br>1425 | Asn Asn Phe |
| Val | Thr<br>1430 | Val | Asp | Gln | Gly | Lys<br>1435 | Thr | Trp | Tyr | Tyr | Ala<br>1440 | Asp Gln Asp |
| Gly | Asn<br>1445 | Leu | Ser | Leu | Val | Asp<br>1450 | Arg | His | His | His | His<br>1455 | His His |

What is claimed is:

1. A composition comprising a graft copolymer that comprises:
   (i) a backbone comprising dextran, wherein the dextran comprises a product of a glucosyltransferase enzyme comprising an amino acid sequence that is at least 90% identical to SEQ ID NO:6 or SEQ ID NO:7, and
   (ii) one or more poly alpha-1,3-glucan side chains comprising at least about 95% alpha-1,3-glucosidic linkages;
   wherein the composition is
   (a) a product for aqueous liquid absorption selected from the group consisting of baby diapers, potty training pants, incontinence products, feminine hygiene products, wound healing dressings, and sanitary towels, or
   (b) a personal care product, household product, medical product, or industrial product.

2. The composition of claim 1, wherein the one or more poly alpha-1,3-glucan side chains comprise at least about 98% alpha-1,3-glucosidic linkages.

3. The composition of claim 1, wherein the weight-average molecular weight of the one or more poly alpha-1, 3-glucan side chains is at least about 1620 Daltons.

4. The composition of claim 3, wherein the weight-average molecular weight of the one or more poly alpha-1, 3-glucan side chains is at least about 5000 Daltons.

5. The composition of claim 4, wherein the weight-average molecular weight of the one or more poly alpha-1, 3-glucan side chains is at least about 60000 Daltons.

6. The composition of claim 1, wherein the dextran comprises a product of a glucosyltransferase enzyme comprising an amino acid sequence that is at least 95% identical to SEQ ID NO:6 or SEQ ID NO:7.

7. The composition of claim 6, wherein the dextran comprises a product of a glucosyltransferase enzyme comprising an amino acid sequence that is at least 98% identical to SEQ ID NO:6 or SEQ ID NO:7.

8. The composition of claim 7, wherein the dextran comprises a product of a glucosyltransferase enzyme comprising the amino acid sequence of SEQ ID NO:6 or SEQ ID NO:7.

9. The composition of claim 1, wherein the weight-average molecular weight of the dextran is at least about 10 million Daltons.

10. The composition of claim 9, wherein the weight-average molecular weight of the dextran is at least about 50 million Daltons.

11. The composition of claim 10, wherein the weight-average molecular weight of the dextran is at least about 100 million Daltons.

12. The composition of claim 1, wherein the dextran comprises at least 85% alpha-1,6 glucosidic linkages.

13. The composition of claim 1, wherein the graft copolymer comprises at least about 2.0 wt % dextran.

14. The composition of claim 1, wherein the graft copolymer is insoluble under aqueous conditions.

15. The composition of claim 1, wherein the composition is said product for aqueous liquid absorption selected from the group consisting of baby diapers, potty training pants, incontinence products, feminine hygiene products, wound healing dressings, and sanitary towels.

16. The composition of claim 1, wherein the composition is said personal care product, household product, medical product, or industrial product.

17. The composition of claim 16, wherein the composition is said personal care product.

18. The composition of claim 16, wherein the composition is said household product.

19. The composition of claim 16, wherein the composition is said medical product.

20. The composition of claim 16, wherein the composition is said industrial product.

* * * * *